United States Patent
Zhou et al.

(10) Patent No.: US 9,944,707 B2
(45) Date of Patent: Apr. 17, 2018

(54) ANTIBODIES THAT BIND EPIDERMAL GROWTH FACTOR RECEPTOR (EGFR)

(71) Applicant: Sorrento Therapeutics, Inc., San Diego, CA (US)

(72) Inventors: Heyue Zhou, San Diego, CA (US); Randy Gastwirt, San Diego, CA (US); Barbara A. Swanson, Encinatis, CA (US); John Dixon Gray, San Diego, CA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 13/893,312

(22) Filed: May 13, 2013

(65) Prior Publication Data

US 2013/0309233 A1 Nov. 21, 2013

Related U.S. Application Data

(60) Provisional application No. 61/648,391, filed on May 17, 2012.

(51) Int. Cl.
C07K 16/28 (2006.01)
A61K 39/00 (2006.01)

(52) U.S. Cl.
CPC .... C07K 16/2863 (2013.01); *A61K 2039/505* (2013.01); *C07K 2317/21* (2013.01); *C07K 2317/73* (2013.01); *C07K 2317/732* (2013.01); *C07K 2317/76* (2013.01); *C07K 2317/92* (2013.01)

(58) Field of Classification Search
CPC .... C07K 16/18; C07K 16/28; C07K 16/2863; C07K 2317/21; C07K 2317/622; C07K 2317/73; C07K 2317/732; C07K 2317/92; A61K 2039/505
See application file for complete search history.

(56) References Cited

U.S. PATENT DOCUMENTS

| | | | |
|---|---|---|---|
| 7,247,301 B2 | 7/2007 | van de Winkel et al. | |
| 7,723,484 B2 | 5/2010 | Beidler et al. | |
| 7,820,877 B2 | 10/2010 | Jacobovits et al. | |
| 8,329,421 B2 | 12/2012 | Powell et al. | |
| 2002/0173629 A1 | 11/2002 | Jakobovits et al. | |
| 2006/0216288 A1 | 9/2006 | Chang | |
| 2010/0081796 A1 | 4/2010 | Brinkmann et al. | |
| 2010/0247533 A1 | 9/2010 | Friess et al. | |
| 2011/0117110 A1 | 5/2011 | Akamatsu et al. | |
| 2011/0287112 A1 | 11/2011 | Bukhalid et al. | |
| 2012/0308576 A1 | 12/2012 | Bukhalid et al. | |
| 2013/0131320 A1 | 5/2013 | Kumagai et al. | |
| 2013/0149299 A1 | 6/2013 | Baughman et al. | |
| 2013/0171174 A1 | 7/2013 | Wang et al. | |

FOREIGN PATENT DOCUMENTS

| | | |
|---|---|---|
| WO | 1995/025167 A1 | 9/1995 |
| WO | 1998/050433 A2 | 11/1998 |
| WO | 2002/100348 A2 | 12/2002 |
| WO | 2004/056847 A2 | 7/2004 |
| WO | 2005/090407 A1 | 9/2005 |
| WO | 2007/058823 A2 | 5/2007 |
| WO | 2011156617 | 12/2011 |
| WO | 2012/058588 A2 | 5/2012 |

OTHER PUBLICATIONS

Paul, W.E., Fundamental Immunology, 3rd Edition, Raven Press, New York, Chapt. 8, pp. 292-295, 1993.*
Rudikoff S., et al., Proc. Natl. Acad. Sci. USA, 79(6):1979-1983, Mar. 1982.*
Colman P. M., Research in Immunology, 145:33-36, 1994.*
Fan et al. "Bivalent and Monovalent Fragments of 225 Anti-Epidermal Blockade of Epidermal Growth Factor Receptor Function by Growth Factor Receptor Monoclonal Antibodies" Cancer Res. 53:4322-4328, 1993.
Goldstein et al. "Biological efficacy of a chimeric antibody to the epidermal growth factor receptor in a human tumor xenograft model" Clin. Cancer Res. 1:1311-1318, 1995.
Bleeker et al. "Dual Mode of Action of a Human Anti-Epidermal Growth Factor Receptor Monoclonal Antibody for Cancer Therapy" J. Immunol. 173:4699-4707, 2004.
Martinelli et al. (2009) "Anti-epidermal growth factor receptor monoclonal antibodies in cancer therapy," Clin. Exp. Immunol. 158(1):1-9.

* cited by examiner

*Primary Examiner* — Robert S Landsman
(74) *Attorney, Agent, or Firm* — Lathrop Gage LLP; Andrew T. Wilkins; David E. Johnson

(57) ABSTRACT

There is disclosed compositions and methods relating to or derived from anti-EGFR antibodies. More specifically, there is disclosed fully human antibodies that bind EGFR, EGFR-binding fragments and derivatives of such antibodies, and EGFR-binding polypeptides comprising such fragments. Further still, there is disclosed antibody fragments and derivatives and polypeptides, and methods of using such antibodies, antibody fragments and derivatives and polypeptides, including methods of treating or diagnosing subjects having EGFR-related disorders or conditions.

16 Claims, 17 Drawing Sheets

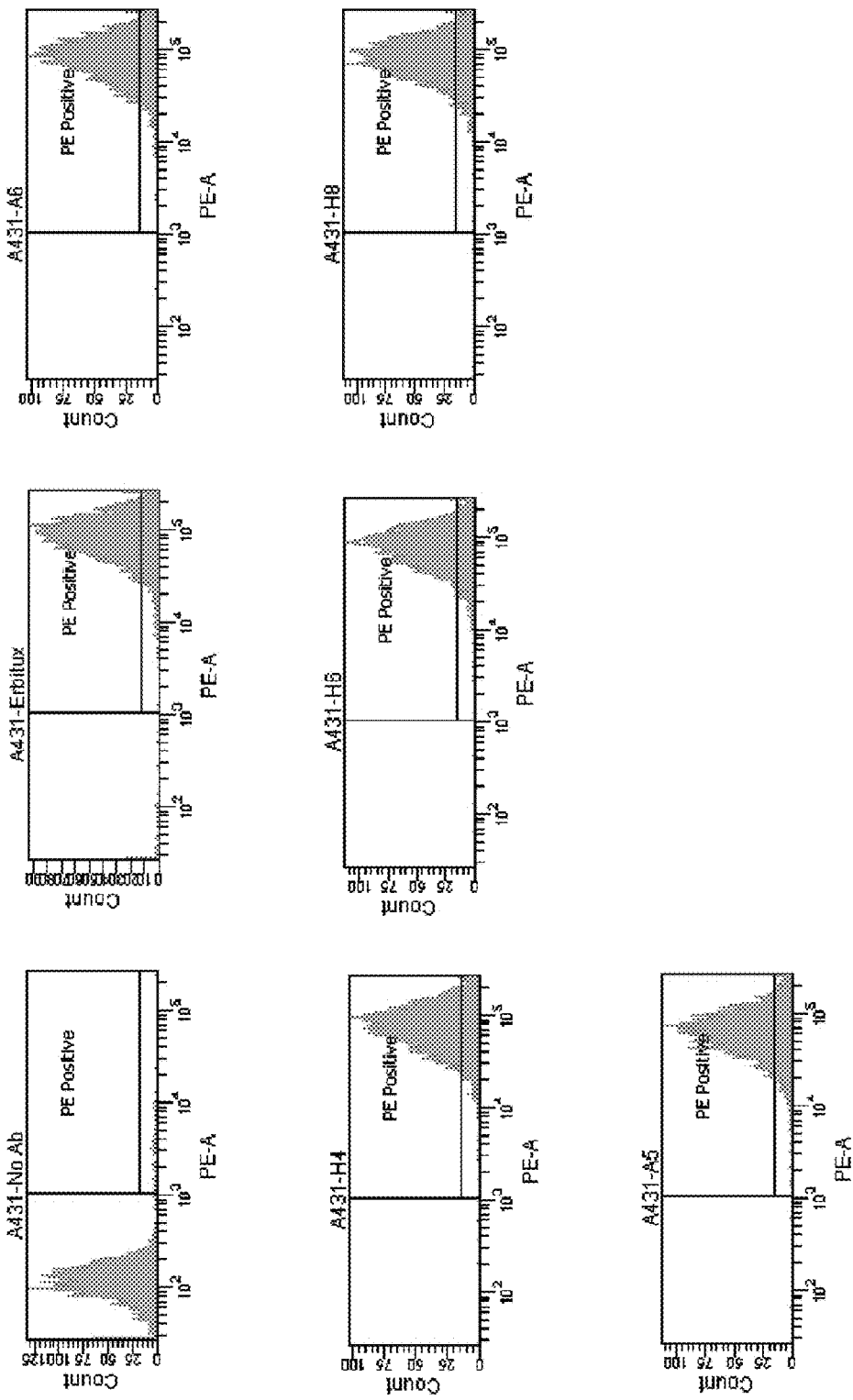
Fig 1. Binding of EGFR Antibodies to A431 Cells

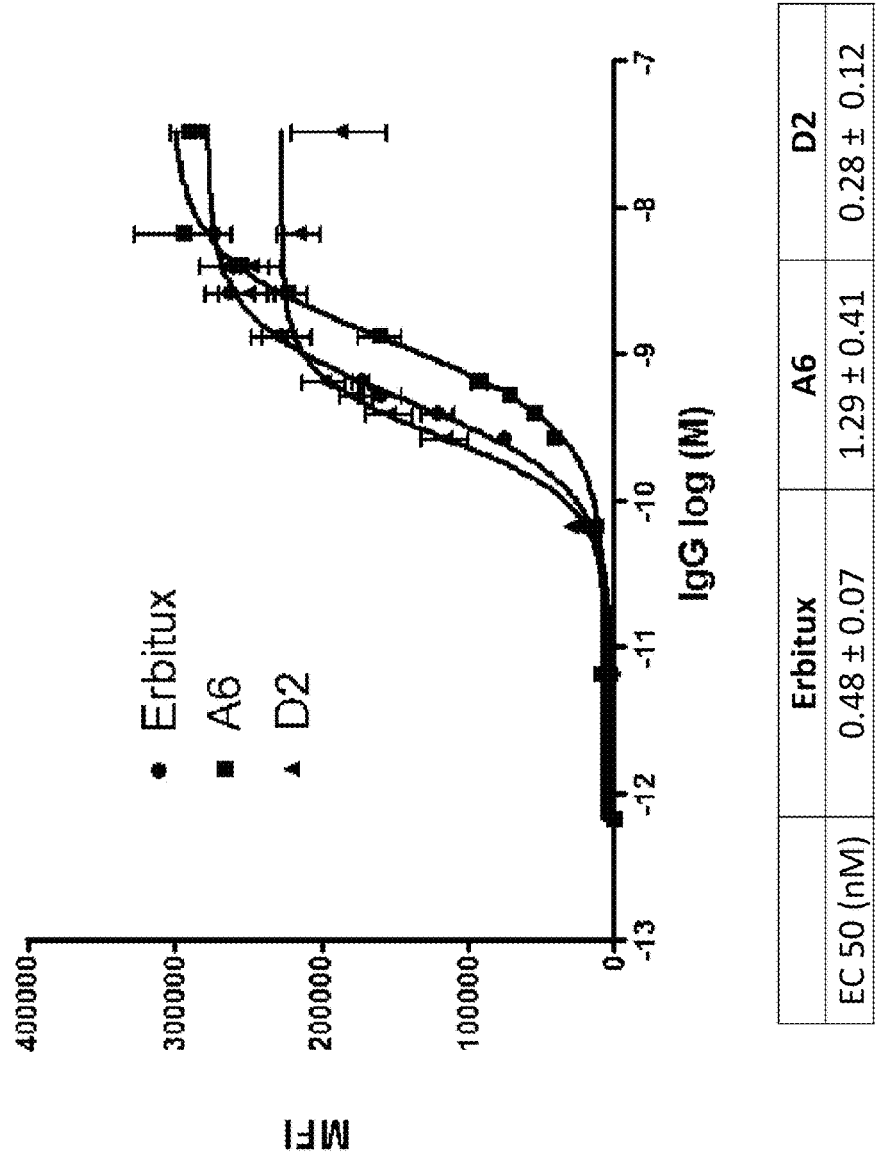
Figure 2. EC50 Measurements for A431 Cell Surface EGFR Binding by Anti-EGFR Antibodies

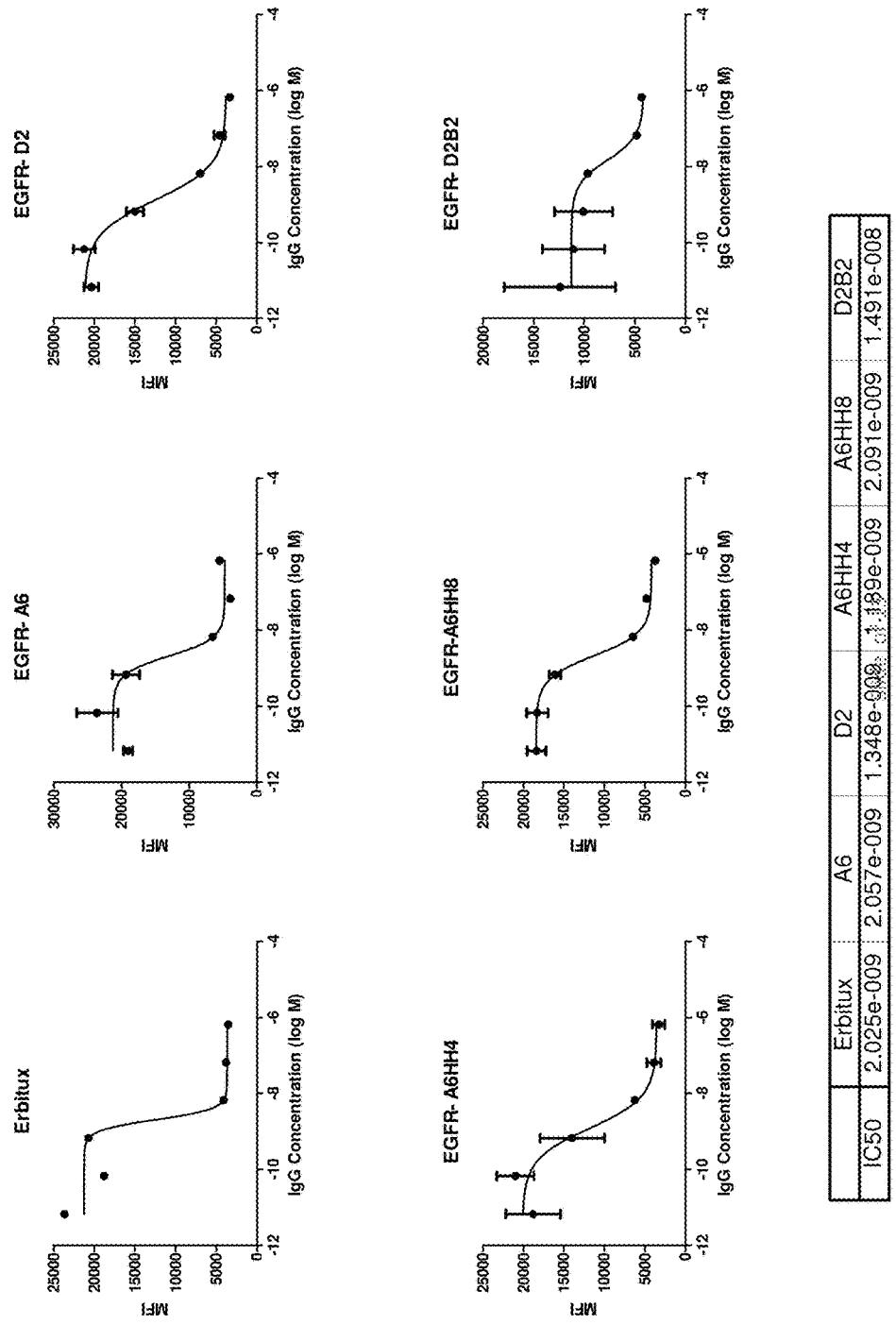
Figure 3. Blocking of EGF Binding to EGFR on A431 Cells by Anti-EGFR Antibodies

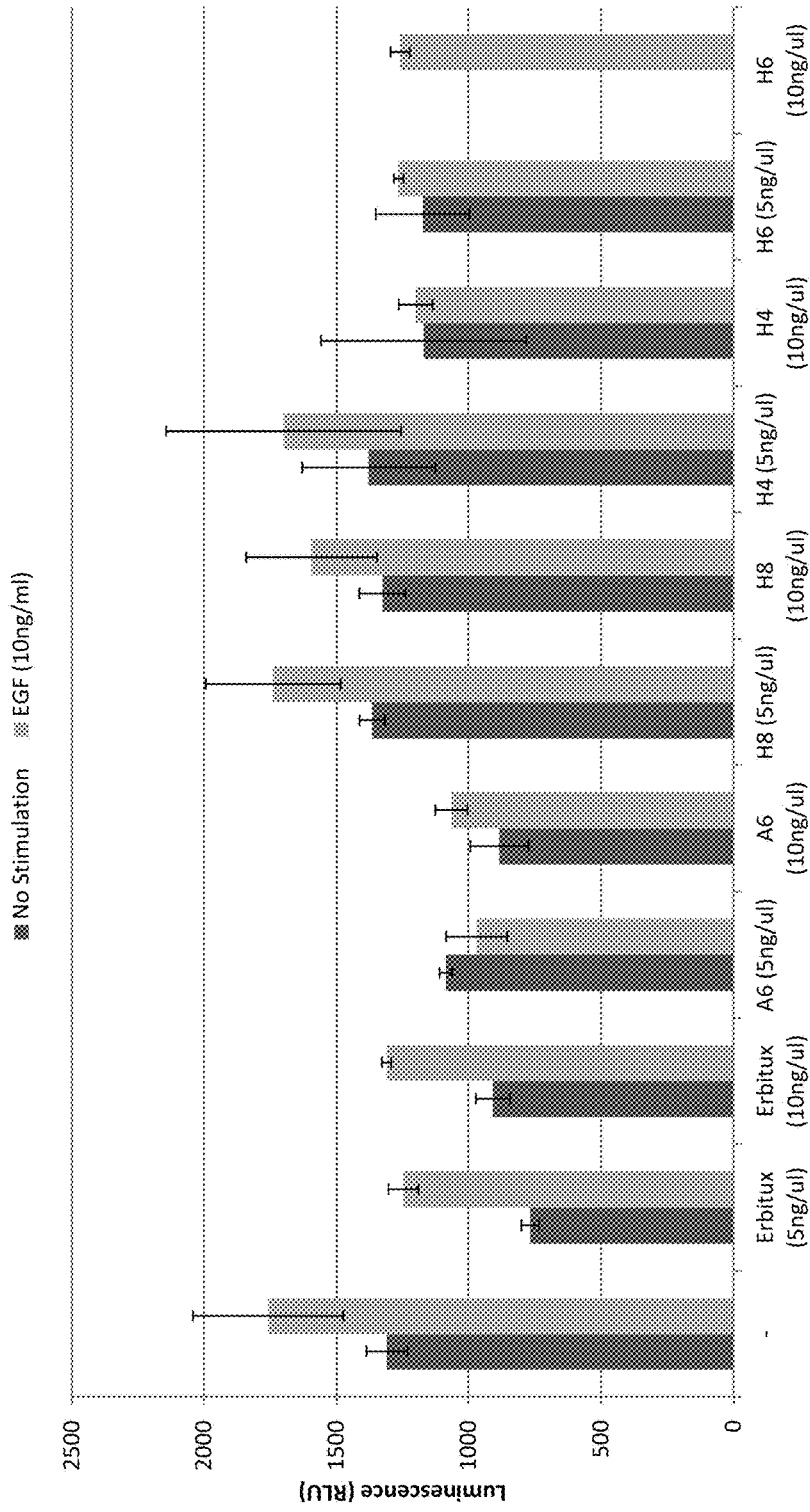

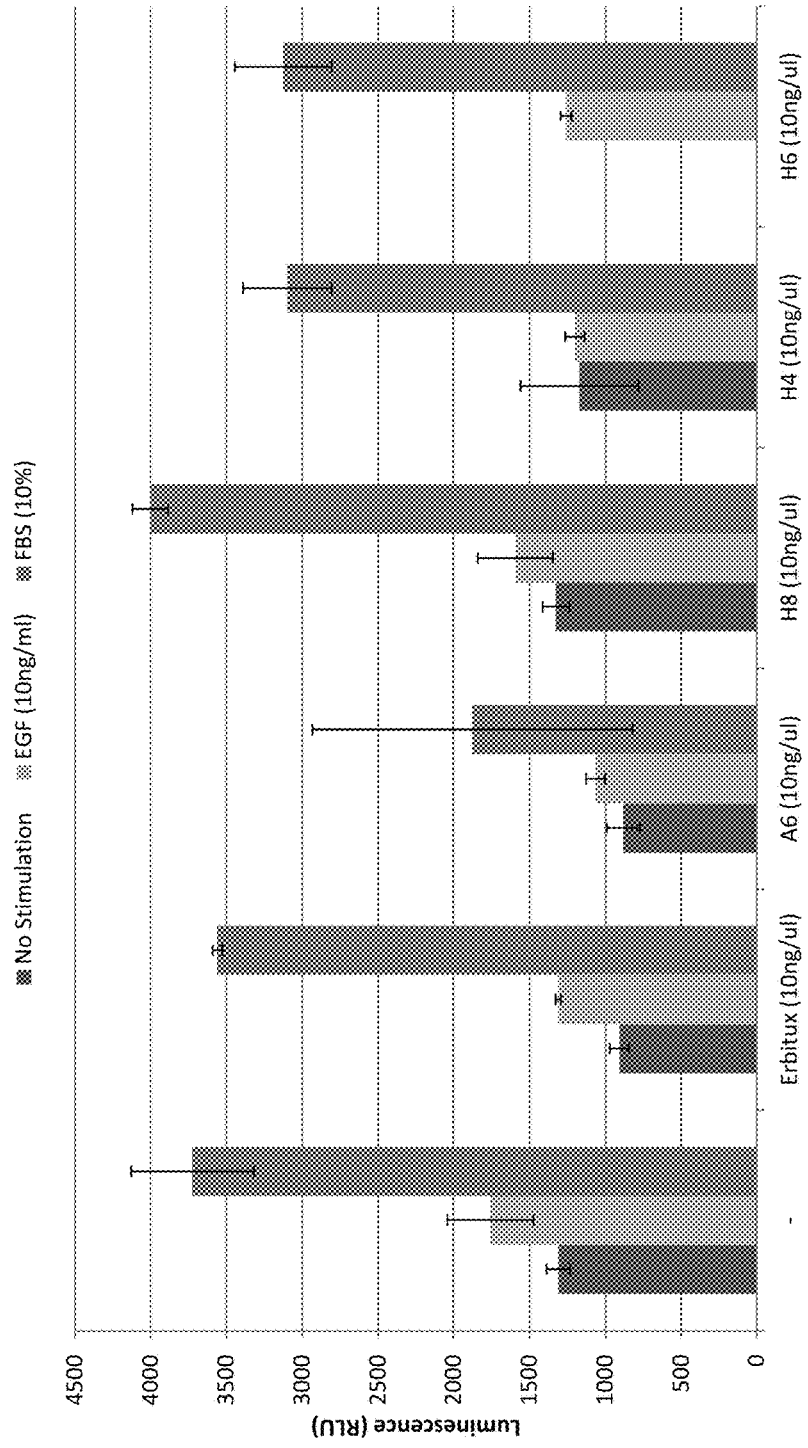
Figure 4b. Inhibitory Effect of Anti-EGFR Antibodies on Cell Proliferation. Antagonism of MCF7 Cell Proliferation Stimulated by EGF or Serum

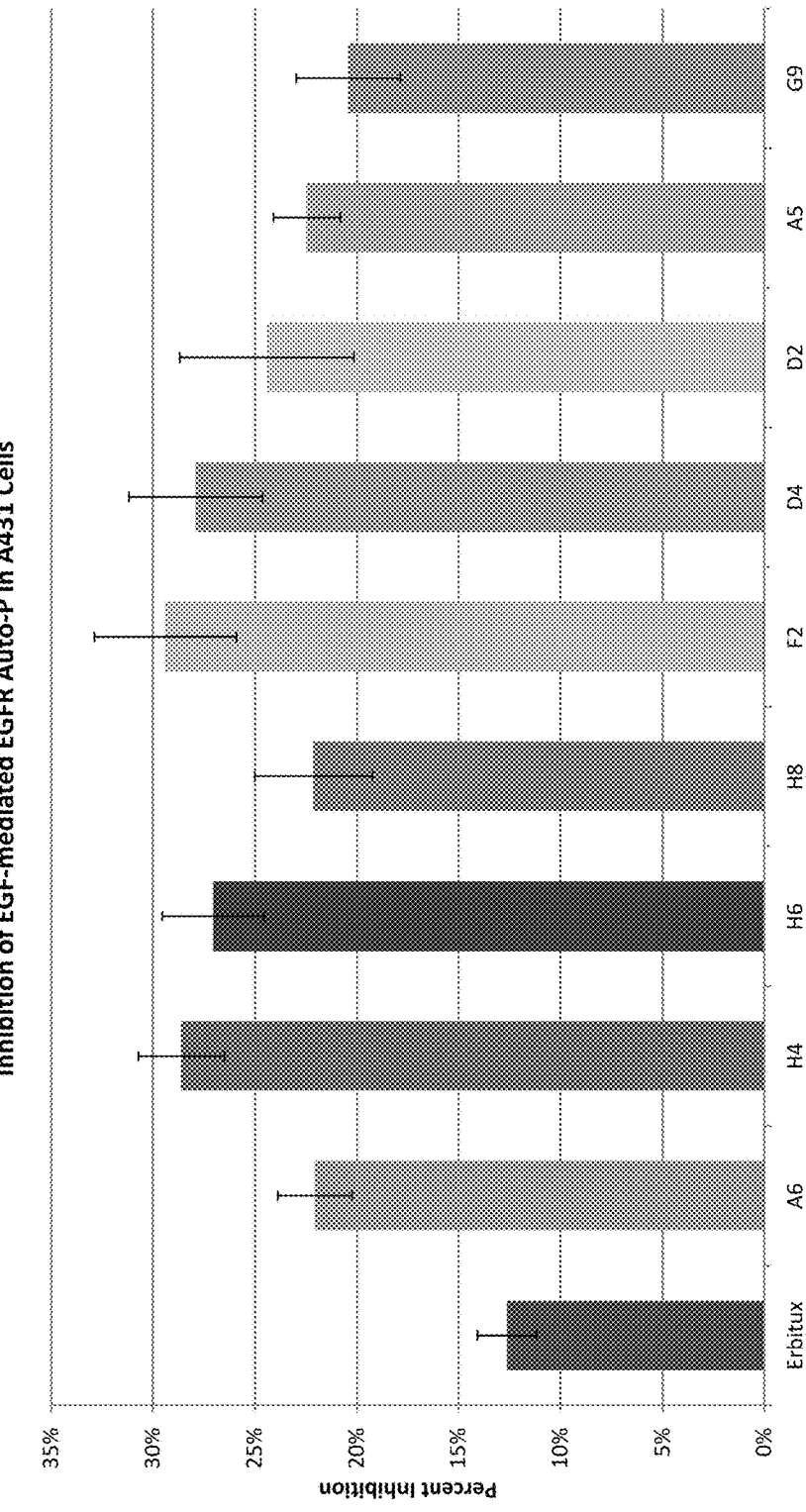
Figure 5. Inhibition of EGFR Activating Auto-Phosphorylation in A431 Cells Stimulated with EGF by Anti-EGFR Antibodies

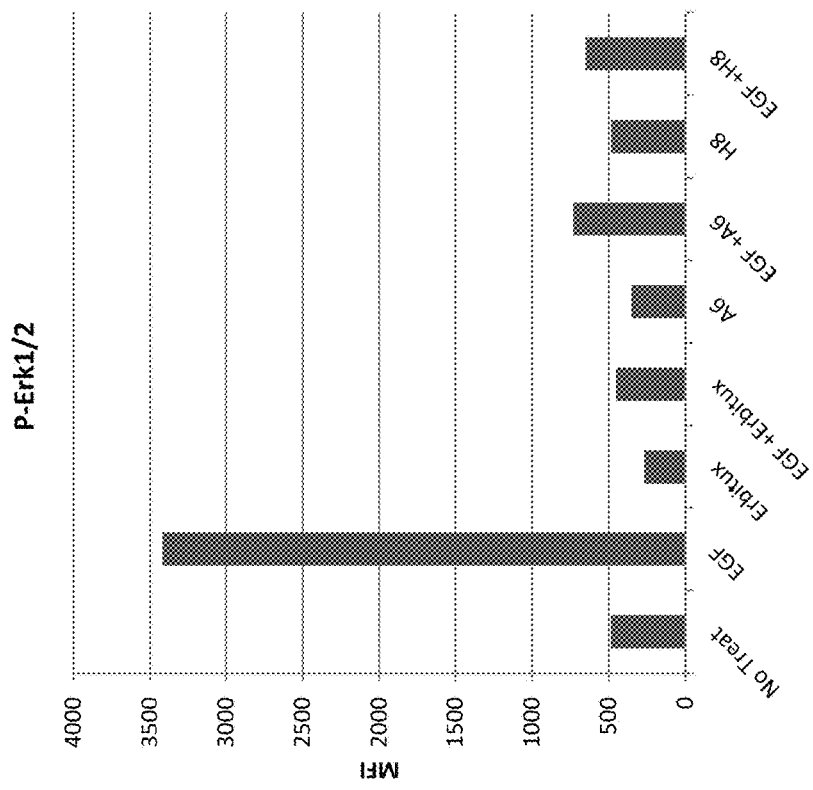
Figure 6a. Inhibition of Cell Signaling by Anti-EGFR Antibodies. Antagonism of ERK1/2 Activation by Phosphorylation in A431 Cells

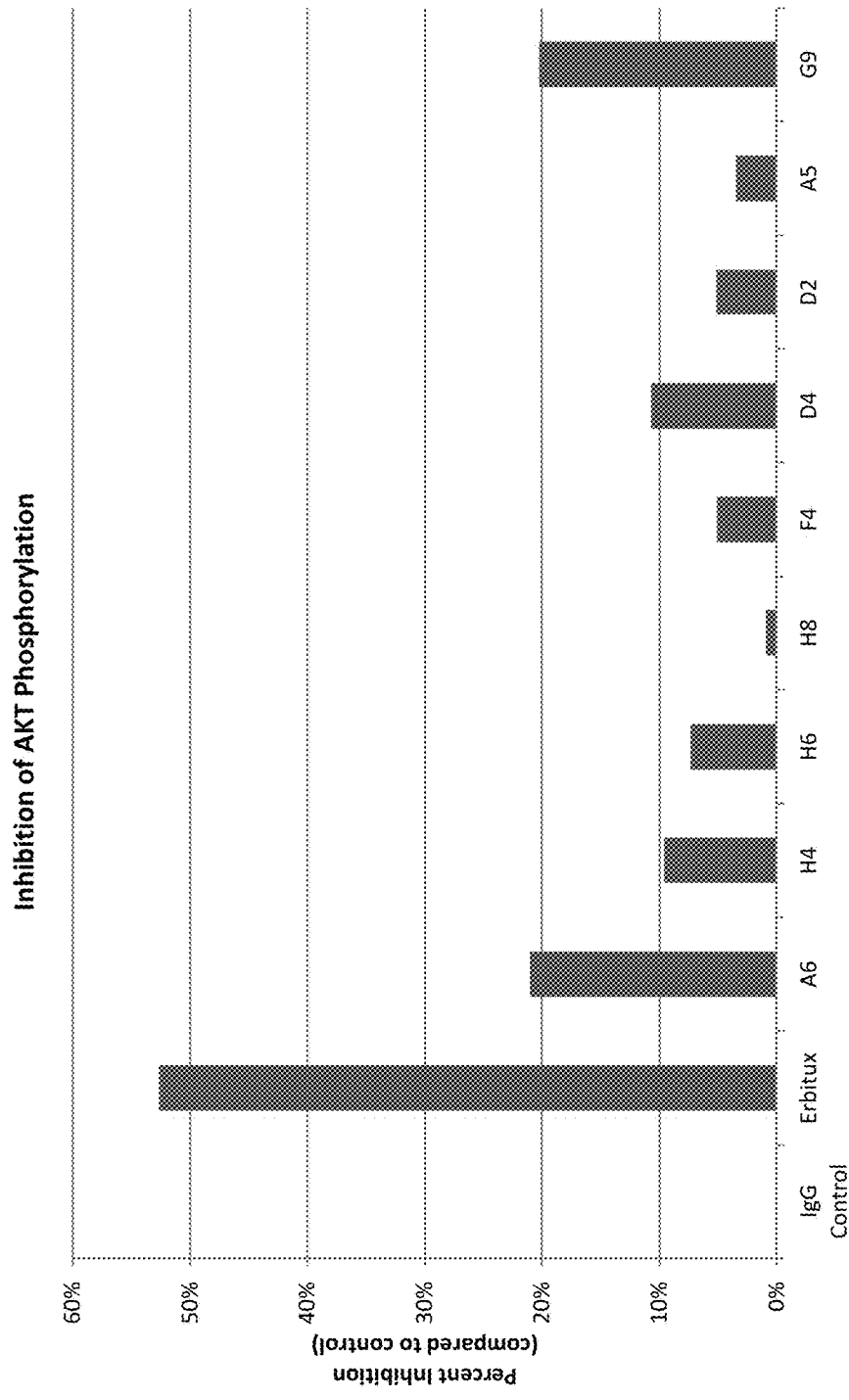
Figure 6b. Inhibition of Cell Signaling by Anti-EGFR Antibodies. Antagonism of AKT Activation by Phosphorylation in A431 Cells

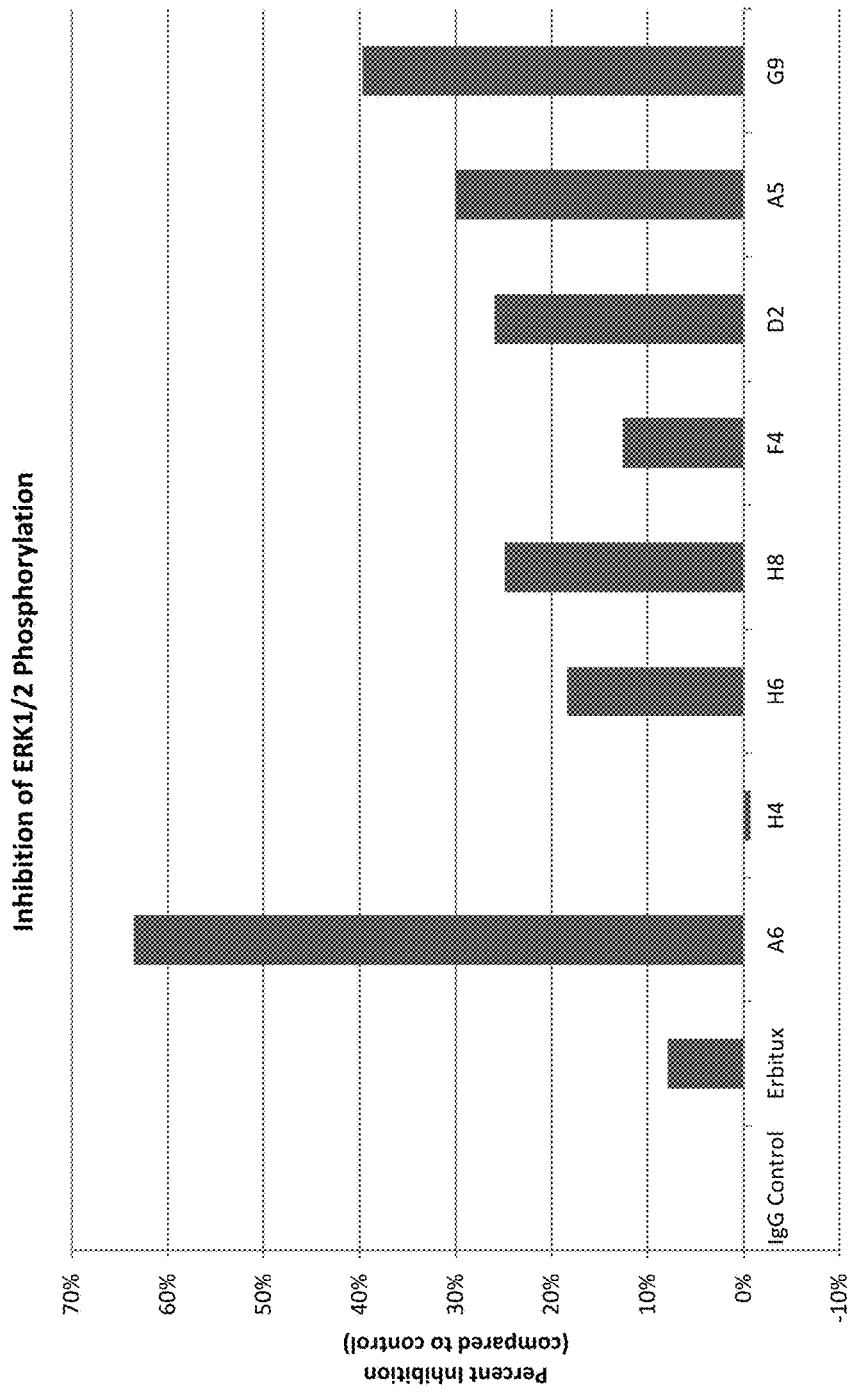
Figure 6c. Inhibition of Cell Signaling by Anti-EGFR Antibodies. Antagonism of ERK1/2 Activation by Phosphorylation in MCF7 Cells Figure 16 A and B
A
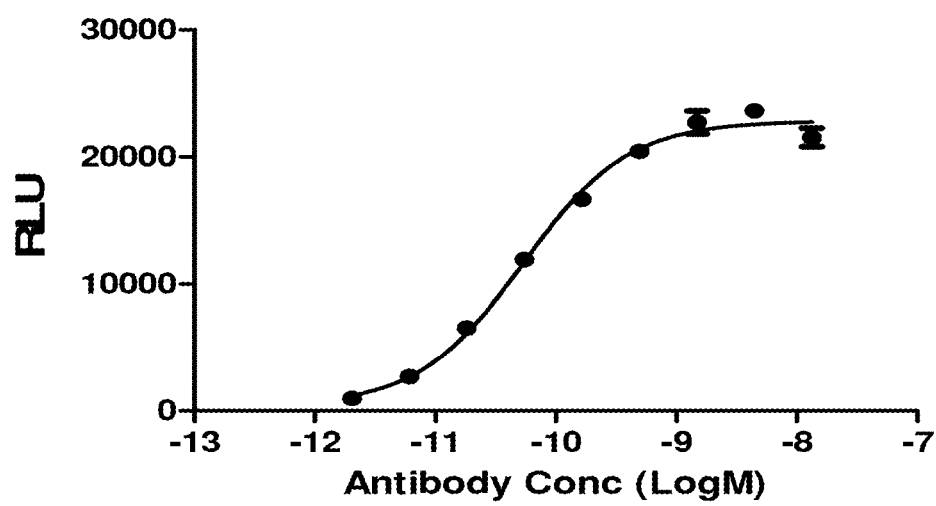
B
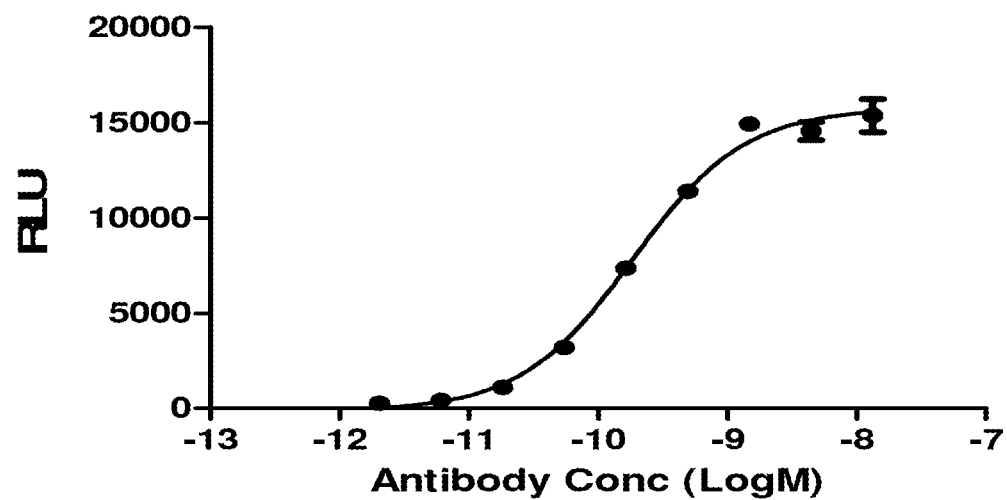

ANTIBODIES THAT BIND EPIDERMAL GROWTH FACTOR RECEPTOR (EGFR)

CROSS REFERENCE TO RELATED APPLICATION

The present disclosure claims priority to U.S. Provisional Patent Application Ser. No. 61/648,391 filed on 17 May 2012.

TECHNICAL FIELD

The present disclosure provides compositions and methods relating to or derived from anti-EGFR antibodies. More specifically, the present disclosure provides human antibodies that bind EGFR, EGFR-binding fragments and derivatives of such antibodies, and EGFR-binding polypeptides comprising such fragments. Further still, the present disclosure provides antibody fragments and derivatives and polypeptides, and methods of using such antibodies, antibody fragments and derivatives and polypeptides, including methods of treating or diagnosing subjects having EGFR-related disorders or conditions.

BACKGROUND

Cancer remains one of the most deadly threats to human health. In the U.S., cancer affects nearly 1.3 million new patients each year, and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult. Furthermore, cancers can arise from almost any tissue in the body through malignant transformation of one or a few normal cells within the tissue, and each type of cancer with particular tissue origin differs from the others.

Current methods of cancer treatment are relatively non-selective. Surgery removes the diseased tissue; radiotherapy shrinks solid tumors; and chemotherapy kills rapidly dividing cells. Chemotherapy, in particular, results in numerous side effects, in some cases so severe as to limit the dosage that can be given and thus preclude the use of potentially effective drugs. Moreover, cancers often develop resistance to chemotherapeutic drugs.

Thus, there is an urgent need for more specific and more effective cancer therapies.

EGFR was cloned as 55 kD of I type membrane protein that belong to an immunoglobulin family (*The EMBO Journal* (1992), vol. 11, issue 11, p. 3887-3895, JP5336973, JP7291996). Human EGFR cDNA is composed of the base sequence shown in EMBL/GenBank Acc. No. NM$_{005018}$ and mouse EGFR cDNA is composed of the base sequence shown in Acc. No. X67914, and those expressions are observed when thymus cells differentiate from CD4−CD8− cell into CD4+CD8+ cell (*International Immunology* (1996), vol. 18, issue 5, p. 773-780., *J. Experimental Med.* (2000), vol. 191, issue 5, p. 891-898.). It is reported that EGFR expression in periphery is observed in myeloid cells including T cells or B lymphocytes activated by stimulation from antigen receptors, or activated macrophages (*International Immunology* (1996), vol. 18, issue 5, p. 765-772.).

SUMMARY

The present disclosure provides a fully human antibody of an IgG class that binds to an EGFR epitope with a binding affinity of at least $10^{-6}$M, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A3 herein), SEQ ID NO. 3/SEQ ID NO. 4 (called A5 herein), SEQ ID NO. 5/SEQ ID NO. 6 (called A6 herein), SEQ ID NO. 7/SEQ ID NO. 8 (called A10 herein), SEQ ID NO. 9/SEQ ID NO. 10 (called A11 herein), SEQ ID NO. 11/SEQ ID NO. 12 (called B1 herein), SEQ ID NO. 13/SEQ ID NO. 14 (called B4 herein), SEQ ID NO. 15/SEQ ID NO. 16 (called B5 herein), SEQ ID NO. 17/SEQ ID NO. 18 (called B6 herein), SEQ ID NO. 19/SEQ ID NO. 20 (called B7 or H3 herein), SEQ ID NO. 21/SEQ ID NO. 22 (called D2 herein), SEQ ID NO. 23/SEQ ID NO. 24 (called D4 or H9 herein), SEQ ID NO. 25/SEQ ID NO. 26 (called D6 herein), SEQ ID NO. 27/SEQ ID NO. 28 (called D10 herein), SEQ ID NO. 29/SEQ ID NO. 30 (called E1 herein), SEQ ID NO. 31/SEQ ID NO. 32 (called EG-A4 herein), SEQ ID NO. 33/SEQ ID NO. 34 (called EG-B7 herein), SEQ ID NO. 35/SEQ ID NO. 36 (called EG-C9 herein), SEQ ID NO. 37/SEQ ID NO. 38 (called EG-D5 herein), SEQ ID NO. 39/SEQ ID NO. 40 (called EG-E9 herein), SEQ ID NO. 41/SEQ ID NO. 42 (called EG-E11 herein), SEQ ID NO. 43/SEQ ID NO. 44 (called EB8 herein), SEQ ID NO. 45/SEQ ID NO. 46 (called EC6 herein), SEQ ID NO. 47/SEQ ID NO. 48 (called EC10 herein), SEQ ID NO. 49/SEQ ID NO. 50 (called ED10 herein), SEQ ID NO. 51/SEQ ID NO. 52 (called EE12 herein), SEQ ID NO. 53/SEQ ID NO. 54 (called RE-A1 herein), SEQ ID NO. 55/SEQ ID NO. 56 (called RE-F3 herein), SEQ ID NO. 57/SEQ ID NO. 58 (called RE-F4 herein), SEQ ID NO. 59/SEQ ID NO. 60 (called G3 herein), SEQ ID NO. 61/SEQ ID NO. 62 (called A6-A1 herein), SEQ ID NO. 63/SEQ ID NO. 64 (called A6-A3 herein), SEQ ID NO. 65/SEQ ID NO. 66 (called A6-A4 herein), SEQ ID NO. 67/SEQ ID NO. 68 (called A6-A5 herein), SEQ ID NO. 69/SEQ ID NO. 70 (called A6-A6 herein), SEQ ID NO. 71/SEQ ID NO. 72 (called A6-A7 herein), SEQ ID NO. 73/SEQ ID NO. 74 (called A6-A8 herein), SEQ ID NO. 75/SEQ ID NO. 76 (called D2GA1 herein), SEQ ID NO. 77/SEQ ID NO. 78 (called D2GA2 herein), SEQ ID NO. 79/SEQ ID NO. 80 (called D2GA4 herein), SEQ ID NO. 81/SEQ ID NO. 82 (called D2GA5 herein), SEQ ID NO. 83/SEQ ID NO. 84 (called A6-A11 herein), SEQ ID NO. 85/SEQ ID NO. 86 (called A6-A12 herein), SEQ ID NO. 87/SEQ ID NO. 88 (called A6-A13 herein), SEQ ID NO. 89/SEQ ID NO. 90 (called A6-A14 herein), SEQ ID NO. 91/SEQ ID NO. 92 (called A6-A15 herein), SEQ ID NO. 93/SEQ ID NO. 94 (called A6-A17 herein), SEQ ID NO. 95/SEQ ID NO. 96 (called A6-A18 herein), SEQ ID NO. 97/SEQ ID NO. 98 (called A6-A20 herein), SEQ ID NO. 99/SEQ ID NO. 100 (called A6-A21 herein), SEQ ID NO. 101/SEQ ID NO. 102 (called A6-A22 herein), SEQ ID NO. 103/SEQ ID NO. 104 (called A6-A23 herein), SEQ ID NO. 105/SEQ ID NO. 106 (called A6-A24 herein), SEQ ID NO. 107/SEQ ID NO. 108 (called D2GA6 herein), SEQ ID NO. 109/SEQ ID NO. 110 (called D2GA9 herein), SEQ ID NO. 111/SEQ ID NO. 112 (called D2GA10 herein), SEQ ID NO. 113/SEQ ID NO. 114 (called D2GA11 herein), SEQ ID NO. 115/SEQ ID NO. 116 (called D2 GB2 herein), SEQ ID NO. 117/SEQ ID NO. 118 (called D2 GB6 herein), SEQ ID NO. 1119/SEQ ID NO. 120 (called D2 GB7 herein), SEQ ID NO. 121/SEQ ID NO. 122 (called D2 GB8 herein), SEQ ID NO. 123/SEQ ID NO. 124 (called D2GC1 herein), SEQ ID NO. 125/SEQ ID NO. 126 (called D2GC4 herein), SEQ ID NO. 127/SEQ ID NO. 128 (called D2GG1 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO.

117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

The present disclosure further provides a method for treating a broad spectrum of mammalian cancers, comprising administering an effective amount of an anti-EGFR polypeptide, wherein the anti-EGFR polypeptide is selected from the group consisting of a fully human antibody of an IgG class that binds to an EGFR epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called A3 herein), SEQ ID NO. 3/SEQ ID NO. 4 (called A2 herein), SEQ ID NO. 5/SEQ ID NO. 6 (called A6 herein), SEQ ID NO. 7/SEQ ID NO. 8 (called A10 herein), SEQ ID NO. 9/SEQ ID NO. 10 (called A11 herein), SEQ ID NO. 11/SEQ ID NO. 12 (called B1 herein), SEQ ID NO. 13/SEQ ID NO. 14 (called B4 herein), SEQ ID NO. 15/SEQ ID NO. 16 (called B5 herein), SEQ ID NO. 17/SEQ ID NO. 18 (called B6 herein), SEQ ID NO. 19/SEQ ID NO. 20 (called B7 or H3 herein), SEQ ID NO. 21/SEQ ID NO. 22 (called D2 herein), SEQ ID NO. 23/SEQ ID NO. 24 (called D4 or H9 herein), SEQ ID NO. 25/SEQ ID NO. 26 (called D6 herein), SEQ ID NO. 27/SEQ ID NO. 28 (called D10 herein), SEQ ID NO. 29/SEQ ID NO. 30 (called E-1 herein), SEQ ID NO. 31/SEQ ID NO. 32 (called EG-A4 herein), SEQ ID NO. 33/SEQ ID NO. 34 (called EG-B7 herein), SEQ ID NO. 35/SEQ ID NO. 36 (called EG-C9 herein), SEQ ID NO. 37/SEQ ID NO. 38 (called EG-D5 herein), SEQ ID NO. 39/SEQ ID NO. 40 (called EG-E9 herein), SEQ ID NO. 41/SEQ ID NO. 42 (called EG-E11 herein), SEQ ID NO. 43/SEQ ID NO. 44 (called EB8 herein), SEQ ID NO. 45/SEQ ID NO. 46 (called EC6 herein), SEQ ID NO. 47/SEQ ID NO. 48 (called EC10 herein), SEQ ID NO. 49/SEQ ID NO. 50 (called ED10 herein), SEQ ID NO. 51/SEQ ID NO. 52 (called EE12 herein), SEQ ID NO.

53/SEQ ID NO. 54 (called RE-A1 herein), SEQ ID NO. 55/SEQ ID NO. 56 (called RE-F3 herein), SEQ ID NO. 57/SEQ ID NO. 58 (called RE-F4 herein), SEQ ID NO. 59/SEQ ID NO. 60 (called G3 herein), SEQ ID NO. 61/SEQ ID NO. 62 (called A6-A1 herein), SEQ ID NO. 63/SEQ ID NO. 64 (called A6-A3 herein), SEQ ID NO. 65/SEQ ID NO. 66 (called A6-A4 herein), SEQ ID NO. 67/SEQ ID NO. 68 (called A6-A5 herein), SEQ ID NO. 69/SEQ ID NO. 70 (called A6-A6 herein), SEQ ID NO. 71/SEQ ID NO. 72 (called A6-A7 herein), SEQ ID NO. 73/SEQ ID NO. 74 (called A6-A8 herein), SEQ ID NO. 75/SEQ ID NO. 76 (called D2GA1 herein), SEQ ID NO. 77/SEQ ID NO. 78 (called D2GA2 herein), SEQ ID NO. 79/SEQ ID NO. 80 (called D2GA4 herein), SEQ ID NO. 81/SEQ ID NO. 82 (called D2GA5 herein), SEQ ID NO. 83/SEQ ID NO. 84 (called A6-A11 herein), SEQ ID NO. 85/SEQ ID NO. 86 (called A6-A12 herein), SEQ ID NO. 87/SEQ ID NO. 88 (called A6-A13 herein), SEQ ID NO. 89/SEQ ID NO. 90 (called A6-A14 herein), SEQ ID NO. 91/SEQ ID NO. 92 (called A6-A15 herein), SEQ ID NO. 93/SEQ ID NO. 94 (called A6-A17 herein), SEQ ID NO. 95/SEQ ID NO. 96 (called A6-A18 herein), SEQ ID NO. 97/SEQ ID NO. 98 (called A6-A20 herein), SEQ ID NO. 99/SEQ ID NO. 100 (called A6-A21 herein), SEQ ID NO. 101/SEQ ID NO. 102 (called A6-A22 herein), SEQ ID NO. 103/SEQ ID NO. 104 (called A6-A23 herein), SEQ ID NO. 105/SEQ ID NO. 106 (called A6-A24 herein), SEQ ID NO. 107/SEQ ID NO. 108 (called D2GA6 herein), SEQ ID NO. 109/SEQ ID NO. 110 (called D2GA9 herein), SEQ ID NO. 111/SEQ ID NO. 112 (called D2GA10 herein), SEQ ID NO. 113/SEQ ID NO. 114 (called D2GA11 herein), SEQ ID NO. 115/SEQ ID NO. 116 (called D2 GB2 herein), SEQ ID NO. 117/SEQ ID NO. 118 (called D2 GB6 herein), SEQ ID NO. 1119/SEQ ID NO. 120 (called D2 GB7 herein), SEQ ID NO. 121/SEQ ID NO. 122 (called D2 GB8 herein), SEQ ID NO. 123/SEQ ID NO. 124 (called D2GC1 herein), SEQ ID NO. 125/SEQ ID NO. 126 (called D2GC4 herein), SEQ ID NO. 127/SEQ ID NO. 128 (called D2GG1 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called A3 herein), SEQ ID NO. 3/SEQ ID NO. 4 (called A2 herein), SEQ ID NO. 5/SEQ ID NO. 6 (called A6 herein), SEQ ID NO. 7/SEQ ID NO. 8 (called A10 herein), SEQ ID NO. 9/SEQ ID NO. 10 (called A11 herein), SEQ ID NO. 11/SEQ ID NO. 12 (called B1 herein), SEQ ID NO. 13/SEQ ID NO. 14 (called B4 herein), SEQ ID NO. 15/SEQ ID NO. 16 (called B5 herein), SEQ ID NO. 17/SEQ ID NO. 18 (called B6 herein), SEQ ID NO. 19/SEQ ID NO. 20 (called B7 or H3 herein), SEQ ID NO. 21/SEQ ID NO. 22 (called D2 herein), SEQ ID NO. 23/SEQ ID NO. 24 (called D4 or H9 herein), SEQ ID NO. 25/SEQ ID NO. 26 (called D6 herein), SEQ ID NO. 27/SEQ ID NO. 28 (called D10 herein), SEQ ID NO. 29/SEQ ID NO. 30 (called E-1 herein), SEQ ID NO. 31/SEQ ID NO. 32 (called EG-A4 herein), SEQ ID NO. 33/SEQ ID NO. 34 (called EG-B7 herein), SEQ ID NO. 35/SEQ ID NO. 36 (called EG-C9 herein), SEQ ID NO. 37/SEQ ID NO. 38 (called EG-D5 herein), SEQ ID NO. 39/SEQ ID NO. 40 (called EG-E9 herein), SEQ ID NO. 41/SEQ ID NO. 42 (called EG-E11 herein), SEQ ID NO. 43/SEQ ID NO. 44 (called EB8 herein), SEQ ID NO. 45/SEQ ID NO. 46 (called EC6 herein), SEQ ID NO. 47/SEQ ID NO. 48 (called EC10 herein), SEQ ID NO. 49/SEQ ID NO. 50 (called ED10 herein), SEQ ID NO. 51/SEQ ID NO. 52 (called EE12 herein), SEQ ID NO. 53/SEQ ID NO. 54 (called RE-A1 herein), SEQ ID NO. 55/SEQ ID NO. 56 (called RE-F3 herein), SEQ ID NO. 57/SEQ ID NO. 58 (called RE-F4 herein), SEQ ID NO. 59/SEQ ID NO. 60 (called G3 herein), SEQ ID NO. 61/SEQ ID NO. 62 (called A6-A1 herein), SEQ ID NO. 63/SEQ ID NO. 64 (called A6-A3 herein), SEQ ID NO. 65/SEQ ID NO. 66 (called A6-A4 herein), SEQ ID NO. 67/SEQ ID NO. 68 (called A6-A5 herein), SEQ ID NO. 69/SEQ ID NO. 70 (called A6-A6 herein), SEQ ID NO. 71/SEQ ID NO. 72 (called A6-A7 herein), SEQ ID NO. 73/SEQ ID NO. 74 (called A6-A8 herein), SEQ ID NO. 75/SEQ ID NO. 76 (called D2GA1 herein), SEQ ID NO. 77/SEQ ID NO. 78 (called D2GA2 herein), SEQ ID NO. 79/SEQ ID NO. 80 (called D2GA4 herein), SEQ ID NO. 81/SEQ ID NO. 82 (called D2GA5 herein), SEQ ID NO. 83/SEQ ID NO. 84 (called A6-A11 herein), SEQ ID NO. 85/SEQ ID NO. 86 (called A6-A12 herein), SEQ ID NO. 87/SEQ ID NO. 88 (called A6-A13 herein), SEQ ID NO. 89/SEQ ID NO. 90 (called A6-A14 herein), SEQ ID NO. 91/SEQ ID NO. 92 (called A6-A15 herein), SEQ ID NO. 93/SEQ ID NO. 94 (called A6-A17 herein), SEQ ID NO. 95/SEQ ID NO. 96 (called A6-A18 herein), SEQ ID NO. 97/SEQ ID NO. 98 (called A6-A20 herein), SEQ ID NO. 99/SEQ ID NO. 100 (called A6-A21 herein), SEQ ID NO. 101/SEQ ID NO. 102 (called A6-A22 herein), SEQ ID NO. 103/SEQ ID NO. 104 (called A6-A23 herein), SEQ ID NO. 105/SEQ ID NO. 106 (called A6-A24 herein), SEQ ID NO. 107/SEQ ID NO. 108 (called D2GA6 herein), SEQ ID NO. 109/SEQ ID NO. 110 (called D2GA9 herein), SEQ ID NO. 111/SEQ ID NO. 112 (called D2GA10 herein), SEQ ID NO. 113/SEQ ID NO. 114 (called D2GA11 herein), SEQ ID NO. 115/SEQ ID NO. 116 (called D2 GB2 herein), SEQ ID NO. 117/SEQ ID NO. 118 (called D2 GB6 herein), SEQ ID NO. 1119/SEQ ID NO. 120 (called D2 GB7 herein), SEQ ID NO. 121/SEQ ID NO. 122 (called D2 GB8 herein), SEQ ID NO. 123/SEQ ID NO. 124 (called D2GC1 herein), SEQ ID NO. 125/SEQ ID NO. 126 (called D2GC4 herein), SEQ ID NO. 127/SEQ ID NO. 128 (called D2GG1 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

BRIEF DESCRIPTION OF THE FIGURES

FIG. 1 shows FACS measurements of various anti-EGFR antibodies binding to A431 cells. The top right figure is for A6, a preferred anti-EGFR antibody.

FIG. 2 shows A6 and D2 cell binding to A431 epidermoid carcinoma cells and an $EC_{50}$ of 1.29 nM and 0.28 nM, respectively.

FIG. 3 shows how A6 and D2 block EGF binding to EGFR expressed on the surface of A431 cells with an $IC_{50}$ of 2.06 nM and 1.35 nM, respectively.

FIG. 4a shows EGF-mediated A431 cell proliferation at 10 ng/ml EGF. The newly disclosed anti-EGFR antibody A6 was compared to cetuximab (Erbitux®), a marketed anti-EGFR antibody. A6 shows comparable efficacy to cetuximab in this in vitro model.

FIG. 4b shows EGF- and serum-stimulated MCF7 breast cancer cell proliferation at 10 ng/ml EGF or 10% FBS. The newly disclosed anti-EGFR antibody A6 was compared to cetuximab, a marketed anti-EGFR antibody. A6 shows comparable efficacy to cetuximab in this in vitro model.

FIG. 5 shows EGF-stimulated, auto-phosphorylation of the EGF Receptor in A431 epidermoid carcinoma cells. Various anti-EGFR antibodies were compared at an antibody concentration of 10 μg/ml and all show superior antagonistic effects compared to cetuximab, a marketed anti-EGFR antibody.

FIG. 6a shows the inhibition of EGFR-mediated cell signaling by anti-EGFR antibodies. Specifically, the antagonism of ERK1/2 activation by phosphorylation is shown in A431 cells.

FIG. 6b shows the inhibition of EGFR-mediated cell signaling by anti-EGFR antibodies. Specifically, the antagonism of AKT activation by phosphorylation is shown in A431 cells.

FIG. 6c shows the inhibition of EGFR-mediated cell signaling by anti-EGFR antibodies. Specifically, the antagonism of ERK1/2 activation by phosphorylation is shown in MCF7 cells.

FIGS. 16A and B show a determination of Antibody-dependent Cell Cytotoxicity (ADCC) potential for anti-EGFR antibodies as a function of antibody concentrations on a log scale. This luciferase-based promoter assay shows increasing relative light units (RLU) with increasing antibody concentration indicating a positive correlation. (FIG. 16A). The anti-EGFR mAb A6 activated ADCC with an $EC_{50}$ of 60 pM. (FIG. 16B). The anti-EGFR mAb D2 activated ADCC with an $EC_{50}$ of 200 pM.

DETAILED DESCRIPTION

Figure 7:
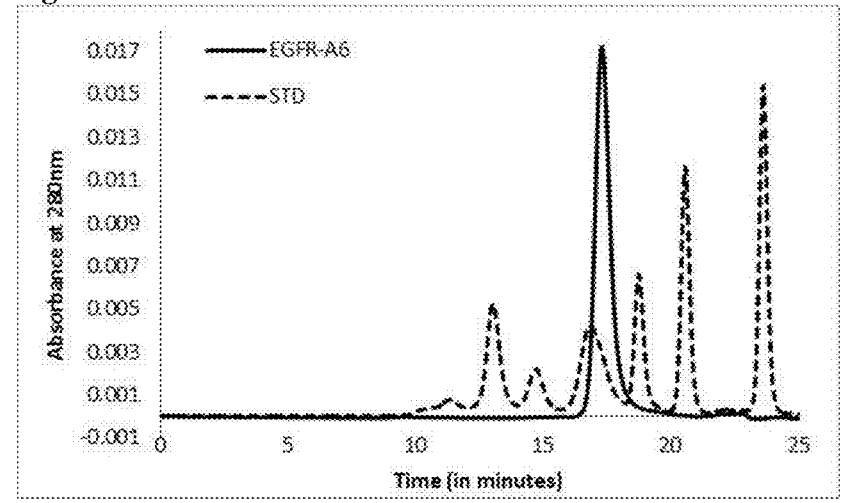
FIG. 7 shows overlaid ANSEC chromatograms (Ultra Violet trace at 280 nm) of disclosed anti-EGFR antibody A6 and standard in PBS buffer at pH 6.8: STD/standard run (black square dot), EGFR-A6 spectrum (black solid).

The present disclosure provides a fully human antibody of an IgG class that binds to an EGFR epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A3 herein), SEQ ID NO. 3/SEQ ID NO. 4 (called A2 herein), SEQ ID NO. 5/SEQ ID NO. 6 (called A6 herein), SEQ ID NO. 7/SEQ ID NO. 8 (called A10 herein), SEQ ID NO. 9/SEQ ID NO. 10 (called A11 herein), SEQ ID NO. 11/SEQ ID NO. 12 (called B1 herein), SEQ ID NO. 13/SEQ ID NO. 14 (called B4 herein), SEQ ID NO. 15/SEQ ID NO. 16 (called B5 herein), SEQ ID NO. 17/SEQ ID NO. 18 (called B6 herein), SEQ ID NO. 19/SEQ ID NO. 20 (called B7 or H3 herein), SEQ ID NO. 21/SEQ ID NO. 22 (called D2 herein), SEQ ID NO. 23/SEQ ID NO. 24 (called D4 or H9 herein), SEQ ID NO. 25/SEQ ID NO. 26 (called D6 herein), SEQ ID NO. 27/SEQ ID NO. 28 (called D10 herein), SEQ ID NO. 29/SEQ ID NO. 30 (called E-1 herein), SEQ ID NO. 31/SEQ ID NO. 32 (called EG-A4 herein), SEQ ID NO. 33/SEQ ID NO. 34 (called EG-B7 herein), SEQ ID NO. 35/SEQ ID NO. 36 (called EG-C9 herein), SEQ ID NO. 37/SEQ ID NO. 38 (called EG-D5 herein), SEQ ID NO. 39/SEQ ID NO. 40 (called EG-E9 herein), SEQ ID NO. 41/SEQ ID NO. 42 (called EG-E11 herein), SEQ ID NO. 43/SEQ ID NO. 44 (called EB8 herein), SEQ ID NO. 45/SEQ ID NO. 46 (called EC6 herein), SEQ ID NO. 47/SEQ ID NO. 48 (called EC10 herein), SEQ ID NO. 49/SEQ ID NO. 50 (called ED10 herein), SEQ ID NO. 51/SEQ ID NO. 52 (called EE12 herein), SEQ ID NO. 53/SEQ ID NO. 54 (called RE-A1 herein), SEQ ID NO. 55/SEQ ID NO. 56 (called RE-F3 herein), SEQ ID NO. 57/SEQ ID NO. 58 (called RE-F4 herein), SEQ ID NO. 59/SEQ ID NO. 60 (called G3 herein), SEQ ID NO. 61/SEQ ID NO. 62 (called A6-A1 herein), SEQ ID NO. 63/SEQ ID NO. 64 (called A6-A3 herein), SEQ ID NO. 65/SEQ ID NO. 66 (called A6-A4 herein), SEQ ID NO. 67/SEQ ID NO. 68 (called A6-A5 herein), SEQ ID NO. 69/SEQ ID NO. 70 (called A6-A6 herein), SEQ ID NO. 71/SEQ ID NO. 72 (called A6-A7 herein), SEQ ID NO. 73/SEQ ID NO. 74 (called A6-A8 herein), SEQ ID NO. 75/SEQ ID NO. 76 (called D2GA1 herein), SEQ ID NO. 77/SEQ ID NO. 78 (called D2GA2 herein), SEQ ID NO. 79/SEQ ID NO. 80 (called D2GA4 herein), SEQ ID NO. 81/SEQ ID NO. 82 (called D2GA5 herein), SEQ ID NO. 83/SEQ ID NO. 84 (called A6-A11 herein), SEQ ID NO. 85/SEQ ID NO. 86 (called A6-A12 herein), SEQ ID NO. 87/SEQ ID NO. 88 (called A6-A13 herein), SEQ ID NO. 89/SEQ ID NO. 90 (called A6-A14 herein), SEQ ID NO. 91/SEQ ID NO. 92 (called A6-A15 herein), SEQ ID NO. 93/SEQ ID NO. 94 (called A6-A17 herein), SEQ ID NO. 95/SEQ ID NO. 96 (called A6-A18 herein), SEQ ID NO. 97/SEQ ID NO. 98 (called A6-A20 herein), SEQ ID NO. 99/SEQ ID NO. 100 (called A6-A21 herein), SEQ ID NO. 101/SEQ ID NO. 102 (called A6-A22 herein), SEQ ID NO. 103/SEQ ID NO. 104 (called A6-A23 herein), SEQ ID NO. 105/SEQ ID NO. 106 (called A6-A24 herein), SEQ ID NO. 107/SEQ ID NO. 108 (called D2GA6 herein), SEQ ID NO. 109/SEQ ID NO. 110 (called D2GA9 herein), SEQ ID NO. 111/SEQ ID NO. 112 (called D2GA10 herein), SEQ ID NO. 113/SEQ ID NO. 114 (called D2GA11 herein), SEQ ID NO. 115/SEQ ID NO. 116 (called D2 GB2 herein), SEQ ID NO. 117/SEQ ID NO. 118 (called D2 GB6 herein), SEQ ID NO. 1119/SEQ ID NO. 120 (called D2 GB7 herein), SEQ ID NO. 121/SEQ ID NO. 122 (called D2 GB8 herein), SEQ ID NO. 123/SEQ ID NO. 124 (called D2GC1 herein), SEQ ID NO. 125/SEQ ID NO. 126 (called D2GC4 herein), SEQ ID NO. 127/SEQ ID NO. 128 (called D2GG1 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof.

Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

The present disclosure further provides a method for treating a broad spectrum of mammalian cancers, comprising administering an effective amount of an anti-EGFR polypeptide, wherein the anti-EGFR polypeptide is selected from the group consisting of a fully human antibody of an IgG class that binds to an EGFR epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 59, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 1119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, and combinations thereof.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present invention can be produced using any standard methods. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation.

The recombinant DNA can also include any type of protein tag sequence that may be useful for purifying the protein. Examples of protein tags include but are not limited to a poly-histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology,* 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

The polypeptide can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See, e.g., Raju et al. *Biochemistry.* 2001 31; 40(30): 8868-76. Effects of such non-amino acid elements on the functionality of a polypeptide may be tested for its antagonizing role of EGFR or EGF function, e.g., its inhibitory effect on tumor growth.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. Examples of the modified polypeptide include PEGylated A6.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

A variety of molecular mass forms of PEG can be selected, e.g., from about 1,000 Daltons (Da) to 100,000 Da (n is 20 to 2300), for conjugating to EGFR binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the invention, an EGFR binding polypeptide is covalently linked to one poly(ethylene glycol) group of the formula: —CO—(CH$_2$)$_x$—(OCH$_2$CH$_2$)$_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's δ-amino group of a lysine is the available (free) amino group.

The above conjugates may be more specifically presented by formula (II): P—NHCO—(CH$_2$)$_x$—(OCH$_2$CH$_2$)$_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254,12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication No. 2002/0044921 and in WO094/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., Bioconjug. Chem. 2004; 15(5):1005-1009.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri-poly- and un-pegylated binding polypeptide, as well as free PEG. The percentage of mono-PEG conjugates can be controlled by pooling broader fractions around the elution peak to increase the percentage of mono-PEG in the composition. About ninety percent of mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70% least 80%, 85%, 90%, 95% or 100% of the biological activity associated with the unmodified protein. In one embodiment, biological activity refers to its ability to bind to EGFR, as assessed by KD, $k_{on}$ or $k_{off}$. In one specific embodiment, the pegylated binding polypeptide protein shows an increase in binding to VEGFR relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t.sub.1/2) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Formulations and Modes of Administration

The present disclosure features methods for treating conditions or preventing pre-conditions which respond to an inhibition of EGF biological activity. Preferred examples are conditions that are characterized by tumor growth. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 μg/kg to about 50 mg/kg per day, preferably 0.01 mg/kg to about 30 mg/kg per day, and most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

Exemplary Uses

The EGFR binding proteins described herein and their related variants are useful in a number of therapeutic and diagnostic applications. These include the inhibition of the biological activity of VEGF by competing for or blocking the binding to an EGFR.

On the basis of their efficacy as inhibitors of VEGF biological activity, the polypeptides of the invention are effective against a number of conditions associated with inflammatory diseases and tumor growth, including but not limited to autoimmune disorders (e.g., rheumatoid arthritis, inflammatory bowel disease or psoriasis); cardiac disorders (e.g., atherosclerosis or blood vessel restenosis); retinopathies (e.g., proliferative retinopathies generally, diabetic retinopathy, age-related macular degeneration or neovascular glaucoma), renal disease (e.g., diabetic nephropathy, malignant nephrosclerosis, thrombotic microangiopathy syndromes; transplant rejection; inflammatory renal disease; glomerulonephritis; mesangioproliferative glomerulonephritis; haemolytic-uraemic syndrome; and hypertensive nephrosclerosis); hemangioblastoma; hemangiomas; thyroid hyperplasias; tissue transplantations; chronic inflammation; Meigs's syndrome; pericardial effusion; pleural effusion; autoimmune diseases; diabetes; endometriosis; chronic asthma; undesirable fibrosis (particularly hepatic fibrosis) and cancer, as well as complications arising from cancer, such as pleural effusion and ascites. Preferably, the EGFR-binding polypeptides of the invention can be used for the treatment or prevention of hyperproliferative diseases or cancer and the metastatic spread of cancers. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer. Additional treatable conditions can be found in U.S. Pat. No. 6,524,583, incorporated by reference herein. Other references describing uses for EGFR binding polypeptides include: McLeod et al., Invest. *Ophthalmol. Vis. Sci.* 2002; 43(2):474-82; Watanabe et al., *Exp. Dermatol.* 2004; 13(11): 671-81; Yoshiji et al., *Gut.* 2003 52(9):1347-54; Verheul et al., *Oncologist.* 2000; 5 Suppl 1:45-50; and Boldicke et al., *Stem Cells.* 2001 19(1):24-36.

As described herein, cancers include, but are not limited to, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

AN EGFR binding polypeptide can be administered alone or in combination with one or more additional therapies such as chemotherapy, radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer.

In certain embodiments, the subject anti-EGFR antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds has been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

The EGFR binding proteins described herein can also be detectably labeled and used to contact cells expressing EGFR for imaging applications or diagnostic applications. For diagnostic purposes, the polypeptide of the invention is preferably immobilized on a solid support. Preferred solid supports include columns (for example, affinity columns, such as agarose-based affinity columns), microchips, or beads.

In one example of a diagnostic application, a biological sample, such as serum or a tissue biopsy, from a patient suspected of having a cancer is contacted with a detectably labeled polypeptide of the invention to detect levels of EGFR. The levels of EGFR detected are then compared to levels of EGFR detected in a normal sample also contacted with the labeled polypeptide. An increase of at least 10%, 20%, 30%, 40%, 50%, 60%, 70%, 80%, or 90% in the levels of the EGFR may be considered a diagnostic indicator of a condition characterized by cancer.

In certain embodiments, the EGFR binding polypeptides of the invention are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radio scintigraphy, nuclear magnetic resonance imaging, computed tomography or positron emission tomography. Immunoscintigraphy using EGFR binding polypeptides directed at EGFR may be used to detect and/or diagnose cancers and vasculature. For example, any of the binding polypeptide against the EGFR marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically a person skilled in the art administers 0.1-100 millicuries per dose of imaging agent, preferably 1-10 millicuries, most often 2-5 millicuries. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The EGFR binding polypeptides can also be used to deliver additional therapeutic agents (including but not limited to drug compounds, chemotherapeutic compounds, and radiotherapeutic compounds) to a cell or tissue expressing EGFR. In one example, the EGFR binding polypeptide is fused to a chemotherapeutic agent for targeted delivery of the chemotherapeutic agent to a tumor cell or tissue expressing EGFR.

The EGFR binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of EGFR, for example, on endothelial cells (e.g., venous endothelial cells), or on cells transfected with an EGFR gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to EGFR. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising an EGFR protein is combined with the subject binding polypeptides, binding occurs between the binding polypeptides and the EGFR protein. In one embodiment, a sample containing cells expressing an EGFR protein (e.g., endothelial cells) is combined with the subject antibodies, and binding occurs between the binding polypeptides and cells bearing an EGFR protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of an EGFR protein in a biological sample can also be prepared. Such kits will include an EGFR binding polypeptide which binds to an EGFR protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of EGFR, wherein a composition comprising a cell or fraction thereof (e.g., membrane fraction) is contacted with a binding polypeptide which binds to an EGFR or portion of the receptor under conditions appropriate for binding thereto, and the binding is monitored. Detection of the binding polypeptide, indicative of the formation of a complex between binding polypeptide and EGFR or a portion thereof, indicates the presence of the receptor. Binding of a polypeptide to the cell can be determined by standard methods, such as those described in the working examples. The method can be used to detect expression of EGFR on cells from an individual. Optionally, a quantitative expression of EGFR on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of EGFR present on cells and/or the number of EGFR-positive cells in a mammal. In one embodiment, the invention relates to a method of detecting susceptibility of a mammal to a tumor. In this embodiment, a sample to be tested is contacted with a binding polypeptide which binds to an EGFR or portion thereof under conditions appropriate for binding thereto, wherein the sample comprises cells which express EGFR in normal individuals. The binding and/or amount of binding is detected, which indicates the susceptibility of the individual to a tumor, wherein higher levels of receptor correlate with increased susceptibility of the individual to a tumor.

The following terms, unless otherwise indicated, shall be understood to have the following meanings:

The terms "EGFR inhibitor" and "EGFR antagonist" are used interchangeably. Each is a molecule that detectably inhibits at least one function of EGFR. Conversely, a "EGFR agonist" is a molecule that detectably increases at least one function of EGFR. The inhibition caused by an EGFR inhibitor need not be complete so long as it is detectable using an assay. Any assay of a function of EGFR can be used, examples of which are provided herein. Examples of functions of EGFR that can be inhibited by an EGFR inhibitor, or increased by an EGFR agonist, include cancer cell growth or apoptosis (programmed cell death), and so on. Examples of types of EGFR inhibitors and EGFR agonists include, but are not limited to, EGFR binding polypeptides such as antigen binding proteins (e.g., EGFR inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is VK-B8, which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5.sup.th Ed., US Dept. of Health and Human Services, PHS, NIH, NIH Publication no. 91-3242, 1991. Other numbering systems for the amino acids in immunoglobulin chains include IMGT® (International ImMunoGeneTics information system; Lefranc et al., *Dev. Comp. Immunol.* 29:185-203; 2005) and AHo (Honegger and Pluckthun, *J. Mol. Biol.* 309(3):657-670; 2001).

An "antibody" refers to an intact immunoglobulin or to an antigen binding portion (Fab) thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634 and 6,696,245, the disclosures of which are incorporated by reference herein).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, *Science* 242:423-26 and Huston et al., 1988, *Proc. Natl. Acad. Sci. USA* 85:5879-83).

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified (Sequences of Proteins of Immunological Interest, 5.sup.th Ed., US Dept. of Health and Human Services, PHS, NIH, NIH Publication no. 91-3242, 1991). Other numbering systems for the amino acids in immunoglobulin chains include IMGT® (Iinternational ImMunoGeneTics information system; Lefranc et al., *Dev. Comp. Immunol.* 29:185-203; 2005) and AHo (Honegger and Pluckthun, *J. Mol. Biol.* 309(3): 657-670; 2001). One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have each and every variable and constant regions derived from human immunoglobulin sequences. In one embodiment, fully human antibody, all of the variable and constant domains are derived from human immunoglobulin sequences (a fully human antibody).

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297; 5,886,152; and 5,877,293.

The term "chimeric antibody" refers to an antibody that contains one or more regions from one antibody and one or more regions from one or more other antibodies.

Further, the framework regions may be derived from one of the same anti-EGFR antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (U.S. Pat. No. 4,816,567)

A "neutralizing antibody" or an "inhibitory antibody" is an antibody that inhibits the activation of EGFR when an excess of the anti-EGFR antibody reduces the amount of activation or inhibition by at least about 20% using an assay such as those described herein in the Examples. In various embodiments, the antigen binding protein reduces the amount of amount of activation of EGFR by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human EGFR) if it binds to the antigen with a dissociation constant of 1 nM or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to EGFR, (preferably, human EGFR). Antigen binding proteins include antigen binding proteins that inhibit a biological activity of EGFR.

Oligomers that contain one or more antigen binding proteins may be employed as EGFR antagonists. Oligomers may be in the form of covalently-linked or non-covalently-linked dimers, trimers, or higher oligomers. Oligomers comprising two or more antigen binding proteins are contemplated for use, with one example being a homodimer. Other oligomers include One embodiment is directed to a dimer comprising two fusion proteins created by fusing an EGFR binding fragment of an anti-EGFR antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-EGFR antibody fragment or derivative fused to a leucine zipper peptide are expressed in suitable host cells, and the soluble oligomeric anti-EGFR antibody fragments or derivatives that form are recovered from the culture supernatant.

The present disclosure provides an EGFR antigen binding protein (for example, an anti-EGFR antibody), that has one or more of the following characteristics: binds to both human and murine EGFR, inhibits the activation of human EGFR, inhibits the activation of murine EGFR, and binds to or near the ligand binding domain of EGFR.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to EGFR. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against EGFR can be used, for example, in assays to detect the presence of EGFR polypeptides, either in vitro or in vivo. The antigen binding proteins also may be employed in purifying EGFR proteins by immunoaffinity chromatography. Those antigen binding proteins that additionally can block ligand binding-mediated activation of EGFR may be used to inhibit a biological activity that results from such binding. Blocking antigen binding proteins can be used in the methods disclosed herein. Such antigen binding proteins that function as EGFR antagonists may be employed in treating any EGFR-induced condition, including but not limited to various cancers.

Antigen binding proteins may be employed in an in vitro procedure, or administered in vivo to inhibit an EGFR-induced biological activity. Disorders caused or exacerbated (directly or indirectly) by the activation of EGFR, examples of which are provided herein, thus may be treated. In one embodiment, the present invention provides a therapeutic method comprising in vivo administration of an EGFR blocking antigen binding protein to a mammal in need thereof in an amount effective for reducing an EGFR-induced biological activity.

Antigen binding proteins include fully human monoclonal antibodies that inhibit a biological activity of EGFR.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of EGFR bound thereto. Polypeptides contemplated for use herein include substantially homogeneous recombinant mammalian anti-EGFR antibody polypeptides substantially free of contaminating endogenous materials.

Antigen binding proteins may be prepared, and screened for desired properties, by any of a number of known techniques. Certain techniques involve isolating a nucleic acid encoding a polypeptide chain (or portion thereof) of an antigen binding protein of interest (e.g., an anti-EGFR antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for EGFR of at least $10^6$ nM. In other embodiments, the antigen binding proteins exhibit a $K_a$ of at least $10^7$, at least $10^8$, at least $10^9$, or at least $10^{10}$M. In another embodiment, the antigen binding protein exhibits a $K_a$ substantially the same as that of an antibody described herein in the Examples.

In another embodiment, the present disclosure provides an antigen binding protein that has a low dissociation rate from EGFR. In one embodiment, the antigen binding protein has a $K_{off}$ of $1\times10^{-4}$ to $1\times10^{-1}$M or lower. In another embodiment, the $K_{off}$ is $5\times10^{-5}$ to $5\times10^{-1}$M or lower. In another embodiment, the $K_{off}$ is substantially the same as an antibody described herein in the Examples. In another embodiment, the antigen binding protein binds to EGFR with substantially the same $K_{off}$ as an antibody described herein in the Examples.

In another aspect, the present disclosure provides aEGFR membrane binding protein. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of EGFR with substantially the same $IC_{50}$ as an antibody described herein in the Examples.

In another aspect, the present disclosure provides an antigen binding protein that binds to human EGFR expressed on the surface of a cell and, when so bound, inhibits EGFR signaling activity in the cell. Any method for determining or estimating the amount of EGFR on the surface and/or in the interior of the cell can be used. In other embodiments, binding of the antigen binding protein to the EGFR-expressing cell causes less than about 75%, 50%, 40%, 30%, 20%, 15%, 10%, 5%, 1%, or 0.1% of the cell-surface EGFR to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that binds to two different epitopes of EGFR, or to an epitope of EGFR and an epitope of another molecule, via two different antigen binding sites or regions. Moreover, bispecific antigen binding protein as disclosed herein can comprise an EGFR binding site from one of the herein-described antibodies and a second EGFR binding region from another of the herein-described antibodies, including those described herein by reference to other publications. Alternatively, a bispecific antigen binding protein may comprise an antigen binding site from one of the herein described antibodies and a second antigen binding site from another EGFR antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959, 083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule), a detectable bead (such as a magnetic or electrodense (e.g., gold bead), a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Example 1

Full length IgGs were purified by Protein A and their purities were exanimated by SDS-PAGE. Purified antibodies were characterized by binding specificity (to both the soluble EGFR and EGFR-expressing cell lines), binding affinity (Biacore), inhibition of EGF binding to the soluble EGFR, EGF-stimulated EGFR phosphorylation and cell proliferation in EGFR-expressing cell line. Anti-EGFR antibodies have been converted to IgGs and expressed in 293 cells. Expression level ranged from 0.86 to 5.5 µg/ml upon purification by Protein A. The antibodies had one intact heavy and light chain. Five of them (A5, A6, B1, B4 and B5) bind to soluble EGFR and EGFR expressed on cell lines strongly. One antibody (D6) showed moderate binding to both soluble EGFR and EGFR expressed cell lines. These six binders also block the ligand EGF binding to its soluble EGFR in ELISA assay.

Three binders (A5, A6 and B5) showed ~10% inhibition in EGF stimulated receptor phosphorylation assay in EGFR positive cells (A431). Three binders (B1, B4 and D6) showed inhibition in a tumor cell proliferation assay.

Example 2

This example illustrates anti-EGFR production. Anti-EGFR antibodies were produced in Chinese hamster ovary subclone S (CHO-S) cells (Life Technologies) transiently transfected with expression vectors containing anti-human EGFR IgG1 heavy and light chain structural genes.

The cell line was maintained in shake flasks and routinely passaged every 3 to 4 days using CHO-S-SFMII medium (Life Technologies). Two plasmids were used to generate the transient pool: one carrying the heavy chain and one carrying the light chain. The vectors were co-transfected into the host cell line using 25 kd linear polyethyleneimine (PEI, Polysciences).

Briefly, PEI was diluted into OptiPro SFM (Life Technologies) and then added to plasmid DNA previously diluted in an equal volume of OptiPro SFM. The PEI/DNA mix was incubated five to ten minutes and then added to CHO-S cells in suspension. The culture was incubated for a predetermined time at 37° C. and then expanded with an equal volume of expansion media. The culture supernatant was harvested several days later and concentrated in preparation for purification.

Example 3

This example illustrates in vitro data for cell binding as part of an initial screen for several disclosed antibodies, including A6. This example demonstrates the ability of anti-EGFR antibodies to bind the EGF Receptor expressed on the surface of A431 cells compared to the commercially available cetuximab (Erbitux®), which is requisite for antagonistic properties of the antibodies. Here, 100,000 A431 cells were aliquoted into tubes in 100 µl FACS Buffer (PBS+2% FBS). Cells were spun down and then resuspended in 100 µl of FACS Buffer plus 5 µg/ml of the indicated antibody in triplicate. After 0.5 hr incubation, cells were washed 1× with FACS Buffer and resuspended in 100 µl PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in 300 µl FACS Buffer and the median fluorescence intensity in the FL2-H channel was determined using the FACS Aria flow cytometer (BD). The median fluorescence intensity in the FL2-H channel is directly proportional to the antibody binding to the cell surface EGFR.

Results: FIG. 1 shows that cell binding for the anti-EGFR antibodies on A431 cells was strong compared to background staining (control, No Ab). The histograms depict the number events with specific fluorescence intensities. All the antibodies had extremely strong cell binding which was comparable to cetuximab. Data shown is one of three replicates and is representative of multiple experiments.

Example 4

This example illustrates in vitro data for A6 and D2 cellular binding $EC_{50}$ measurements. This example shows the binding characteristic for these antibodies in terms of the maximal cell binding and the concentration at which 50% binding saturation ($EC_{50}$) is reached. In this example, the anti-EGFR antibodies, A6 and D2, are compared to the commercially-available therapeutic anti-EGFR antibody, cetuximab. In this example, the experimental procedure was as follows: 50,000 A431 cells were aliquoted into the wells of a 96-well, v-bottom plate in 100 ul FACS Buffer (PBS+2% FBS). A twelve point, 3× dilution curve of A6, D2, and cetuximab was made in FACS Buffer starting at 50 µg/ml ($3.33 \times 10^{-7}$M). Cells were spun down, washed 1× with FACS Buffer, and then resuspended in 25 µl of antibody solution in triplicate. After 0.5 hr incubation, cells were washed 1× with FACS Buffer and resuspended in 50 µl PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in 25 ul FACS Buffer and the median fluorescence intensity in the FL2-H channel was determined using the Intellicyt HTFC flow cytometer.

Results: As shown in FIG. 2, the cell binding $EC_{50}$ for A6, D2, and cetuximab on A431 cells was determined to be 1.3 nM, 0.28 nM, and 0.48 nM, respectively. Data was analyzed and plotted in Graph Pad Prizm using non-linear regression fit. Data points are shown as the median fluorescence intensity (MFI) of positively labeled cells+/−Std Error.

Example 5

This example illustrates in vitro data showing the blocking of EGF binding to the EGF Receptor on the surface of A431 cells by the Anti-EGFR antibodies A6, D2, and others. The anti-EGFR antibodies were compared directly to cetuximab. The ability of an antibody to block the binding of EGF to EGFR would demonstrate the potential for this antibody to inhibit the function of EGFR in cancer cells. To show this, 25,000 A431 cells were incubated in PBS-BSA 1% with serial dilutions of anti-EGFR antibodies for 30 min at 4° C. Then 1 µl of Human EGF Biotinylated Fluorokine (R&D Systems catalog #NFEG0) was added in each well. After a 45 min incubation at 4° C., the manufacturer's protocol for EGF detection was followed, scaled down for use in a micro-titer plate. Cells were finally resuspended in 25 µl FACS Buffer and the median fluorescence intensity in the FL1-H channel was determined using an Intellicyt HTFC flow cytometer. Intensity of FL1-H signal is directly proportional to the binding of EGF to the cell surface of the cells. A decrease in signal indicates blocking of EGF binding. Data was analyzed and plotted in Graph Pad Prizm using non-linear regression fit. Data points are shown as the median fluorescence intensity (MFI)+/−Std Error.

Results: As shown in FIG. 3, the presence of anti-EGFR antibodies blocks the binding of EGF to the surface of EGFR-expressing A431 cells. The $IC_{50}$ values for A6 and D2 were 2.06 nM and 1.35 nM, respectively. These values are equal to or better than cetuximab, which had an $IC_{50}$ value of 2.03 nM.

Example 6

This example illustrates in vitro data showing the inhibition of EGF- or Serum-stimulated cell proliferation by anti-EGFR antibodies versus FDA approved anti-EGFR cetuximab. Uncontrolled cell proliferation is a hallmark of cancer and the ability to inhibit proliferation in EGFR positive cancer cells with anti-EGFR antibodies is requisite for a therapeutic compound. In this example, 5000 A431 epidermoid carcinoma cells (FIG. 4a) or MCF7 breast cancer cells (FIG. 4b) were plated into the wells of a 96-well white opaque cell culture cluster in 100 DMEM media (A431 cells) or Phenol Red-free DMEM (MCF7) supplemented with 10% FBS, in triplicate. 24 hours later, media was removed, cells were washed 1× with PBS, and then starved for 18 hr in 100 µl media without FBS (starvation media). In FIG. 4a, antibodies were diluted to 2× the desired treatment concentration (20 ng/µl or 10 ng/µl) in 50 µl starvation media, and added to the cells after removal of the starvation media. After 1 hr incubation, EGF was added at a concentration of 20 ng/ml in 50 ul (final concentration of EGF was 10 ng/ml). Cells were then incubated for 48 hr, after which the Promega Cell Titer Glo kit was used to evaluate proliferation. Luminescence output was directly proportional to cell number. In FIG. 4b, antibodies were diluted to 2× the desired treatment concentration (20 ng/µl) in 50 µl starvation media, and added to the cells after removal of the starvation media. After 1 hr incubation, EGF or FBS was added at a concentration of 20 ng/ml or 20% respectively, in 50 µl starvation media (final concentration of EGF was 10 ng/ml; final concentration of FBS was 10%). Cells were then incubated for 48 hr after which the Promega Cell Titer Glo kit was used to evaluate proliferation. Luminescence output is directly proportional to cell number.

Results: The disclosed anti-EGFR antibody A6 inhibited EGF-stimulated A431 proliferation (FIG. 4a) and both EGF-stimulated and Serum-stimulated MCF7 proliferation (FIG. 4b). Proliferation inhibition was similar to that conferred by cetuximab at the same dose for all treatment conditions. Data shown is the mean relative light units of triplicate samples+/−Std Error.

Example 7

This example illustrates in vitro data showing EGF stimulated auto-phosphorylation of the EGF receptor in A431 cells. This example demonstrates the ability of antibodies to block the activation of and therefore the function of EGFR in cancer cells. Protocol: 500,000 A431 cells were plated in the wells of a 6-well cell culture cluster in 2.5 ml DMEM media supplemented with 10% FBS. 24 hr later, media were removed and the cells washed 1× with PBS, and then starved for 18 hr in 1 ml starvation media (DMEM+2% FBS). Antibodies were diluted to 20 µg/ml (2× final concentration) in 1 ml serum-free media, then added to the cells after removal of starvation media. After 0.5 hr incubation, EGF was added to a final concentration of 100 ng/ml. Cells were then incubated for 60 min. Cells were washed with PBS and lysed in 1× Cell Lysis Buffer (Cell Signaling). Phosphorylation of EGFR was detected using sandwich ELISA as follows: Half area 96-well micro-titer plates were coated with anti-EGFR antibody (1:100 in PBS; Cell Signaling cat #2232) overnight at 4° C. After washing 4× with PBST, wells were blocked with 100 µl PBST+1% BSA for 2 hr at 37° C. Plates were washed again, then 50 µl lysate was added to wells and incubated for a further 2 hr at 37° C. Following another wash, an anti-phospho-tyrosine antibody (mAB 9E10) conjugated to biotin was added (1:100 in blocking buffer; 50 µl per well). Plates were incubated for 1 hr at 37° C. Another wash step is followed by incubation with an Anti-Biotin HRP labeled antibody (Upstate) for 30 min at 37° C. The final was step is followed by incubation with 50 µl TMB substrate for 10 min at 37° C. The reaction is stopped using 2N $H_2SO_4$. The OD 450 nm was read and the percent inhibition was calculated as $1-(OD_{450}$ of antibody treated sample/$OD_{450}$ untreated control).

Results: A431 cells were treated with 100 ng/ml EGF to stimulate activating auto-phosphorylation of EGFR. Pre-treatment of cells with anti-EGFR antibodies variably blocked this activation of EGFR. All of the clones examined showed greater inhibition of EGFR auto-phosphorylation than cetuximab (Erbitux®) (FIG. 5) indicating these clones are candidates for therapeutic intervention against EGFR in cancer indications. Data shown is representative of multiple experiments and is expressed in percent inhibition of EGFR auto-phosphorylation calculated as 1 $OD_{450}$ of antibody treated sample/$OD_{450}$ untreated control) of triplicate samples+/−Std Error.

Example 8

This example illustrates in vitro data showing the inhibition of cellular signaling when antibodies are used to block EGFR function. Specifically, blocking of EGFR activation by its ligand EGF, blocks the activation of kinase cascades that would lead to the activation of molecules such as ERK (extracellular signal regulated kinase; a MAPK) and AKT (also known as Protein Kinase B), which are responsible for growth and survival signals in the cells. FIGS. 6a and c show the inhibition of Erk1/2 activation (inhibition of activating phosphorylation) in A431 and MCF7 cells, respectively, by anti-EGFR antibodies. FIG. 6b shows the inhibition of AKT activation (inhibition of activating phosphorylation) by anti-EGFR antibodies in A431 cells. In this example, serum starved cells were pretreated for 2 hr with or without 10 µg/ml anti-EGFR antibody followed by stimulation with 10 ng/ml EGF for 1 hr (MCF7 cells were co-stimulated with 100 ng/ml TGFα). Cells were then washed and processed for staining with P-ERK1/2 or P-AKT antibodies (Cell Signaling catalog #5682 or #4071) according to manufacturer's protocol. The extent of antibody staining detected by flow cytometry was proportional to the phosphorylation of the signaling molecule and therefore to its activation. FIG. 6a shows the median fluorescence intensity indicative of the level of activation of ERK1/2. FIGS. 6b and 6c shows the percent inhibition of phosphorylation compared to control. In this example, anti-EGFR antibodies were compared to cetuximab for the ability to inhibit EGF-stimulated cellular signaling.

Results: FIG. 6a shows the level of phosphorylation of ERK1/2 in A431 cells treated with or without antibodies against EGFR and with or without EGF. In this case, all antibodies showed an inhibition of ERK activation indicated by decreased MFI compared to the control treated with EGF but not with antibody. The A6 antibody shows equal inhibition of ERK1/2 activation compared to cetuximab. Data are shown as the median fluorescence intensity and is representative of multiple experiments.

FIG. 6b shows the inhibition of AKT phosphorylation (activation) in A431 cells treated with anti-EGFR antibodies and stimulated with EGF. Percent inhibition was calculated as 1−(MFI of antibody treated sample/MFI of non-specific IgG treated control). The data indicate that the EGFR antibodies can block the activation of AKT, but not as potently as cetuximab. Data shown are representative of multiple experiments.

FIG. 6c shows the inhibition of ERK1/2 phosphorylation (activation) in MCF7 cells treated with anti-EGFR antibodies and stimulated with EGF. Percent inhibition was calculated as 1−(MFI of antibody treated sample/MFI of non-specific IgG treated control). The data indicates that the EGFR antibodies are extremely potent inhibitors of ERK activation in MCF7 breast cancer cells. The exemplary antibody, A6, showed extremely potent inhibition of ERK activation, greater than 60% inhibition, that is superior to Erbitux. Data shown are representative of multiple experiments.

Example 9

This example provides an ANSEC (Water's Breeze-HPLC) analysis of EGFR monoclonal antibodies. The analysis was performed in PBS buffer, pH 6.8 at 0.5 mL/min flow rate using BioSep-SEC-s3000, 300×7.8 mm column (Phenomenex). Each EGFR monoclonal antibody sample was compared with the BIO-RAD gel filtration protein standard (STD; Cat #, 151-1901-Thyroglobi=670 KDa; Gamma-globulin=158 KDa; Ovalbumin=44 KDa; Myoglobin=17 KDa; Vitamin B12=1.35 KDa) under the identical running conditions.

Figure 8:
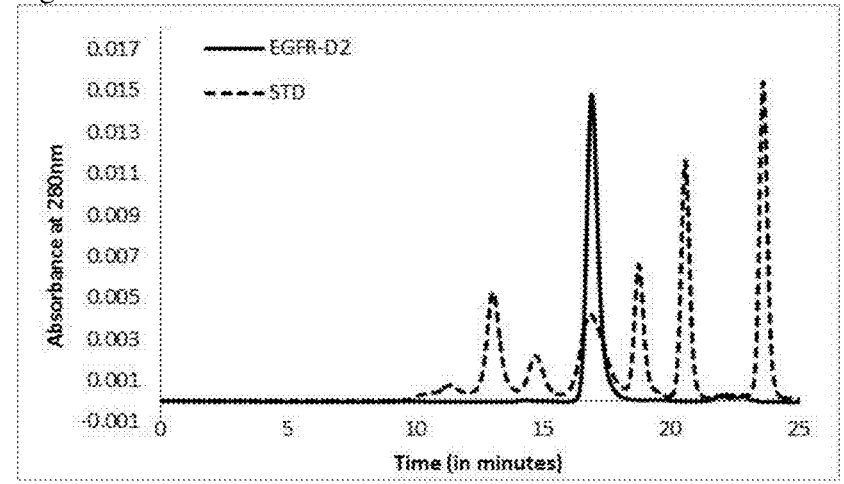
FIG. 8 shows overlaid ANSEC chromatograms (Ultra Violet trace at 280 nm) of disclosed anti-EGFR antibody D2 and standard in PBS buffer at pH 6.8: STD/standard run (black square dot), EGFR-D2 spectrum (black solid).
Figure 9:
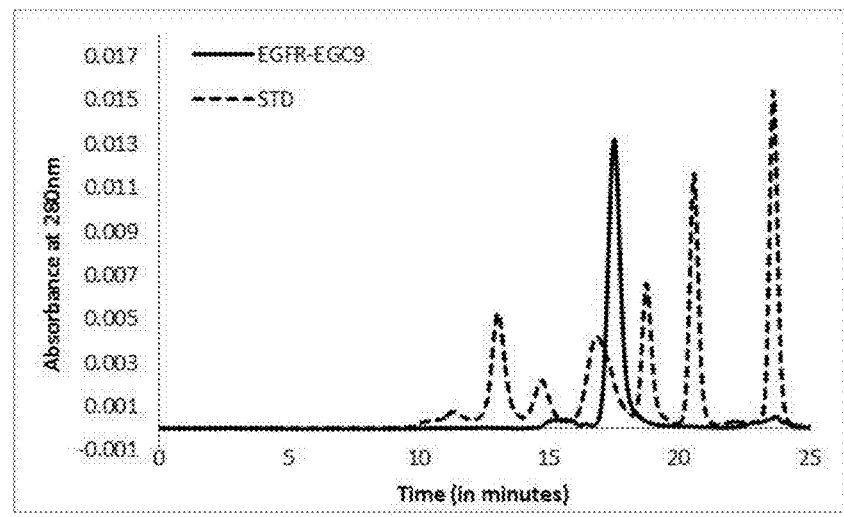
FIG. 9 shows overlaid ANSEC chromatograms (Ultra Violet trace at 280 nm) of disclosed anti-EGFR antibody EGC9 and standard in PBS buffer at pH 6.8: STD/standard run (black square dot), EGFR-EGC9 spectrum (black solid).
Figure 10:
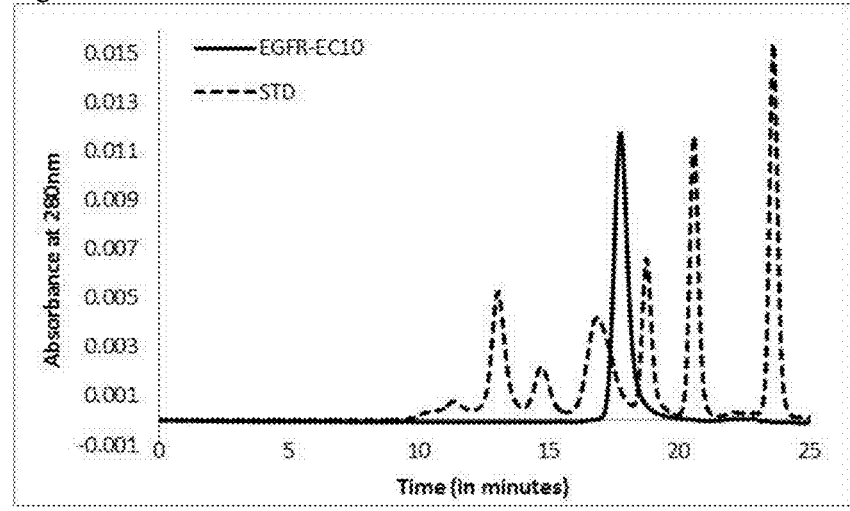
FIG. 10 shows overlaid ANSEC chromatograms (Ultra Violet trace at 280 nm) of disclosed anti-EGFR antibody EC10 and standard in PBS buffer at pH 6.8: STD/standard run (black square dot), EGFR-EC10 spectrum (black solid).
Figure 11:
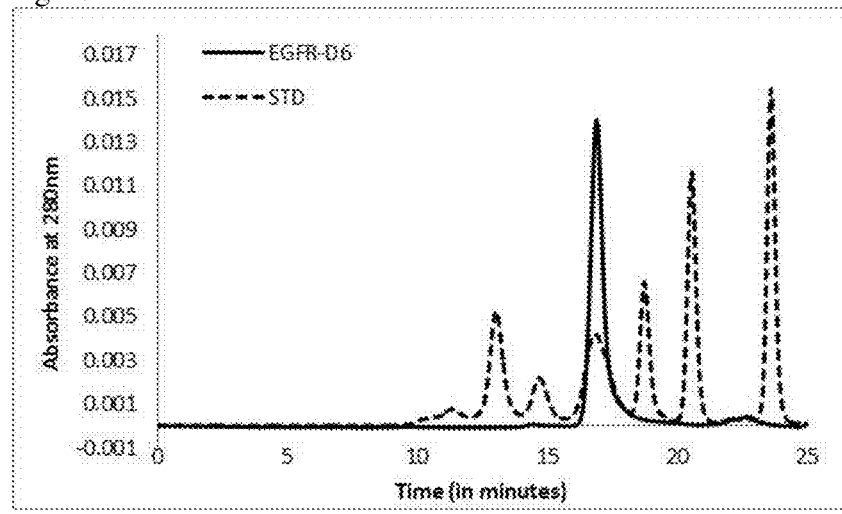
FIG. 11 shows overlaid ANSEC chromatograms (Ultra Violet trace at 280 nm) of disclosed anti-EGFR antibody D6 and standard in PBS buffer at pH 6.8: STD/standard run (black square dot), EGFR-D6 spectrum (black solid).
Figure 12:
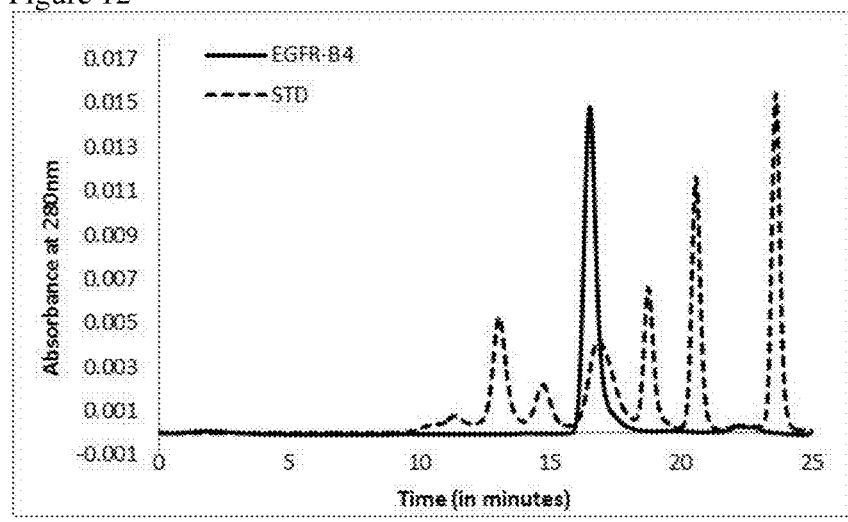
FIG. 12 shows overlaid ANSEC chromatograms (Ultra Violet trace at 280 nm) of disclosed anti-EGFR antibody B4 and standard in PBS buffer at pH 6.8: STD/standard run (black square dot), EGFR-B4 spectrum (black solid).
Figure 13:
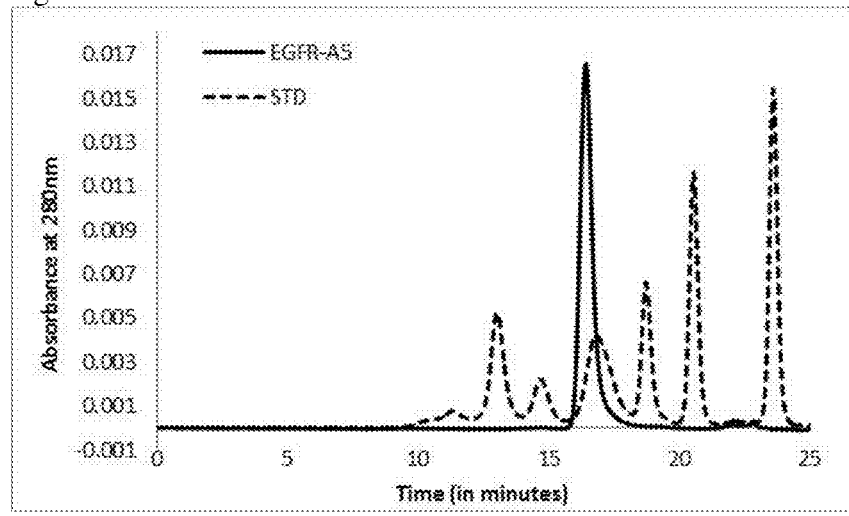
FIG. 13 shows overlaid ANSEC chromatograms (Ultra Violet trace at 280 nm) of disclosed anti-EGFR antibody A5 and standard in PBS buffer at pH 6.8: STD/standard run (black square dot), EGFR-A5 spectrum (black solid).

FIG. 7 shows overlaid ANSEC chromatograms (Ultra Violet trace at 280 nm) of disclosed anti-EGFR antibody A6 and standard in PBS buffer at pH 6.8: STD/standard run (black square dot), EGFR-A6 spectrum (black solid). FIG. 8 shows overlaid ANSEC chromatograms (Ultra Violet trace at 280 nm) of disclosed anti-EGFR antibody D2 and standard in PBS buffer at pH 6.8: STD/standard run (black square dot), EGFR-D2 spectrum (black solid). FIG. 9 shows overlaid ANSEC chromatograms (Ultra Violet trace at 280 nm) of disclosed anti-EGFR antibody EGC9 and standard in PBS buffer at pH 6.8: STD/standard run (black square dot), EGFR-EGC9 spectrum (black solid). FIG. 10 shows overlaid ANSEC chromatograms (Ultra Violet trace at 280 nm) of disclosed anti-EGFR antibody EC10 and standard in PBS buffer at pH 6.8: STD/standard run (black square dot), EGFR-EC10 spectrum (black solid). FIG. 11 shows overlaid ANSEC chromatograms (Ultra Violet trace at 280 nm) of disclosed anti-EGFR antibody D6 and standard in PBS buffer at pH 6.8: STD/standard run (black square dot), EGFR-D6 spectrum (black solid). FIG. 12 shows overlaid ANSEC chromatograms (Ultra Violet trace at 280 nm) of disclosed anti-EGFR antibody B4 and standard in PBS buffer at pH 6.8: STD/standard run (black square dot), EGFR-B4 spectrum (black solid). FIG. 13 shows overlaid ANSEC chromatograms (Ultra Violet trace at 280 nm) of disclosed anti-EGFR antibody A5 and standard in PBS buffer at pH 6.8: STD/standard run (black square dot), EGFR-A5 spectrum (black solid).

Example 10

This example shows the effect of anti-EGFR antibodies on tumor growth in vivo. The ability of anti-EGFR antibodies to modulate tumor growth was assessed using an athymic murine model. Briefly, groups of five mice were injected subcutaneously in the flank with $5 \times 10^6$ A431 human epidermoid carcinoma cells. Once tumors had reached an approximate volume of 100 mm$^3$ the mice were treated intraperitoneally at 10 mg/kg with 200 ml of i) PBS, ii) antibody A6 (0.2 mg), iii) antibody D2 (0.2 mg), or iv) a combination of antibodies A6 (0.1 mg) and D2 (0.1 mg) to give a total of 0.2 mg of protein. Treatments were performed three times per week until the termination of the experiment.

Figure 14:
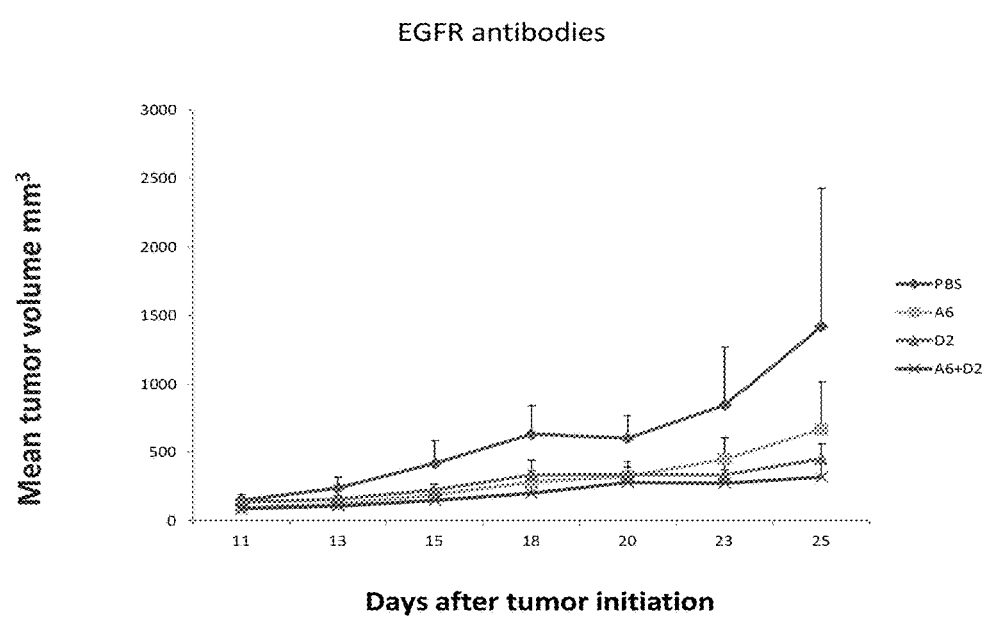
FIG. 14 shows that both A6 (squares) and D2 (triangles) antibodies reduced the growth of the xenogeneic tumor cells in vivo.

As shown in FIG. 14, both A6 (squares) and D2 (triangles) antibodies reduced the growth of the xenogeneic tumor cells in vivo.

Example 11

This example illustrates in vitro data showing the inhibition of EGF stimulated auto-phosphorylation of the EGF receptor in A549 Non-Small Cell Lung Cancer cells. This example demonstrates the ability of antibodies to block the activation of and therefore the function of EGFR in cancer cells. Briefly, 10,000 A549 cells were plated in the wells of a 96-well cell culture cluster in 100 µl F12-K media supplemented with 10% FBS. 24 hr later, media were removed and the cells washed 1× with PBS, and then starved for 18 hr in 100 µl starvation media (serum-free F12-K). Serial dilutions of the antibodies were made in serum-free media at 2× final concentration, then added to the cells after removal of starvation media. After 15 min incubation, EGF was added to a final concentration of 25 ng/ml. Cells were then incubated for 5 min. Cells were washed with PBS plus sodium orthovanadate and lysed. Phosphorylation of EGFR was detected using the DuoSet IC Human Phospho-EGFR ELISA kit from R&D Systems (#DYC1095B).

Figure 15:
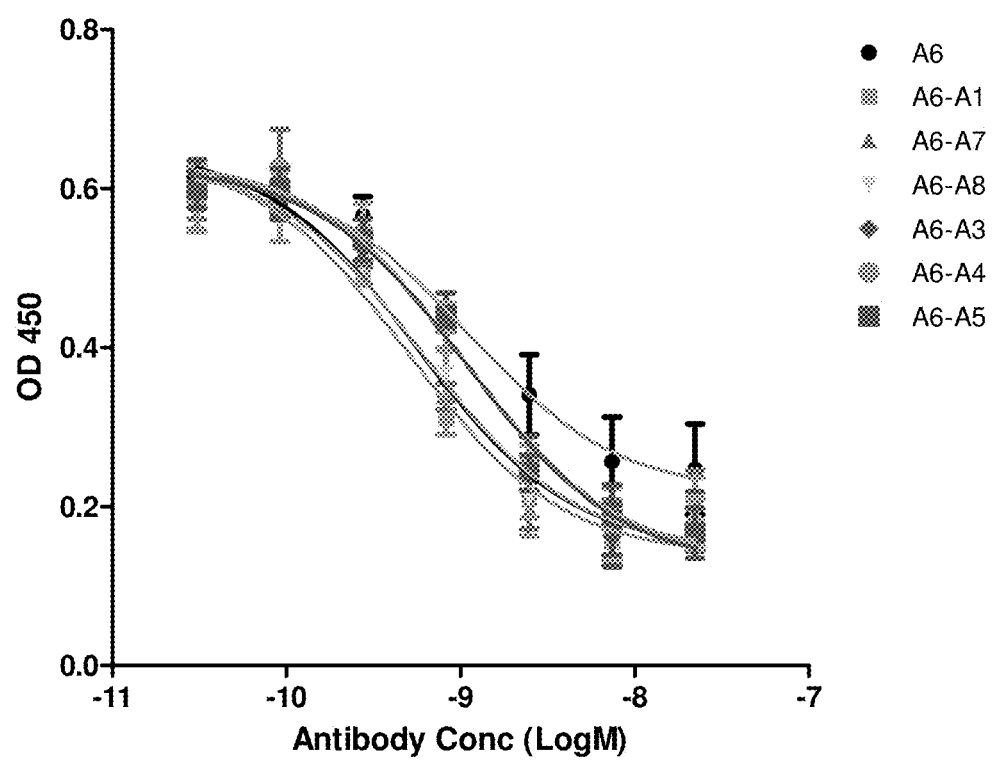
FIG. 15 shows $IC_{50}$ determinations of various variants of the A6 antibody for the inhibition of EGFR activation by auto-phosphorylation induced by EGF treatment.
Figure 17:
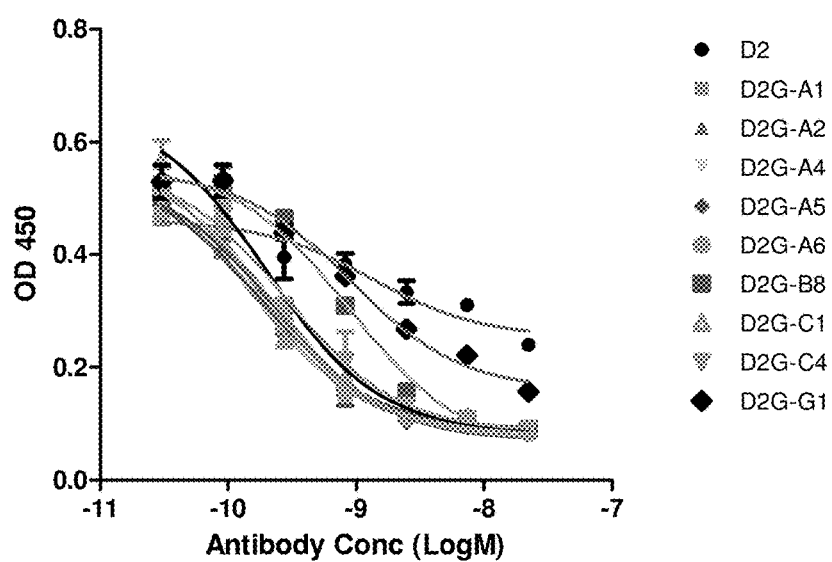
FIG. 17 shows $IC_{50}$ determinations of various variants of the D2 antibody for the inhibition of EGFR activation by auto-phosphorylation induced by EGF treatment.

Pre-treatment of A549 cells with anti-EGFR antibodies variably blocked the phosphorylation and activation of EGFR by EGF. A) Clone A6 and affinity matured variants show IC$_{50}$ for this effect ranging from 0.5 to 2.1 nM. B) Clone D2 and affinity matured and germline altered variants show IC$_{50}$ for this effect ranging from 0.15 to 1.5 nM (FIGS. 15-17). Data shown is representative of multiple experiments. IC$_{50}$ values were calculated using non-linear regression (GraphPad Prism).

In FIG. 15, the IC$_{50}$ data are provided in Table 1 below:

TABLE 1

| | Antibody | | | | | | |
|---|---|---|---|---|---|---|---|
| | A6 | A6-A1 | A6-A3 | A6-A4 | A6-A5 | A6-A7 | A6-A8 |
| IC$_{50}$ (M) | 1.1e$^{-9}$ | 5.1e$^{-10}$ | 1.1e$^{-9}$ | 1.05e$^{-9}$ | 1.1e$^{-9}$ | 5.6e$^{-10}$ | 6.0e$^{-10}$ |

In FIG. 17, the $IC_{50}$ data are provided in Table 2 below:

TABLE 2

| | Antibody | | | | | | | | | |
|---|---|---|---|---|---|---|---|---|---|---|
| | D2 | D2G-A1 | D2G-A2 | D2G-A4 | D2G-A5 | D2G-A6 | D2G-B8 | D2G-C1 | D2G-C4 | D2G-G1 |
| $IC_{50}$ (M) | $1.3e^{-9}$ | $1.6e^{-10}$ | $1.8e^{-10}$ | $1.7e^{-10}$ | $2.3e^{-10}$ | $2.2e^{-10}$ | $8.6e^{-10}$ | $2.0e^{-10}$ | $2.8e^{-10}$ | $8.9e^{-10}$ |

Example 12

This example is an analysis of ADCC using a cell based reporter assay. Antibody-dependent cell-mediated cytotoxicity (ADCC) is a mechanism of action of antibodies through which virus-infected or other diseased cells are targeted for destruction by components of the cell mediated immune system, such as natural killer cells. ADCC is a desirable mechanism for killing target cancer cells using antibody-based drugs. The antibody binds to target antigens on the cell surface. When the Fc effector portion of target-bound antibodies also binds to FcγRIIIa receptors on the cell surface of effector cells (natural killer cells predominantly), multiple cross-linking of the two cell types occurs, leading to pathway activation and ultimately cell killing. To assess the potential induction of ADCC by anti-EGFR mABs, a cell based reporter assay (ADCC Reporter Bioassay, Catalog #G7010, Promega) was used. In brief, 1250 A431 cells were seeded into the inner 320 wells of a white 384-well cell culture plate in 100 ul DMEM plus 10% FBS. Cells were allowed to attach overnight and in the morning, media was removed and replaced with 7 ul ADCC Assay Buffer (RPMI+4% Low IgG Fetal Bovine Serum) per well. A 9-point dilution curve of mAB was made at 3× final concentration in ADCC Assay Buffer. 7 ul of the antibody dilution was added to wells in triplicate distributed across the rows to avoid spatial effects. ADCC Effector cells were thawed according to manufacturer's protocol and 7 ul added to each well. The plate was incubated for 6 hr in the incubator (37° C., 5% $CO_2$) and then removed to the lab bench to reach room temperature. 21 ul of Bio-Glo Luciferase Assay Reagent was added to each well and allowed to incubate for 30 min. The plate was then read using a plate reader capable of luminescence detection. The RLU was plotted versus antibody concentration to determine the $EC_{50}$ for the effect. The anti-EGFR mAb A6 activated ADCC with an $EC_{50}$ of 60 pM. (FIG. 16A). The anti-EGFR mAb D2 activates ADCC with an $EC_{50}$ of 200 pM. (FIG. 16B).

```
                        Sequence Listing:

Binder  VH                                              VL

A3      QVTLRESGPTLVKPTQTLTLTCTFSGFSLTSLSESVA          SYELMQPPSVSVAPGMTARISCGANNIGSE
        WIRQSPGKALEWLALIYWDDDKLYSPSLKSRLTITKD           TVHWYQQKPGQAPVLVIYYDSDRPSGIPER
        TSKNEVVLTMTNVDSADTATYFCAHKKIRDTGFDF             FSGSKSGNTATLTITRVEAGDEADYYCQVW
        WGQGTLVTVSS SEQ ID NO. 1                         DSSTDHPVFGGGTKLTVL SEQ ID NO. 2

A5      EVQLVQSGAEVKKPGASVKVSCKASGGTFSSYAISW           DIQLTQSPSSLSASVGDRVTITCQASQDISNY
        VRQAPGQGLEWMGGIIPILGTADYAQKFQGRVTIT             LNWYQQKPGKAPKLLIYDASNTETGVPSRF
        ADESTSTAYMELSSLRSEDTAVYYCARDEIPLEYCTST          SGSGSGTDFTFTISSLQPEDIATYFCQHYANL
        SCYHAFDIWGQGTMVTVSS SEQ ID NO. 3                PLTFGPGTKVDIK SEQ ID NO. 4

A6      QVQLVQSGAEVKKPGSSVKVSCKASGGTFRNHAFS             QSVLTQPPSVSAAPGQEVTISCSGSNSNIGN
        WVRQAPGQGLEWMGWISAYNGYTHYAEKLQGRV               NYVSWYQQLPGTAPKLLIYDNNERPSGIPD
        TMTTDTSTSTAYMELRSLRSDDTAVYYCARVSASYN            RFSGSKSGTSATLGITGLQTGDEADYYCGT
        SDWSLHYYYGMDVWGQGTTVTVSS SEQ ID NO. 5           WDSSLSAGVFGGGTKLTVL SEQ ID NO. 6

A10     EVQLVESGGGLVKPGGSLRLSCVGSGVDTNSRAISW           SYELMQPPSVSVAPGQTAGITCGGRNIGSK
        VRQAPGKGLEWVSVIYSGGGGTNYADSVKGRFTIS            SVHWYQQKPGQAPLLVIYYDDDRPSGIPER
        RDKSRNTVFLQMNSLRVEDTALYYCAKDPGWPIAG             FSGSNSENTATLTISRVEAGDEADYFCQVW
        WYFDLWGRGTLVTVSS SEQ ID NO. 7                   DSSSDHYVFGAGTKLTVL SEQ ID NO. 8

A11     QVQLVQSGAEVKKPGASVKVSCKASGYTFIRNDIN             QPVLTQPASVSGSPGQSITISCTGTSSDIGAY
        WVRQASGQGLEWIGWMNPNTGATASAQNFQGR                HYISWYQQHPGKPPKLMIFDVAKRPSGVSD
        VAMTRNASMNTAYLELSGLRSDDTAIYYCARAFEDY            RFSGSKSGNTASLTISGLQADDEADYYCSSFS
        IWESSEFHFGLDVWGQGTTVTVSS SEQ ID NO. 9           RDTDVIFGGGTKLTVL SEQ ID NO. 10

B1      QVQLVQSGGGVVQPGRSLRLSCAASGFIFNHYAM              QSVLTQPPSASGTPGQRVTISCSGSSSNIGS
        HWVRQAPGKGLEWVAHISSDGSYKFYADSVKGRFT             NAVNWYQQLPGKAPKLLIYFDDLLPSGVSD
        VSRDNSDNTVYLQMNSLGPEDTAVYHCARFTEVLY             RFSGSKSGTSASLAISGLQSEDEADYYCAAW
        YGADYWGQGTLVTVSS SEQ ID NO. 11                  DDSLNGWVFGGGTKLTVL SEQ ID NO. 12

B4      QVQLVQSGAEVKKPGSAVKVSCKASGGTFSSYAIS            NIQMTQSPPSLSAFVGDRVTITCQASQAIN
        WVRQAPGQGLEWMGGIIPILGTADYAQKFQGRVT              NYLNWYQQKPGKAPKLLIYDASNLETGVPS
        ITADESTSTAYMELSSLRSEDTAVYYCARDEIPLEYCT          RFSGSGSGTDFTFTISSLQPEDNATYYCQQY
        STSCYHAFDIWGQGTMVTVSS SEQ ID NO. 13             DKLPLTFGGGTKVEIK SEQ ID NO. 14

B5      QMQLVQSWAEVKKPGASVKVSCKASAYTFTNYYIH             QSVLTQPASVSGSPGQSITISCTGTTSDVGG
        WVRQAPGQGLEWMGIINPSSGATTYAQRLQGRVI              FNYVSWYQQHPGKVPKLIIFDVSNRPSVS
```

Sequence Listing:

| Binder | VH | VL |
|---|---|---|
| | MTRDTSTSTVNMELSSLRSEDTAVYYCARSTLWFSE FDYWGQGTLVTVSS SEQ ID NO. 15 | DRFSGSKSVNTASLTISGLQAEDEADYYCSSY TDSGSYIFGTGTKVTVL SEQ ID NO. 16 |
| B6 | QVQLVQSGAEVKKPGASVKVSCKASGYTFTGYYMH WVRQAPGQGLEWMGWINPNSGGTNYAQKFQGR VTMTRDTSISTAYMELSRLRSDDTAVYYCARRYYDS SLSFDYWGQGTLVTVSS SEQ ID NO. 17 | QAVLTQPASVSGSPGQSITISCTGTSSDVGG YNYVSWYQQHPGKAPKLIIYDVTKRPSGFS NRFSGSKSGNTASLTISGLQAEDEADYYCSS YTTSSTRVFGTGTKVTVL SEQ ID NO. 18 |
| B7 | QVQLVQSGAEVKKPGASVKVSCKASGYTFTGYYMH WVRQAPGQGLEWMGWINPNSGGTNYAQKFQGR VTMTRDTSISTAYMELSRLRSDDTAVYYCARDGGN WNYGGGDYWGQGTLVTVSS SEQ ID NO. 19 | SYELMQPASVSGSPGQSITISCTGTSSDIGDY NYVSWYQQHPGKAPKLIIYDVSIRPSGVSLR FSGSKSGNTASLTISGLQAEDEADYYCSSYR NTDTLEFGGGTKVTVL SEQ ID NO. 20 |
| D2 | EVQLVESGGGVVQPGRSLRLSCAASGFIFNHYAMH WVRQAPGKGLEWVAHISSDGSYKFYADSVKGRFTV SRDNSDNTVYLQMNSLGPEDTAVYHCARFTEVLYY GADYWGQGTLVTVSS SEQ ID NO. 21 | QSVLTQPPSVSEAPRQRVSISCSGSSSNIGN NAVNWYQQLPGKAPKLLIYFDDLLPSGVSD RFSGSKSGTSASLAISGLQSEDEADYYCAAW DDSLKGYVFGTGTKVTVL SEQ ID NO. 22 |
| D4 | QVQLQQSGAEVKKPGASVKVSCKASGYTFTDHGII WVRQAPGQGLEWMGWINTDNGNTIYAPKFQGR VTMTTDTSTSIVYMELQSLRSDDTAVYFCSREDWN YDGGLREVFDYWGQGTLVTVSS SEQ ID NO. 23 | QSVLTQPPSASGTPGQRVTISCSGSTANIGR NYVNWYQQFPGTAPKLLMYSNDQSPSGV RGRFSGSKSGTSASLAINGLQSEDEADYYCA AWDDDRLNAYVFGTGTKLTVL SEQ ID NO. 24 |
| D6 | EVQLVQSGAEVKKPGSAVKVSCKASGGTFSSYAISW VRQAPGQGLEWMGGIIPILGTADYAQKFQGRVTIT ADESTSTAYMELSSLRSEDTAVYYCARDEIPLEYCTST SCYHAFDIWGRGTMVTVSS SEQ ID NO. 25 | AIQLTQSPSTLSASVGDRVTITCRASQSISSW LAWYQQKPGKAPKLLIYAASSLQSGVPSRFS GSGSGTDFTLTISSLQPEDFATYYCQQSYSTP LTFGGGTKVEIK SEQ ID NO. 26 |
| D10 | QVQLVESGGGLVQPGGSLRLFCAASGFGVSTNYMS WVRQAPGKGLEWVSVIYSGGATYYADSVKGRFTIS RDNSKNTLYLQMNSLRPEDTAVYYCAKESPNDDYF DYWGQGTLVTVSS SEQ ID NO. 27 | AIRMTQSPSSVSASVGDRVTITCRASQGIDS WLAWYQQKPGEAPKLLIYGASNLQSGVPIR FSGSGSGTDFTLTIRSLQPEDFATYFCQQSH GAPYTFGQGTKVEIK SEQ ID NO. 28 |
| E1 | QVQLVQSGAEVKKPGSSVKVSCKASGGTFSSYAISW VRQAPGQGLEWMGGIIPIFGTASYAQKFQGRVTIT ADESTTTAYMELSSLRSEDTAVYYCAREGPEYCSGG TCYSADAFDIWGQGTMVTVSS SEQ ID NO. 29 | QSVVTQPPSVSAAPGQKVTISCSGSTSNIEN YSVSWYQQLPGTAPKLLIYDNNKRPSGIPDR FSGSKSGTSATLGITGLQTGDEADYYCGTW DNRLSSVVFGGGTKVTVL SEQ ID NO. 30 |
| EG-A4 | QVQLVESGGGLVQPGGSLRLSCAASGFTFSSYWMS WVRQAPGKGLEWVANIKQDGSEKYYVDSVKGRFTI SRDNAKNSLYLQMNSLRAEDTAVYYCAREAPIAAD AFDIWGQGTMVTVSS SEQ ID NO. 31 | DIVMTQSPVSLSASVGDSVTITCRASQSISSY LNWYQQKPGKAPKLLIYAASSLQSGVPSRFS GSGSGTDFTLTISSLQPEDFATYYCQQSYSLY TFGQGTKLEIK SEQ ID NO. 32 |
| EG-B7 | EVQLVQSGAEVKKPGSSVKVSCKASGGTFSSYPISW VRQAPGQGLEWMGGIIPIFGIANYAQKFQGRVTIT ADESTSTAYMELSSLRSEDTAVYYCARDSSGYSLYW GQGTLVTVSS SEQ ID NO. 33 | QSVLTQPPSASGSPGQSVTISCTGARSDVG GYNYVSWYQQHPGKAPKLMIYDVSNRPSG VSNRFSGSKSGNTASLTISGLQAEDEADYYC SSYTSSSTYVFGTGTKLTVL SEQ ID NO. 34 |
| EG-C9 | QVQLVQSGAEVKKPGESLRISCKGSGYSFTSYWISW VRQMPGKGLEWMGWIDPSDSYTNYSPSFQGHVTI SADKSISTAYLQWSSLKASDTAVYYCAIQTSSSDAFDI WGQGTMVTVSS SEQ ID NO. 35 | DVVMTQSPATLSLSPGERATLSCRASQSVN TYLAWYQQKPGQAPRLLIYDASSRATGIPAR FSGSGSGTDFTLTISSLEPEDFATYYCQQTYS TPFTFGPGTKVDIK SEQ ID NO. 36 |
| EG-D5 | QVQLQQSGPGLVKPSQTLSLTCAISGDSVASNGAS WNWIRQSPSRGLEWLSKTYYRSKWYYEYAPSVTSR MTISPDTSKNQFSLQVTSVTPEDTAVYYCARLIGDGL IDYWGQGTLVTVSS SEQ ID NO. 37 | EIVMTQSPDSLAVSLGERATINCKSSQSVLYS SNNKNYLAWYQQKPGQPPKLLIYWASTRES GVPDRFSGSGSGTDFTLTISSLQAEDVAVYY CQQYYTTPLTFGGGTKVEIK SEQ ID NO. 38 |
| EG-E9 | QVTLRESGPTLVKPTQTLTLTCTFSGFSLTSLSESVA WIRQSPGKALEWLALIYWDDDKLYSPSLKSRLTITKD TSKNEVVLTMTNVDSADTATYFCAHKKIRDTGFDF WGQGTLVTVSS SEQ ID NO. 39 | QAVVTQPPSASVAPGQTARITCEGNNIESKS VHWYQQKPGQAPVLVIYYDRDRPSGIPERF SGSNSGNTATLTISRVEAGDEADYYCQVWD SSSDHPVFGGGTKLTVL SEQ ID NO. 40 |
| EG-E11 | EVQLVESGGGLVKPGGSLRLSCVGSGVDTNSRAISW VRQAPGKGLEWVSVIYSGGGGTNYADSVKGRFTIS RDKSRNTVFLQMNSLRVEDTALYYCAKDPGWPIAG WYFDLWGRGTLVTVSS SEQ ID NO. 41 | QPVLTQPPSVSVAPGKTARITCGGNNIGSKS VHWYQQKPGQAPVLVIYYDSDRPSGIPERF SGSNSGNTATLTISRVEAGDEADYYCQVWD SSSDHYVFGTGTKLTVR SEQ ID NO. 42 |
| EB8 | QVQLQQSGPGLVQPSQTLSLTCAISGDTVSTNYHA WNWIRQSPSRGLEWLGRTYYRSKWYNDYAVSVKS RVTISPDTSKNHFSLQLKSVTPEDTAVYYCARDGGTT NYYNVFDVWGQGTTVTVSS SEQ ID NO. 43 | SSELTQDPAVSVALGQTVRITCQGDSLRSYY ASWYQQKPGQAPVLVIYGKNNRPSGIPDRF SGSSSGNTASLTITGAQAEDEADYYCNSRDS SGNHHVVFGGGTKLTVL SEQ ID NO. 44 |

| Binder | VH | VL |
|---|---|---|
| EC6 | EVQLVQSGAEVKKPGASVKVSCKASGYTFTGYYMH WVRQAPGQGLEWLGWINPSSGFTDYAHKFQGRV TMTRDTSTSTVYMELSSLRSEDTAVYYCARSTLWFS EFDYWGQGTLVTVSS SEQ ID NO. 45 | QPVLTQPPSASGTPGQRVTISCSGSSSNIGS YTVNWYQQLPGTAPKLLIYNNNERPSGVPD RFSGSKSGTSASLAISGLQSEDEADYYCASW DDRLSGDVIFGGGTKLTVL SEQ ID NO. 46 |
| EC10 | QVQLVESGAEVKKPGASVKVSCKASGYTFTDYHIH WVRQAPGQGLEWMGWINTYNGNTQYAQHVQD RVTMTRDSATSSVYLELRSLRSDDTALYFCALPNDYY SYAMDVWGQGTTVTVSS SEQ ID NO. 47 | DVVMTQSPATLSLSPGERATLSCRASQSVSS YLAWYQQKPGQAPRLLIYDASNRATGIPAR FSGSGSGTDFTLTISSLEPEDFATYYCQQYQV YPTTFGQGTRLEIK SEQ ID NO. 48 |
| ED10 | EVQLVESGAEVKKPGASVKVSCKASGYTFTSYYMH WVRQAPGQGLEWMGIINPNDGSTTYAQNFQGRIT MTRDTSTRTAYMELSSLRSEDTAVYYCARVDSSLGG YYYGMDVWGQGTTVTVSS SEQ ID NO. 49 | LPVLTQPPSVSVAPGETAKITCGGTYIVRKIV HWYQQKPGQAPRLVIYYDAARPSGIPERFS GSNSGNTATLTISGVEAGDEADYYCQVWD NDSDHYVFGPGTKVTVL SEQ ID NO. 50 |
| EE12 | QVQLQQWAEVKKPGASVKVSCKASGYTFTDHYID WVRQAPGQGLEWMGRINPNSGYTNYAQTFQGRV TMTRDTSINTAYMDLSSLRSEDTAVYYCARSTLWFS EFDYWGQGTLVTVSS SEQ ID NO. 51 | QAVLTQPASVSGSPGQSITISCTGTSSDVGD YNYVSWYQQHPGKAPKLMIYDVSNRPSGV SYRFSGSKSGNTASLTISGLQAEDEADYYCSS YTSSSSYVFGTGTKVTVL SEQ ID NO. 52 |
| RE-A1 | EVQLLESGGGVVQPGRSLRLSCAASGFTFSSYAIHW VRQAPGKGLEWVAVISFDGNNKYYADSMKGRFTIS RDNAKNSLYLQMNSLRAEDTAVYYCARDQYYDILT GYYYGMDVWGQGTTVTVSS SEQ ID NO. 53 | QSALTQPASVSVAPGTTARITCGGSNIARKN VHWYQQKPGQAPLVVVSDESDRPSGIPERF SGSNSGNTATLTISRVEAGDEADYYCQVWD SSSDHPVFGGGTKLTVL SEQ ID NO. 54 |
| RE-F3 | EVQLVESGGGLVKPGGSLRLSCAASGFTFSSYSMN WVRQAPGKGLEWVSSISSSSSYIYYADSVKGRFTISR DNAKNSLYLQMNSLRAEDTAVYYCARHGSYYDPYY GMDVWGQGTTVTVSS SEQ ID NO. 55 | QPVLTQPPSASGTPGQRVTISCSGSSSNIGR NYVFWYQQLPGTAPKLLIYSNNQRPSGVPD RFSGSKSGTSASLAISGLQSEDEADYYCAAW DDSLNVVFGGGTKLTVL SEQ ID NO. 56 |
| RE-F4 | EVQLVQSGAEVKNPGASVKVSCKASGFTFTSYDLN WVRQAPGQGLEWMGWMNPINGNTGYAQKFQG RVSMTRDTSTSTVYMELSSLRSEDTAVYYCARADL WFGELDYWGQGTLVTVSS SEQ ID NO. 57 | DIQLTQSPSSLSASVGDRVTIAC RASQSISSYL NWYQKKVGKAPKLLIYAASSLQSGVPSRFS GSGSGSGTDFTLTISSLQPEDFATYYCQQSYSIP VTFGQGTKVEIK SEQ ID NO. 58 |
| G3 | EVQLVQSGAEVKKPGASVKVSCKASGGTFSSYAISW VRQAPGQGLEWMGGIIPILGTADYAQKFQGRVTIT ADESTSTAYMELSSLRSEDTAVYYCARDEIPLEYCTST SCYHAFDIWGQGTMVTVSS SEQ ID NO. 59 | DIQLTQSPSSLSASVGDRVTITCQASQDISNY LNWYQQKPGKAPKLLIYDASNTETGVPSRF SGSGSGTDFTFTISSLQPEDIATYFCQHYANL PLTFGPGTKVDIK SEQ ID NO. 60 |
| A6-A1 | QVQLVQSGAEVKKPGSSVKVSCKASGGTFRNHAW SWVRQAPGQGLEWMGWISAYNGYTHYASKLQGR VTMTTDTSTSTAYMELRSLRSDDTAVYYCARVSAEY AEDWSLHYYYMDVWGQGTLVTVSS SEQ ID NO. 61 | QSVLTQPPSVSAAPGQEVTISCSGSNSNIGN NYVSWYQQLPGTAPKLLIYDNNERPSGIPD RFSGSKSGTSATLGITGLQTGDEADYYCSTW DSSLSAVVFGGGTKLTVL SEQ ID NO. 62 |
| A6-A3 | QVQLVQSGAEVKKPGSSVKVSCKASGGTFRNHAW SWVRQAPGQGLEWMGWISAYNGYTTYASKLQGR VTMTTDTSTSTAYMELRSLRSDDTAVYYCARVSASY NEDWSLHYYYGMDVWGQGTLVTVSS SEQ ID NO. 63 | QSVLTQPPSVSAAPGQEVTISCSGSNSNIEP NYVSWYQQLPGTAPKLLIYSTAERPSGIPDR FSGSKSGTSATLGITGLQTGDEADYYCSTWD SSLSAVVFGGGTKLTVL SEQ ID NO. 64 |
| A6-A4 | QVQLVQSGAEVKKPGSSVKVSCKASGGTFRNHAYS WVRQAPGQGLEWMGWISAYNGYTTYASKLQGRV TMTTDTSTSTAYMELRSLRSDDTAVYYCARVSASYN SDWSLHYYYGMDVWGQGTLVTVSS SEQ ID NO. 65 | QSVLTQPPSVSAAPGQEVTISCSGSNSNIEN NYVSWYQQLPGTAPKLLIYSNNERPSGIPDR FSGSKSGTSATLGITGLQTGDEADYYCGTFD SSLSAVVFGGGTKLTVL SEQ ID NO. 66 |
| A6-A5 | QVQLVQSGAEVKKPGSSVKVSCKASGGTFRNHAYS WVRQAPGQGLEWMGWISAYNGYTHYASKLQGRV TMTTDTSTSTAYMELRSLRSDDTAVYYCARVSASYA SDWSLHYYYGMDVWGQGTLVTVSS SEQ ID NO. 67 | QSVLTQPPSVSAAPGQEVTISCSGSNSNIGN NYVSWYQQLPGTAPKLLIYDTAERPSGIPDR FSGSKSGTSATLGITGLQTGDEADYYCSTWD SSLSAVLFGGGTKLTVL SEQ ID NO. 68 |
| A6-A6 | QVQLVQSGAEVKKPGSSVKVSCKASGGTFRNHAYS WVRQAPGQGLEWMGWISAYNGYTTYASKLQGRV TMTTDTSTSTAYMELRSLRSDDTAVYYCARVSAEYN SDWSLHYYYGMDVWGQGTLVTVSS SEQ ID NO. 69 | QSVLTQPPSVSAAPGQEVTISCSGSNSNIPN NYVSWYQQLPGTAPKLLIYSNYERPSGIPDR FSGSKSGTSATLGITGLQTGDEADYYCSTWD SSLSAVVFGGGTKLTVL SEQ ID NO. 70 |
| A6-A7 | QVQLVQSGAEVKKPGSSVKVSCKASGGTFRNHAYS WVRQAPGQGLEWMGWISAYNGYTHYAEKLQGRV TMTTDTSTSTAYMELRSLRSDDTAVYYCARVSAEYN SDWSVHYYYGMDVWGQGTLVTVSS SEQ ID NO. 71 | QSVLTQPPSVSAAPGQEVTISCSGSNSNIGP NYVSWYQQLPGTAPKLLIYDNNERPSGIPD RFSGSKSGTSATLGITGLQTGDEADYYCSTF DSSLSAAVFGGGTKLTVL SEQ ID NO. 72 |

-continued

Sequence Listing:

| Binder | VH | VL |
|---|---|---|
| A6-A8 | QVQLVQSGAEVKKPGSSVKVSCKASGGTFRNHAYS WVRQAPGQGLEWMGWISAYNGYTTYAEKLQGRV TMTTDTSTSTAYMELRSLRSDDTAVYYCARVSAEYA EDWSLHYYYGMDVWGQGTLVTVSS SEQ ID NO. 73 | QSVLTQPPSVSAAPGQEVTISCSGSNSNIPN NYVSWYQQLPGTAPKLLIYSNSERPSGIPDR FSGSKSGTSATLGITGLQTGDEADYYCSTWD SSLSAALFGGGTKLTVL SEQ ID NO. 74 |
| D2GA1 | EVQLVESGGGVVQPGRSLRLSCAASGFIFHHYAMH WVRQAPGKGLEWVAHISSDGSSKFYADSVKGRFTV SRDNSKNTLYLQMNSLRAEDTAVYYCARFTEVLYYG ADLWGQGTLVTVSS SEQ ID NO. 75 | QSVLTQPPSVSEAPRQRVSISCSGSSSNIGN NAVNWYQQLPGKAPKLLIYFDDLLPLGVSD RFSGSKSGTSASLAISGLQSEDEADYYCAAW DDSLKGYVFGTGTKVTVL SEQ ID NO. 76 |
| D2GA2 | EVQLVESGGGVVQPGRSLRLSCAASGFIFHHYAMH WVRQAPGKGLEWVAHISPDGSSKFYADSVKGRFTV SRDNSKNTLYLQMNSLRAEDTAVYYCARFTEVLYYG ADIWGQGTLVTVSS SEQ ID NO. 77 | QSVLTQPPSVSEAPRQRVSISCSGSSSNIGN NAVNWYQQLPGKAPKLLIYFDDLLPSGVSD RFSGSKSGTSASLAISGLQSEDEADYYCAAW DDSLKGYVFGTGTKVTVL SEQ ID NO. 78 |
| D2GA4 | EVQLVESGGGVVQPGRSLRLSCAASGFIFHHYAMH WVRQAPGKGLEWVAHISSDGSSKFYADSVKGRFTV SRDNSKNTLYLQMNSLRAEDTAVYYCARFTEVLYYG ADLWGQGTLVTVSS SEQ ID NO. 79 | QSVLTQPPSVSEAPRQRVSISCSGSSSNIGD NAVNWYQQLPGKAPKLLIYYDDLHPSGVSD RFSGSKSGTSASLAISGLQSEDEADYYCAAW DDSLKGYVFGTGTKVTVL SEQ ID NO. 80 |
| D2GA5 | EVQLVESGGGVVQPGRSLRLSCAASGFIFHHYAMH WVRQAPGKGLEWVAHISIDGSSKFYADSVKGRFTV SRDNSKNTLYLQMNSLRAEDTAVYYCARFTEVLYYG ADLWGQGTLVTVSS SEQ ID NO. 81 | QSVLTQPPSVSEAPRQRVSISCSGSSSNIGN NAVNWYQQLPGKAPKLLIYYDDLLPSGVSD RFSGSKSGTSASLAISGLQSEDEADYYCAAW DDSLKGYVFGTGTKVTVL SEQ ID NO. 82 |
| A6-A11 | QVQLVQSGAEVKKPGSSVKVSCKASGGTFRNHAYS WVRQAPGQGLEWMGWISAYNGYTTYAEKLQGRV TMTTDTSTSTAYMELRSLRSDDTAVYYCARVSAEYN SDWSVHYYYGMDVWGQGTLVTVSS SEQ ID NO. 83 | QSVLTQPPSVSAAPGQEVTISCSGSNSNIGN NYVSWYQQLPGTAPKLLIYSTNERPSGIPDR FSGSKSGTSATLGITGLQTGDEADYYCGTW DSSLSAGVFGGGTKLTVL SEQ ID NO. 84 |
| A6-A12 | QVQLVQSGAEVKKPGSSVKVSCKASGGTFRNHAW SWVRQAPGQGLEWMGWISAYNGYTTYASKLQGR VTMTTDTSTSTAYMELRSLRSDDTAVYYCARVSAEY ASDWSLHYYYGMDVWGQGTLVTVSS SEQ ID NO. 85 | QSVLTQPPSVSAAPGQEVTISCSGSNSNIEN NYVSWYQQLPGTAPKLLIYDNRERPSGIPDR FSGSKSGTSATLGITGLQTGDEADYYCGTW DSSLSAGVFGGGTKLTVL SEQ ID NO. 86 |
| A6-A13 | QVQLVQSGAEVKKPGSSVKVSCKASGGTFRNHAYS WVRQAPGQGLEWMGWISAYNGYTTYAEKLQGRV TMTTDTSTSTAYMELRSLRSDDTAVYYCARVSAEYN SDWSVHYYYGMDVWGQGTLVTVSS SEQ ID NO. 87 | QSVLTQPPSVSAAPGQEVTISCSGSNSNIEP NYVSWYQQLPGTAPKLLIYSTYERPSGIPDR FSGSKSGTSATLGITGLQTGDEADYYCGTFD SSLSAAVFGGGTKLTVL SEQ ID NO. 88 |
| A6-A14 | QVQLVQSGAEVKKPGSSVKVSCKASGGTFRNHAW SWVRQAPGQGLEWMGWISAYNGYTTYAEKLQGR VTMTTDTSTSTAYMELRSLRSDDTAVYYCARVSAEY AEDWSLHYYYGMDVWGQGTLVTVSS SEQ ID NO. 89 | QSVLTQPPSVSAAPGQEVTISCSGSNSNIGN NYVSWYQQLPGTAPKLLIYSTNERPSGIPDR FSGSKSGTSATLGITGLQTGDEADYYCGTW DSSLSAALFGGGTKLTVL SEQ ID NO. 90 |
| A6-A15 | QVQLVQSGAEVKKPGSSVKVSCKASGGTFRNHAW SWVRQAPGQGLEWMGWISAYNGYTTYASKLQGR VTMTTDTSTSTAYMELRSLRSDDTAVYYCARVSASY ASDWSVHYYYGMDVWGQGTLVTVSS SEQ ID NO. 91 | QSVLTQPPSVSAAPGQEVTISCSGSNSNIEN NYVSWYQQLPGTAPKLLIYDNAERPSGIPD RFSGSKSGTSATLGITGLQTGDEADYYCSTW DSSLSAVVFGGGTKLTVL SEQ ID NO. 92 |
| A6-A17 | QVQLVQSGAEVKKPGSSVKVSCKASGGTFRNHAW SWVRQAPGQGLEWMGWISAYNGYTTYASKLQGR VTMTTDTSTSTAYMELRSLRSDDTAVYYCARVSASY NSDWSVHYYYGMDVWGQGTLVTVSS SEQ ID NO. 93 | QSVLTQPPSVSAAPGQEVTISCSGSNSNIGN NYVSWYQQLPGTAPKLLIYDNAERPSGIPD RFSGSKSGTSATLGITGLQTGDEADYYCSTW DSSLSAVLFGGGTKLTVL SEQ ID NO. 94 |
| A6-A18 | QVQLVQSGAEVKKPGSSVKVSCKASGGTFRNHAW SWVRQAPGQGLEWMGWISAYNGYTTYAEKLQGR VTMTTDTSTSTAYMELRSLRSDDTAVYYCARVSASY ASDWSLHYYYGMDVWGQGTLVTVSS SEQ ID NO. 95 | QSVLTQPPSVSAAPGQEVTISCSGSNSNIGN NYVSWYQQLPGTAPKLLIYDNNERPSGIPD RFSGSKSGTSATLGITGLQTGDEADYYCGTF DSSLSAALFGGGTKLTVL SEQ ID NO. 96 |
| A6-A20 | QVQLVQSGAEVKKPGSSVKVSCKASGGTFRNHAW SWVRQAPGQGLEWMGWISAYNGYTTYAEKLQGR VTMTTDTSTSTAYMELRSLRSDDTAVYYCARVSAEY AEDWSLHYYYGMDVWGQGTLVTVSS SEQ ID NO. 97 | QSVLTQPPSVSAAPGQEVTISCSGSNSNIPN NYVSWYQQLPGTAPKLLIYSTSERPSGIPDR FSGSKSGTSATLGITGLQTGDEADYYCSTWD SSLSAVVFGGGTKLTVL SEQ ID NO. 98 |

-continued

Sequence Listing:

| Binder | VH | VL |
|---|---|---|
| A6-A21 | QVQLVQSGAEVKKPGSSVKVSCKASGGTFRNHAYS WVRQAPGQGLEWMGWISAYNGYTTYASKLQGRV TMTTDTSTSTAYMELRSLRSDDTAVYYCARVSASYN EDWSLHYYYGMDVWGQGTLVTVSS SEQ ID NO. 99 | QSVLTQPPSVSAAPGQEVTISCSGSNSNIEN NYVSWYQQLPGTAPKLLIYSNRERPSGIPDR FSGSKSGTSATLGITGLQTGDEADYYCSTFD SSLSAVVFGGGTKLTVL SEQ ID NO. 100 |
| A6-A22 | QVQLVQSGAEVKKPGSSVKVSCKASGGTFRNHAYS WVRQAPGQGLEWMGWISAYNGYTTYASKLQGRV TMTTDTSTSTAYMELRSLRSDDTAVYYCARVSASYN SDWSVHYYYGMDVWGQGTLVTVSS SEQ ID NO. 101 | QSVLTQPPSVSAAPGQEVTISCSGSNSNITN NYVSWYQQLPGTAPKLLIYDNNERPSGIPD RFSGSKSGTSATLGITGLQTGDEADYYCSTW DSSLSALLFGGGTKLTVL SEQ ID NO. 102 |
| A6-A23 | QVQLVQSGAEVKKPGSSVKVSCKASGGTFRNHAYS WVRQAPGQGLEWMGWISAYNGYTTYAEKLQGRV TMTTDTSTSTAYMELRSLRSDDTAVYYCARVSAEYA SDWSLHYYYGMDVWGQGTLVTVSS SEQ ID NO. 103 | QSVLTQPPSVSAAPGQEVTISCSGSNSNIPN NYVSWYQQLPGTAPKLLIYDNNERPSGIPD RFSGSKSGTSATLGITGLQTGDEADYYCSTW DSSLSAVLFGGGTKLTVL SEQ ID NO. 104 |
| A6-A24 | QVQLVQSGAEVKKPGSSVKVSCKASGGTFRNHAYS WVRQAPGQGLEWMGWISAYNGYTTYAEKLQGRV TMTTDTSTSTAYMELRSLRSDDTAVYYCARVSAEYA SDWSLHYYYGMDVWGQGTLVTVSS SEQ ID NO. 105 | QSVLTQPPSVSAAPGQEVTISCSGSNSNIGP NYVSWYQQLPGTAPKLLIYDNRERPSGIPDR FSGSKSGTSATLGITGLQTGDEADYYCSTWD SSLSAGVFGGGTKLTVL SEQ ID NO. 106 |
| D2GA6 | EVQLVESGGGVVQPGRSLRLSCAASGFIFHHYAMH WVRQAPGKGLEWVAHISPDGSSKFYADSVKGRFTV SRDNSKNTLYLQMNSLRAEDTAVYYCARFTEVLYYG ADIWGQGTLVTVSS SEQ ID NO. 107 | QSVLTQPPSVSEAPRQRVSISCSGSSSNIGN NAVNWYQQLPGKAPKLLIYFDDLLPQGVSD RFSGSKSGTSASLAISGLQSEDEADYYCAAW DDSLKGYVFGTGTKVTVL SEQ ID NO. 108 |
| D2GA9 | EVQLVESGGGVVQPGRSLRLSCAASGFIFHHYAMH WVRQAPGKGLEWVAHISLDGSYKFYADSVKGRFTV SRDNSKNTLYLQMNSLRAEDTAVYYCARFTEVLYYG ADIWGQGTLVTVSS SEQ ID NO. 109 | QSVLTQPPSVSEAPRQRVSISCSGSSSNIGN NAVNWYQQLPGKAPKLLIYFDDLHPSGVSD RFSGSKSGTSASLAISGLQSEDEADYYCAAW DDSLKGYVFGTGTKVTVL SEQ ID NO. 110 |
| D2GA10 | EVQLVESGGGVVQPGRSLRLSCAASGFIFHHYAMH WVRQAPGKGLEWVAHISPDGSSKFYADSVKGRFTV SRDNSKNTLYLQMNSLRAEDTAVYYCARFTEVLYYG ADIWGQGTLVTVSS SEQ ID NO. 111 | QSVLTQPPSVSEAPRQRVSISCSGSSSNIGN NAVNWYQQLPGKAPKLLIYFDDLHPSGVSD RFSGSKSGTSASLAISGLQSEDEADYYCAAW DDSLKGYVFGTGTKVTVL SEQ ID NO. 112 |
| D2GA11 | EVQLVESGGGVVQPGRSLRLSCAASGFIFHHYAMH WVRQAPGKGLEWVAHISPDGSSKFYADSVKGRFTV SRDNSKNTLYLQMNSLRAEDTAVYYCARFTEVLYYG ADYWGQGTLVTVSS SEQ ID NO. 113 | QSVLTQPPSVSEAPRQRVSISCSGSSSNIGN NAVNWYQQLPGKAPKLLIYFDDLLPSGVSD RFSGSKSGTSASLAISGLQSEDEADYYCAAW DDSLKGYVFGTGTKVTVL SEQ ID NO. 114 |
| D2GB2 | EVQLVESGGGVVQPGRSLRLSCAASGFIFHHYAMH WVRQAPGKGLEWVAHISPDGSYKFYADSVKGRFTV SRDNSKNTLYLQMNSLRAEDTAVYYCARFTEVLYYG ADLWGQGTLVTVSS SEQ ID NO. 115 | QSVLTQPPSVSEAPRQRVSISCSGSSSNIGN NAVNWYQQLPGKAPKLLIYYDDLLPSGVSD RFSGSKSGTSASLAISGLQSEDEADYYCAAW DDSLKGYVFGTGTKVTVL SEQ ID NO. 116 |
| D2GB6 | EVQLVESGGGVVQPGRSLRLSCAASGFIFHHYAMH WVRQAPGKGLEWVAHISSDGSSKFYADSVKGRFTV SRDNSKNTLYLQMNSLRAEDTAVYYCARFTEVLYYG ADLWGQGTLVTVSS SEQ ID NO. 117 | QSVLTQPPSVSEAPRQRVSISCSGSSSNVGN NAVNWYQQLPGKAPKLLIYFDDLLPSGVSD RFSGSKSGTSASLAISGLQSEDEADYYCAAW DDSLKGYVFGTGTKVTVL SEQ ID NO. 118 |
| D2GB7 | EVQLVESGGGVVQPGRSLRLSCAASGFIFHHYAMH WVRQAPGKGLEWVAHISSDGSYKFYADSVKGRFTV SRDNSKNTLYLQMNSLRAEDTAVYYCARFTEVLYYG ADLWGQGTLVTVSS SEQ ID NO. 119 | QSVLTQPPSVSEAPRQRVSISCSGSSSNIGN NAVNWYQQLPGKAPKLLIYFDDLHPSGVSD RFSGSKSGTSASLAISGLQSEDEADYYCAAW DDSLKGYVFGTGTKVTVL SEQ ID NO. 120 |
| D3GB8 | EVQLVESGGGVVQPGRSLRLSCAASGFIFHHYAMH WVRQAPGKGLEWVAHISPDGSYKFYADSVKGRFTV SRDNSKNTLYLQMNSLRAEDTAVYYCARFTEVLYYG ADIWGQGTLVTVSS SEQ ID NO. 121 | QSVLTQPPSVSEAPRQRVSISCSGSSSNIGN NAVNWYQQLPGKAPKLLIYYDDLLPSGVSN RFSGSKSGTSASLAISGLQSEDEADYYCAAW DDSLKGYVFGTGTKVTVL SEQ ID NO. 122 |
| D2GC1 | EVQLVESGGGVVQPGRSLRLSCAASGFIFHHYAMH WVRQAPGKGLEWVAHISPDGSSKFYADSVKGRFTV SRDNSKNTLYLQMNSLRAEDTAVYYCARFTEVLYYG ADLWGQGTLVTVSS SEQ ID NO. 123 | QSVLTQPPSVSEAPRQRVSISCSGSSSNIGN NAVNWYQQLPGKAPKLLIYYDDLLPSGVSD RFSGSKSGTSASLAISGLQSEDEADYYCAAW DDSLKGYVFGTGTKVTVL SEQ ID NO. 124 |
| D2GC4 | EVQLVESGGGVVQPGRSLRLSCAASGFIFHHYSMH WVRQAPGKGLEWVAHISSDGSSKFYADSVKGRFTV SRDNSKNTLYLQMNSLRAEDTAVYYCARFTEVLYYG ADLWGQGTLVTVSS SEQ ID NO. 125 | QSVLTQPPSVSEAPRQRVSISCSGSSSNIGN NAVNWYQQLPGKAPKLLIYYDDLLPSGVSD RFSGSKSGTSASLAISGLQSEDEADYYCAAW DDSLKGYVFGTGTKVTVL SEQ ID NO. 126 |

| Sequence Listing: | |
|---|---|
| Binder VH | VL |
| D2GG1 EVQLVESGGGVVQPGRSLRLSCAASGFTFSHYAMH WVRQAPGKGLEWVAHISLDGSSKFYADSVKGRFTV SRDNSKNTLYLQMNSLRAEDTAVYYCARFTEVLYYG ADLWGQGTLVTVSS SEQ ID NO. 127 | QSVLTQPPSVSEAPRQRVSISCSGSSSNIGN NAVNWYQQLPGKAPKLLIYYDDLLPSGVSD RFSGSKSGTSASLAISGLQSEDEADYYCAAW DDSLKGYVFGTGTKVTVL SEQ ID NO. 128 |

We claim:

1. An antibody that binds to Epidermal Growth Factor Receptor (EGFR), the antibody comprising:
   (a) a heavy chain variable domain comprising CDR1, CDR2 and CDR3 region amino acid sequences set forth in SEQ ID NO. 5 21, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, or 127; and
   (b) a light chain variable domain comprising CDR1, CDR2 and CDR3 region amino acid sequences set forth in SEQ ID NO. 6, 22, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, or 128.

2. The antibody of claim 1, wherein the antibody comprises; a heavy chain variable domain sequence that is at least 95% identical to an amino acid sequence selected from the group consisting of SEQ ID NO. 5, SEQ ID NO. 21, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, and SEQ ID NO. 127, and a light chain variable domain sequence that is at least 95% identical to an amino acid sequence selected from the group consisting of SEQ ID NO. 6, SEQ ID NO. 22, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128.

3. The antibody of claim 2, wherein the antibody comprises a heavy chain/light chain variable domain sequence selected from the group consisting of SEQ ID NO. 5/SEQ ID NO. 6, SEQ ID NO. 21/SEQ ID NO. 22, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, and SEQ ID NO. 127/SEQ ID NO. 128.

4. The antibody of claim 1, wherein the antibody is a Fab fragment comprising: a heavy chain variable domain sequence that is at least 95% identical to an amino acid sequence selected from the group consisting of SEQ ID NO. 5, SEQ ID NO. 21, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, and SEQ ID NO. 127, and a light chain variable domain sequence that is at least 95% identical to an amino acid sequence selected from the group consisting SEQ ID NO. 6, SEQ ID NO. 22, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128.

5. The Fab fragment of claim 4, wherein the Fab Fragment comprises a heavy chain/light chain variable domain sequence selected from the group consisting of SEQ ID NO. 5/SEQ ID NO. 6, SEQ ID NO. 21/SEQ ID NO. 22, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, and SEQ ID NO. 127/SEQ ID NO. 128.

6. The antibody of claim 1, wherein the antibody is a single chain antibody, or fragment thereof, comprising: a heavy chain variable domain sequence that is at least 95% identical to an amino acid sequence selected from the group consisting of SEQ ID NO. 5, SEQ ID NO. 21, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, and SEQ ID NO. 127, and a light chain variable domain sequence that is at least 95% identical to an amino acid sequence selected from the group consisting of SEQ ID NO. 6, SEQ ID NO. 22, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128, wherein the heavy chain variable domain and the light chain variable domain are connected by a peptide linker.

7. The single chain antibody of claim 6, wherein the single chain antibody comprises a heavy chain/light chain variable domain sequence selected from the group consisting of SEQ ID NO. 5/SEQ ID NO. 6, SEQ ID NO. 21/SEQ ID NO. 22, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, and SEQ ID NO. 127/SEQ ID NO. 128.

8. The antibody of claim 2, wherein the antibody is selected from the group consisting of a Fab, a Fab', a F(ab')$_2$, an Fv, a domain antibody (dAb), a single-chain antibody, a chimeric antibody, a diabody, a triabody, a tetrabody, a fully human antibody, a humanized antibody, and a chimeric antibody.

9. The antibody of claim 8, wherein the antibody is an IgG.

10. The antibody of claim 1, wherein the antibody is selected from the group consisting of a Fab, a Fab', a F(ab')$_2$, an Fv, a domain antibody (dAb), a single-chain antibody, a chimeric antibody, a diabody, a triabody, a tetrabody, a fully human antibody, a humanized antibody, and a chimeric antibody.

11. The antibody of claim 10, wherein the antibody is a Fab.

12. The antibody of claim 10, wherein the antibody is a single chain antibody.

13. The antibody of claim 10, wherein the antibody is an IgG.

14. An antibody that binds to EGFR, the antibody comprising a heavy chain variable domain comprising an amino acid sequence selected from the group consisting of SEQ ID NO. 5, 21, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, and 127, and further comprising a light chain.

15. An antibody that binds to EGFR, the antibody comprising a light chain variable domain comprising an amino acid sequence selected from the group consisting of SEQ ID NO. 6, 22, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, and 128, and further comprising a heavy chain.

16. An antibody that binds to EGFR, the antibody comprising a heavy chain and a light chain, wherein the heavy chain/light chain variable domain sequence is selected from the group consisting of SEQ ID NO. 5/SEQ ID NO. 6, SEQ ID NO. 21/SEQ ID NO. 22, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, and SEQ ID NO. 127/SEQ ID NO. 128.

* * * * *

SEQUENCE LISTING

<160> NUMBER OF SEQ ID NOS: 128

<210> SEQ ID NO 1
<211> LENGTH: 120
<212> TYPE: PRT
<213> ORGANISM: Homo sapiens

<400> SEQUENCE: 1

Gln Val Thr Leu Arg Glu Ser Gly Pro Thr Leu Val Lys Pro Thr Gln
1               5                   10                  15

Thr Leu Thr Leu Thr Cys Thr Phe Ser Gly Phe Ser Leu Thr Ser Leu
            20                  25                  30

Ser Glu Ser Val Ala Trp Ile Arg Gln Ser Pro Gly Lys Ala Leu Glu
        35                  40                  45

Trp Leu Ala Leu Ile Tyr Trp Asp Asp Asp Lys Leu Tyr Ser Pro Ser
    50                  55                  60

Leu Lys Ser Arg Leu Thr Ile Thr Lys Asp Thr Ser Lys Asn Glu Val
65                  70                  75                  80

Val Leu Thr Met Thr Asn Val Asp Ser Ala Asp Thr Ala Thr Tyr Phe
                85                  90                  95

Cys Ala His Lys Lys Ile Arg Asp Thr Gly Phe Asp Phe Trp Gly Gln
            100                 105                 110

Gly Thr Leu Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Ser Tyr Glu Leu Met Gln Pro Pro Ser Val Ser Val Ala Pro Gly Met
1               5                   10                  15

Thr Ala Arg Ile Ser Cys Gly Ala Asn Asn Ile Gly Ser Glu Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Lys Ser Gly Asn Thr Ala Thr Leu Thr Ile Thr Arg Val Glu Ala Gly
65                  70                  75                  80

Asp Glu Ala Asp Tyr Tyr Cys Gln Val Trp Asp Ser Ser Thr Asp His
                85                  90                  95

Pro Val Phe Gly Gly Gly Thr Lys Leu Thr Val Leu
            100                 105

```
<210> SEQ ID NO 3
<211> LENGTH: 128
<212> TYPE: PRT
<213> ORGANISM: Homo sapiens

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Ile Pro Leu Glu Tyr Cys Thr Ser Thr Ser Cys Tyr
            100                 105                 110

His Ala Phe Asp Ile Trp Gly Gln Gly Thr Met Val Thr Val Ser Ser
        115                 120                 125

<210> SEQ ID NO 4
<211> LENGTH: 107
<212> TYPE: PRT
<213> ORGANISM: Homo sapiens

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Thr Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Tyr Ala Asn Leu Pro Leu
                85                  90                  95

Thr Phe Gly Pro Gly Thr Lys Val Asp Ile Lys
            100                 105

<210> SEQ ID NO 5
<211> LENGTH: 128
<212> TYPE: PRT
<213> ORGANISM: Homo sapiens

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Phe Ser Trp Val Arg Gln Ala Pro Gly Gln Gly Leu Glu Trp Met
        35                  40                  45

Gly Trp Ile Ser Ala Tyr Asn Gly Tyr Thr His Tyr Ala Glu Lys Leu
    50                  55                  60
```

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Val Ser Ala Ser Tyr Asn Ser Asp Trp Ser Leu His Tyr Tyr
            100                 105                 110

Tyr Gly Met Asp Val Trp Gly Gln Gly Thr Thr Val Thr Val Ser Ser
        115                 120                 125

<210> SEQ ID NO 6
<211> LENGTH: 110
<212> TYPE: PRT
<213> ORGANISM: Homo sapiens

<400> SEQUENCE: 6

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
            85                  90                  95

Ser Ala Gly Val Phe Gly Gly Gly Thr Lys Leu Thr Val Leu
            100                 105                 110

<210> SEQ ID NO 7
<211> LENGTH: 122
<212> TYPE: PRT
<213> ORGANISM: Homo sapiens

<400> SEQUENCE: 7

Glu Val Gln Leu Val Glu Ser Gly Gly Leu Val Lys Pro Gly Gly
1               5                   10                  15

Ser Leu Arg Leu Ser Cys Val Ser Gly Val Asp Thr Asn Ser Arg
            20                  25                  30

Ala Ile Ser Trp Val Arg Gln Ala Pro Gly Lys Gly Leu Glu Trp Val
        35                  40                  45

Ser Val Ile Tyr Ser Gly Gly Gly Thr Asn Tyr Ala Asp Ser Val
50                  55                  60

Lys Gly Arg Phe Thr Ile Ser Arg Asp Lys Ser Arg Asn Thr Val Phe
65                  70                  75                  80

Leu Gln Met Asn Ser Leu Arg Val Glu Asp Thr Ala Leu Tyr Tyr Cys
            85                  90                  95

Ala Lys Asp Pro Gly Trp Pro Ile Ala Gly Trp Tyr Phe Asp Leu Trp
            100                 105                 110

Gly Arg Gly Thr Leu Val Thr Val Ser Ser
        115                 120

<210> SEQ ID NO 8
<211> LENGTH: 108
<212> TYPE: PRT
<213> ORGANISM: Homo sapiens

<400> SEQUENCE: 8

Ser Tyr Glu Leu Met Gln Pro Ser Val Ser Val Ala Pro Gly Gln
1               5                   10                  15

Thr Ala Gly Ile Thr Cys Gly Gly Arg Asn Ile Gly Ser Lys Ser Val
            20                  25                  30

His Trp Tyr Gln Gln Lys Pro Gly Gln Ala Pro Leu Leu Val Ile Tyr
        35                  40                  45

Tyr Asp Asp Asp Arg Pro Ser Gly Ile Pro Glu Arg Phe Ser Gly Ser
    50                  55                  60

Asn Ser Glu Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp His
                85                  90                  95

Tyr Val Phe Gly Ala Gly Thr Lys Leu Thr Val Leu
            100                 105

<210> SEQ ID NO 9
<211> LENGTH: 127
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Arg Asn
            20                  25                  30

Asp Ile Asn Trp Val Arg Gln Ala Ser Gly Gln Gly Leu Glu Trp Ile
        35                  40                  45

Gly Trp Met Asn Pro Asn Thr Gly Ala Thr Ala Ser Ala Gln Asn Phe
    50                  55                  60

Gln Gly Arg Val Ala Met Thr Arg Asn Ala Ser Met Asn Thr Ala Tyr
65                  70                  75                  80

Leu Glu Leu Ser Gly Leu Arg Ser Asp Asp Thr Ala Ile Tyr Tyr Cys
                85                  90                  95

Ala Arg Ala Phe Glu Asp Tyr Ile Trp Glu Ser Ser Glu Phe His Phe
            100                 105                 110

Gly Leu Asp Val Trp Gly Gln Gly Thr Thr Val Thr Val Ser Ser
        115                 120                 125

<210> SEQ ID NO 10
<211> LENGTH: 110
<212> TYPE: PRT
<213> ORGANISM: Homo sapiens

<400> SEQUENCE: 10

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

His Tyr Ile Ser Trp Tyr Gln Gln His Pro Gly Lys Pro Pro Lys Leu
        35                  40                  45

Met Ile Phe Asp Val Ala Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Ser Ser Phe Ser Arg Asp
                85                  90                  95

Thr Asp Val Ile Phe Gly Gly Gly Thr Lys Leu Thr Val Leu
            100                 105                 110

<210> SEQ ID NO 11
<211> LENGTH: 120
<212> TYPE: PRT
<213> ORGANISM: Homo sapiens

<400> SEQUENCE: 11

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Asn His Tyr
            20                  25                  30

Ala Met His Trp Val Arg Gln Ala Pro Gly Lys Gly Leu Glu Trp Val
        35                  40                  45

Ala His Ile Ser Ser Asp Gly Ser Tyr Lys Tyr Ala Asp Ser Val
    50                  55                  60

Lys Gly Arg Phe Thr Val Ser Arg Asp Asn Ser Asp Asn Thr Val Tyr
65                  70                  75                  80

Leu Gln Met Asn Ser Leu Gly Pro Glu Asp Thr Ala Val Tyr His Cys
                85                  90                  95

Ala Arg Phe Thr Glu Val Leu Tyr Tyr Gly Ala Asp Tyr Trp Gly Gln
            100                 105                 110

Gly Thr Leu Val Thr Val Ser Ser
        115                 120

<210> SEQ ID NO 12
<211> LENGTH: 110
<212> TYPE: PRT
<213> ORGANISM: Homo sapiens

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 13
<211> LENGTH: 128
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser
1               5                   10                  15

Ala Val Lys Val Ser Cys Lys Ala Ser Gly Gly Thr Phe Ser Ser Tyr

```
            20                  25                  30
Ala Ile Ser Trp Val Arg Gln Ala Pro Gly Gln Gly Leu Glu Trp Met
        35                  40                  45
Gly Ile Ile Pro Ile Leu Gly Thr Ala Asp Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Glu Ile Pro Leu Glu Tyr Cys Thr Ser Thr Ser Cys Tyr
            100                 105                 110
His Ala Phe Asp Ile Trp Gly Gln Gly Thr Met Val Thr Val Ser Ser
        115                 120                 125
```

<210> SEQ ID NO 14
<211> LENGTH: 107
<212> TYPE: PRT
<213> ORGANISM: Homo sapiens

<400> SEQUENCE: 14

```
Asn Ile Gln Met Thr Gln Ser Pro Pro Ser Leu Ser Ala Phe Val Gly
1               5                   10                  15
Asp Arg Val Thr Ile Thr Cys Gln Ala Ser Gln Ala Ile Asn Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Asn Ala Thr Tyr Tyr Cys Gln Gln Tyr Asp Lys Leu Pro Leu
                85                  90                  95
Thr Phe Gly Gly Gly Thr Lys Val Glu Ile Lys
            100                 105
```

<210> SEQ ID NO 15
<211> LENGTH: 119
<212> TYPE: PRT
<213> ORGANISM: Homo sapiens

<400> SEQUENCE: 15

```
Gln Met Gln Leu Val Gln Ser Trp Ala Glu Val Lys Lys Pro Gly Ala
1               5                   10                  15
Ser Val Lys Val Ser Cys Lys Ala Ser Ala Tyr Thr Phe Thr Asn Tyr
            20                  25                  30
Tyr Ile His Trp Val Arg Gln Ala Pro Gly Gln Gly Leu Glu Trp Met
        35                  40                  45
Gly Ile Ile Asn Pro Ser Gly Ala Thr Thr Tyr Ala Gln Arg Leu
    50                  55                  60
Gln Gly Arg Val Ile Met Thr Arg Asp Thr Ser Thr Ser Thr Val Asn
65                  70                  75                  80
Met Glu Leu Ser Ser Leu Arg Ser Glu Asp Thr Ala Val Tyr Tyr Cys
                85                  90                  95
Ala Arg Ser Thr Leu Trp Phe Ser Glu Phe Asp Tyr Trp Gly Gln Gly
            100                 105                 110
Thr Leu Val Thr Val Ser Ser
```

```
<210> SEQ ID NO 16
<211> LENGTH: 110
<212> TYPE: PRT
<213> ORGANISM: Homo sapiens

<400> SEQUENCE: 16

Gln Ser Val Leu Thr Gln Pro Ala Ser Val Ser Gly Ser Pro Gly Gln
1               5                   10                  15

Ser Ile Thr Ile Ser Cys Thr Gly Thr Ser Asp Val Gly Gly Phe
                20                  25                  30

Asn Tyr Val Ser Trp Tyr Gln Gln His Pro Gly Lys Val Pro Lys Leu
            35                  40                  45

Ile Ile Phe Asp Val Ser Asn Arg Pro Ser Ser Val Ser Asp Arg Phe
50                  55                  60

Ser Gly Ser Lys Ser Val Asn Thr Ala Ser Leu Thr Ile Ser Gly Leu
65                  70                  75                  80

Gln Ala Glu Asp Glu Ala Asp Tyr Tyr Cys Ser Ser Tyr Thr Asp Ser
                85                  90                  95

Gly Ser Tyr Ile Phe Gly Thr Gly Thr Lys Val Thr Val Leu
            100                 105                 110

<210> SEQ ID NO 17
<211> LENGTH: 120
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Tyr Tyr Asp Ser Ser Leu Ser Phe Asp Tyr Trp Gly Gln
            100                 105                 110

Gly Thr Leu Val Thr Val Ser Ser
        115                 120

<210> SEQ ID NO 18
<211> LENGTH: 110
<212> TYPE: PRT
<213> ORGANISM: Homo sapiens

<400> SEQUENCE: 18

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45
```

Ile Ile Tyr Asp Val Thr Lys Arg Pro Ser Gly Phe Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Arg Val Phe Gly Thr Gly Thr Lys Val Thr Val Leu
            100                 105                 110

<210> SEQ ID NO 19
<211> LENGTH: 121
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Asn Trp Asn Tyr Gly Gly Gly Asp Tyr Trp Gly
            100                 105                 110

Gln Gly Thr Leu Val Thr Val Ser Ser
        115                 120

<210> SEQ ID NO 20
<211> LENGTH: 110
<212> TYPE: PRT
<213> ORGANISM: Homo sapiens

<400> SEQUENCE: 20

Ser Tyr Glu Leu Met Gln Pro Ala Ser Val Ser Gly Ser Pro Gly Gln
1               5                   10                  15

Ser Ile Thr Ile Ser Cys Thr Gly Thr Ser Ser Asp Ile Gly Asp Tyr
            20                  25                  30

Asn Tyr Val Ser Trp Tyr Gln Gln His Pro Gly Lys Ala Pro Lys Leu
        35                  40                  45

Ile Ile Tyr Asp Val Ser Ile Arg Pro Ser Gly Val Ser Leu Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Asn Thr
                85                  90                  95

Asp Thr Leu Glu Phe Gly Gly Gly Thr Lys Val Thr Val Leu
            100                 105                 110

<210> SEQ ID NO 21
<211> LENGTH: 120
<212> TYPE: PRT
<213> ORGANISM: Homo sapiens

<400> SEQUENCE: 21

Glu Val Gln Leu Val Glu Ser Gly Gly Val Val Gln Pro Gly Arg
1               5                   10                  15

Ser Leu Arg Leu Ser Cys Ala Ala Ser Gly Phe Ile Phe Asn His Tyr
            20                  25                  30

Ala Met His Trp Val Arg Gln Ala Pro Gly Lys Gly Leu Glu Trp Val
        35                  40                  45

Ala His Ile Ser Ser Asp Gly Ser Tyr Lys Phe Tyr Ala Asp Ser Val
    50                  55                  60

Lys Gly Arg Phe Thr Val Ser Arg Asp Asn Ser Asp Asn Thr Val Tyr
65                  70                  75                  80

Leu Gln Met Asn Ser Leu Gly Pro Glu Asp Thr Ala Val Tyr His Cys
                85                  90                  95

Ala Arg Phe Thr Glu Val Leu Tyr Tyr Gly Ala Asp Tyr Trp Gly Gln
            100                 105                 110

Gly Thr Leu Val Thr Val Ser Ser
        115                 120

<210> SEQ ID NO 22
<211> LENGTH: 110
<212> TYPE: PRT
<213> ORGANISM: Homo sapiens

<400> SEQUENCE: 22

Gln Ser Val Leu Thr Gln Pro Pro Ser Val Ser Glu Ala Pro Arg Gln
1               5                   10                  15

Arg Val Ser Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110

<210> SEQ ID NO 23
<211> LENGTH: 124
<212> TYPE: PRT
<213> ORGANISM: Homo sapiens

<400> SEQUENCE: 23

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Gly Ile Ile Trp Val Arg Gln Ala Pro Gly Gln Gly Leu Glu Trp Met
        35                  40                  45

Gly Trp Ile Asn Thr Asp Asn Gly Asn Thr Ile Tyr Ala Pro Lys Phe
    50                  55                  60

Gln Gly Arg Val Thr Met Thr Thr Asp Thr Ser Thr Ser Ile Val Tyr
65                  70                  75                  80

Met Glu Leu Gln Ser Leu Arg Ser Asp Asp Thr Ala Val Tyr Phe Cys
            85                  90                  95

Ser Arg Glu Asp Trp Asn Tyr Asp Gly Gly Leu Arg Glu Val Phe Asp
            100                 105                 110

Tyr Trp Gly Gln Gly Thr Leu Val Thr Val Ser Ser
            115                 120

<210> SEQ ID NO 24
<211> LENGTH: 110
<212> TYPE: PRT
<213> ORGANISM: Homo sapiens

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ala Asn Ile Gly Arg Asn
            20                  25                  30

Tyr Val Asn Trp Tyr Gln Gln Phe Pro Gly Thr Ala Pro Lys Leu Leu
        35                  40                  45

Met Tyr Ser Asn Asp Gln Ser Pro Ser Gly Val Arg Gly Arg Phe Ser
    50                  55                  60

Gly Ser Lys Ser Gly Thr Ser Ala Ser Leu Ala Ile Asn Gly Leu Gln
65                  70                  75                  80

Ser Glu Asp Glu Ala Asp Tyr Tyr Cys Ala Ala Trp Asp Asp Arg Leu
                85                  90                  95

Asn Ala Tyr Val Phe Gly Thr Gly Thr Lys Leu Thr Val Leu
            100                 105                 110

<210> SEQ ID NO 25
<211> LENGTH: 128
<212> TYPE: PRT
<213> ORGANISM: Homo sapiens

<400> SEQUENCE: 25

Glu Val Gln Leu Val Gln Ser Gly Ala Glu Val Lys Lys Pro Gly Ser
1               5                   10                  15

Ala Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Ile Pro Leu Glu Tyr Cys Thr Ser Thr Ser Cys Tyr
            100                 105                 110

His Ala Phe Asp Ile Trp Gly Arg Gly Thr Met Val Thr Val Ser Ser
        115                 120                 125

<210> SEQ ID NO 26
<211> LENGTH: 107
<212> TYPE: PRT
<213> ORGANISM: Homo sapiens

<400> SEQUENCE: 26

Ala Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 27
<211> LENGTH: 118
<212> TYPE: PRT
<213> ORGANISM: Homo sapiens

<400> SEQUENCE: 27

Gln Val Gln Leu Val Glu Ser Gly Gly Gly Leu Val Gln Pro Gly Gly
1               5                   10                  15

Ser Leu Arg Leu Phe Cys Ala Ala Ser Gly Phe Gly Val Ser Thr Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ala Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Lys Glu Ser Pro Asn Asp Asp Tyr Phe Asp Tyr Trp Gly Gln Gly Thr
            100                 105                 110

Leu Val Thr Val Ser Ser
        115

<210> SEQ ID NO 28
<211> LENGTH: 107
<212> TYPE: PRT
<213> ORGANISM: Homo sapiens

<400> SEQUENCE: 28

Ala Ile Arg Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Glu Ala Pro Lys Leu Leu Ile
        35                  40                  45

Tyr Gly Ala Ser Asn Leu Gln Ser Gly Val Pro Ile Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Phe Cys Gln Gln Ser His Gly Ala Pro Tyr
                85                  90                  95

Thr Phe Gly Gln Gly Thr Lys Val Glu Ile Lys
            100                 105

```
<210> SEQ ID NO 29
<211> LENGTH: 128
<212> TYPE: PRT
<213> ORGANISM: Homo sapiens

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Glu Tyr Cys Ser Gly Gly Thr Cys Tyr Ser Ala
            100                 105                 110

Asp Ala Phe Asp Ile Trp Gly Gln Gly Thr Met Val Thr Val Ser Ser
        115                 120                 125

<210> SEQ ID NO 30
<211> LENGTH: 110
<212> TYPE: PRT
<213> ORGANISM: Homo sapiens

<400> SEQUENCE: 30

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Glu Asn Tyr
            20                  25                  30

Ser Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Arg Leu
                85                  90                  95

Ser Ser Val Val Phe Gly Gly Gly Thr Lys Val Thr Val Leu
            100                 105                 110

<210> SEQ ID NO 31
<211> LENGTH: 120
<212> TYPE: PRT
<213> ORGANISM: Homo sapiens

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
```

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Glu Ala Pro Ile Ala Ala Ala Phe Asp Ile Trp Gly Gln
                100                 105                 110

Gly Thr Met Val Thr Val Ser Ser
            115                 120

<210> SEQ ID NO 32
<211> LENGTH: 106
<212> TYPE: PRT
<213> ORGANISM: Homo sapiens

<400> SEQUENCE: 32

Asp Ile Val Met Thr Gln Ser Pro Val Ser Leu Ser Ala Ser Val Gly
 1               5                  10                  15

Asp Ser Val Thr Ile Thr Cys Arg Ala Ser Gln Ser Ile Ser Ser Tyr
                 20                  25                  30

Leu Asn Trp Tyr Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Leu Tyr Thr
                 85                  90                  95

Phe Gly Gln Gly Thr Lys Leu Glu Ile Lys
            100                 105

<210> SEQ ID NO 33
<211> LENGTH: 117
<212> TYPE: PRT
<213> ORGANISM: Homo sapiens

<400> SEQUENCE: 33

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Pro Ile Ser Trp Val Arg Gln Ala Pro Gly Gln Gly Leu Glu Trp Met
             35                  40                  45

Gly Gly Ile Ile Pro Ile Phe Gly Ile Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Ser Gly Tyr Ser Leu Tyr Trp Gly Gln Gly Thr Leu
                100                 105                 110

Val Thr Val Ser Ser
            115

<210> SEQ ID NO 34
<211> LENGTH: 110
<212> TYPE: PRT
```

<213> ORGANISM: Homo sapiens

<400> SEQUENCE: 34

Gln Ser Val Leu Thr Gln Pro Pro Ser Ala Ser Gly Ser Pro Gly Gln
1               5                   10                  15

Ser Val Thr Ile Ser Cys Thr Gly Ala Arg Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
                100                 105                 110

<210> SEQ ID NO 35
<211> LENGTH: 119
<212> TYPE: PRT
<213> ORGANISM: Homo sapiens

<400> SEQUENCE: 35

Gln Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Trp Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Ile Gln Thr Ser Ser Ser Asp Ala Phe Asp Ile Trp Gly Gln Gly
                100                 105                 110

Thr Met Val Thr Val Ser Ser
        115

<210> SEQ ID NO 36
<211> LENGTH: 107
<212> TYPE: PRT
<213> ORGANISM: Homo sapiens

<400> SEQUENCE: 36

Asp Val Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Asn Thr Tyr
                20                  25                  30

Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

-continued

Glu Asp Phe Ala Thr Tyr Tyr Cys Gln Gln Thr Tyr Ser Thr Pro Phe
                85                  90                  95

Thr Phe Gly Pro Gly Thr Lys Val Asp Ile Lys
            100                 105

<210> SEQ ID NO 37
<211> LENGTH: 121
<212> TYPE: PRT
<213> ORGANISM: Homo sapiens

<400> SEQUENCE: 37

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ala Ser Asn
            20                  25                  30

Gly Ala Ser Trp Asn Trp Ile Arg Gln Ser Pro Ser Arg Gly Leu Glu
        35                  40                  45

Trp Leu Ser Lys Thr Tyr Tyr Arg Ser Lys Trp Tyr Tyr Glu Tyr Ala
    50                  55                  60

Pro Ser Val Thr Ser Arg Met Thr Ile Ser Pro Asp Thr Ser Lys Asn
65                  70                  75                  80

Gln Phe Ser Leu Gln Val Thr Ser Val Thr Pro Glu Asp Thr Ala Val
                85                  90                  95

Tyr Tyr Cys Ala Arg Leu Ile Gly Asp Gly Leu Ile Asp Tyr Trp Gly
            100                 105                 110

Gln Gly Thr Leu Val Thr Val Ser Ser
        115                 120

<210> SEQ ID NO 38
<211> LENGTH: 113
<212> TYPE: PRT
<213> ORGANISM: Homo sapiens

<400> SEQUENCE: 38

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Gly Gly Thr Lys Val Glu Ile
            100                 105                 110

Lys

<210> SEQ ID NO 39
<211> LENGTH: 120
<212> TYPE: PRT
<213> ORGANISM: Homo sapiens

<400> SEQUENCE: 39

Gln Val Thr Leu Arg Glu Ser Gly Pro Thr Leu Val Lys Pro Thr Gln

-continued

```
1               5                   10                  15
Thr Leu Thr Leu Thr Cys Thr Phe Ser Gly Phe Ser Leu Thr Ser Leu
                20                  25                  30

Ser Glu Ser Val Ala Trp Ile Arg Gln Ser Pro Gly Lys Ala Leu Glu
            35                  40                  45

Trp Leu Ala Leu Ile Tyr Trp Asp Asp Lys Leu Tyr Ser Pro Ser
        50                  55                  60

Leu Lys Ser Arg Leu Thr Ile Thr Lys Asp Thr Ser Lys Asn Glu Val
65                  70                  75                  80

Val Leu Thr Met Thr Asn Val Asp Ser Ala Asp Thr Ala Thr Tyr Phe
                85                  90                  95

Cys Ala His Lys Lys Ile Arg Asp Thr Gly Phe Asp Phe Trp Gly Gln
                100                 105                 110

Gly Thr Leu Val Thr Val Ser Ser
            115                 120
```

<210> SEQ ID NO 40
<211> LENGTH: 108
<212> TYPE: PRT
<213> ORGANISM: Homo sapiens

<400> SEQUENCE: 40

```
Gln Ala Val Val Thr Gln Pro Pro Ser Ala Ser Val Ala Pro Gly Gln
1               5                   10                  15

Thr Ala Arg Ile Thr Cys Glu Gly Asn Asn Ile Glu Ser Lys Ser Val
                20                  25                  30

His Trp Tyr Gln Gln Lys Pro Gly Gln Ala Pro Val Leu Val Ile Tyr
            35                  40                  45

Tyr Asp Arg Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu
                100                 105
```

<210> SEQ ID NO 41
<211> LENGTH: 122
<212> TYPE: PRT
<213> ORGANISM: Homo sapiens

<400> SEQUENCE: 41

```
Glu Val Gln Leu Val Glu Ser Gly Gly Gly Leu Val Lys Pro Gly Gly
1               5                   10                  15

Ser Leu Arg Leu Ser Cys Val Gly Ser Gly Val Asp Thr Asn Ser Arg
                20                  25                  30

Ala Ile Ser Trp Val Arg Gln Ala Pro Gly Lys Gly Leu Glu Trp Val
            35                  40                  45

Ser Val Ile Tyr Ser Gly Gly Gly Thr Asn Tyr Ala Asp Ser Val
        50                  55                  60

Lys Gly Arg Phe Thr Ile Ser Arg Asp Lys Ser Arg Asn Thr Val Phe
65                  70                  75                  80

Leu Gln Met Asn Ser Leu Arg Val Glu Asp Thr Ala Leu Tyr Tyr Cys
                85                  90                  95

Ala Lys Asp Pro Gly Trp Pro Ile Ala Gly Trp Tyr Phe Asp Leu Trp
```

-continued

```
                100                 105                 110
Gly Arg Gly Thr Leu Val Thr Val Ser Ser
            115                 120

<210> SEQ ID NO 42
<211> LENGTH: 108
<212> TYPE: PRT
<213> ORGANISM: Homo sapiens

<400> SEQUENCE: 42

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Leu Thr Val Arg
            100                 105

<210> SEQ ID NO 43
<211> LENGTH: 125
<212> TYPE: PRT
<213> ORGANISM: Homo sapiens

<400> SEQUENCE: 43

Gln Val Gln Leu Gln Gln Ser Gly Pro Gly Leu Val Gln Pro Ser Gln
1               5                   10                  15

Thr Leu Ser Leu Thr Cys Ala Ile Ser Gly Asp Thr Val Ser Thr Asn
            20                  25                  30

Tyr His Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Val Thr Ile Ser Pro Asp Thr Ser Lys Asn
65                  70                  75                  80

His Phe Ser Leu Gln Leu Lys Ser Val Thr Pro Glu Asp Thr Ala Val
                85                  90                  95

Tyr Tyr Cys Ala Arg Asp Gly Gly Thr Thr Asn Tyr Tyr Asn Val Phe
            100                 105                 110

Asp Val Trp Gly Gln Gly Thr Thr Val Thr Val Ser Ser
        115                 120                 125

<210> SEQ ID NO 44
<211> LENGTH: 109
<212> TYPE: PRT
<213> ORGANISM: Homo sapiens

<400> SEQUENCE: 44

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30
```

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

His Val Val Phe Gly Gly Gly Thr Lys Leu Thr Val Leu
                100                 105

<210> SEQ ID NO 45
<211> LENGTH: 119
<212> TYPE: PRT
<213> ORGANISM: Homo sapiens

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Leu
            35                  40                  45

Gly Trp Ile Asn Pro Ser Ser Gly Phe Thr Asp Tyr Ala His Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Glu Phe Asp Tyr Trp Gly Gln Gly
                100                 105                 110

Thr Leu Val Thr Val Ser Ser
        115

<210> SEQ ID NO 46
<211> LENGTH: 111
<212> TYPE: PRT
<213> ORGANISM: Homo sapiens

<400> SEQUENCE: 46

Gln Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Tyr
                20                  25                  30

Thr Val Asn Trp Tyr Gln Gln Leu Pro Gly Thr Ala Pro Lys Leu Leu
            35                  40                  45

Ile Tyr Asn Asn Asn Glu Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Arg Leu
                85                  90                  95

Ser Gly Asp Val Ile Phe Gly Gly Gly Thr Lys Leu Thr Val Leu
                100                 105                 110

<210> SEQ ID NO 47

```
<211> LENGTH: 120
<212> TYPE: PRT
<213> ORGANISM: Homo sapiens

<400> SEQUENCE: 47

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

His Ile His Trp Val Arg Gln Ala Pro Gly Gln Gly Leu Glu Trp Met
            35                  40                  45

Gly Trp Ile Asn Thr Tyr Asn Gly Asn Thr Gln Tyr Ala Gln His Val
        50                  55                  60

Gln Asp Arg Val Thr Met Thr Arg Asp Ser Ala Thr Ser Ser Val Tyr
65                  70                  75                  80

Leu Glu Leu Arg Ser Leu Arg Ser Asp Asp Thr Ala Leu Tyr Phe Cys
                85                  90                  95

Ala Leu Pro Asn Asp Tyr Tyr Ser Tyr Ala Met Asp Val Trp Gly Gln
                100                 105                 110

Gly Thr Thr Val Thr Val Ser Ser
            115                 120

<210> SEQ ID NO 48
<211> LENGTH: 107
<212> TYPE: PRT
<213> ORGANISM: Homo sapiens

<400> SEQUENCE: 48

Asp Val Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Gln Val Tyr Pro Thr
                85                  90                  95

Thr Phe Gly Gln Gly Thr Arg Leu Glu Ile Lys
                100                 105

<210> SEQ ID NO 49
<211> LENGTH: 123
<212> TYPE: PRT
<213> ORGANISM: Homo sapiens

<400> SEQUENCE: 49

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Asn Asp Gly Ser Thr Thr Tyr Ala Gln Asn Phe
        50                  55                  60
```

Gln Gly Arg Ile Thr Met Thr Arg Asp Thr Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Ser Ser Leu Gly Gly Tyr Tyr Tyr Gly Met Asp Val
            100                 105                 110

Trp Gly Gln Gly Thr Thr Val Thr Val Ser Ser
            115                 120

<210> SEQ ID NO 50
<211> LENGTH: 108
<212> TYPE: PRT
<213> ORGANISM: Homo sapiens

<400> SEQUENCE: 50

Leu Pro Val Leu Thr Gln Pro Pro Ser Val Ser Val Ala Pro Gly Glu
1               5                   10                  15

Thr Ala Lys Ile Thr Cys Gly Gly Thr Tyr Ile Val Arg Lys Ile Val
            20                  25                  30

His Trp Tyr Gln Gln Lys Pro Gly Gln Ala Pro Arg Leu Val Ile Tyr
        35                  40                  45

Tyr Asp Ala Ala Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Asn Ser Asp His
                85                  90                  95

Tyr Val Phe Gly Pro Gly Thr Lys Val Thr Val Leu
            100                 105

<210> SEQ ID NO 51
<211> LENGTH: 118
<212> TYPE: PRT
<213> ORGANISM: Homo sapiens

<400> SEQUENCE: 51

Gln Val Gln Leu Gln Gln Trp Ala Glu Val Lys Lys Pro Gly Ala Ser
1               5                   10                  15

Val Lys Val Ser Cys Lys Ala Ser Gly Tyr Thr Phe Thr Asp His Tyr
            20                  25                  30

Ile Asp Trp Val Arg Gln Ala Pro Gly Gln Gly Leu Glu Trp Met Gly
        35                  40                  45

Arg Ile Asn Pro Asn Ser Gly Tyr Thr Asn Tyr Ala Gln Thr Phe Gln
    50                  55                  60

Gly Arg Val Thr Met Thr Arg Asp Thr Ser Ile Asn Thr Ala Tyr Met
65                  70                  75                  80

Asp Leu Ser Ser Leu Arg Ser Glu Asp Thr Ala Val Tyr Tyr Cys Ala
                85                  90                  95

Arg Ser Thr Leu Trp Phe Ser Glu Phe Asp Tyr Trp Gly Gln Gly Thr
            100                 105                 110

Leu Val Thr Val Ser Ser
        115

<210> SEQ ID NO 52
<211> LENGTH: 110
<212> TYPE: PRT
<213> ORGANISM: Homo sapiens -continued

```
<400> SEQUENCE: 52

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ser Tyr Val Phe Gly Thr Gly Thr Lys Val Thr Val Leu
            100                 105                 110

<210> SEQ ID NO 53
<211> LENGTH: 125
<212> TYPE: PRT
<213> ORGANISM: Homo sapiens

<400> SEQUENCE: 53

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Phe Asp Gly Asn Asn Lys Tyr Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Tyr Tyr Asp Ile Leu Thr Gly Tyr Tyr Tyr Gly Met
            100                 105                 110

Asp Val Trp Gly Gln Gly Thr Thr Val Thr Val Ser Ser
        115                 120                 125

<210> SEQ ID NO 54
<211> LENGTH: 108
<212> TYPE: PRT
<213> ORGANISM: Homo sapiens

<400> SEQUENCE: 54

Gln Ser Ala Leu Thr Gln Pro Ala Ser Val Ser Val Ala Pro Gly Thr
1               5                   10                  15

Thr Ala Arg Ile Thr Cys Gly Gly Ser Asn Ile Ala Arg Lys Asn Val
            20                  25                  30

His Trp Tyr Gln Gln Lys Pro Gly Gln Ala Pro Leu Val Val Val Ser
        35                  40                  45

Asp Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
```

```
                    85                  90                  95

Pro Val Phe Gly Gly Gly Thr Lys Leu Thr Val Leu
            100                 105

<210> SEQ ID NO 55
<211> LENGTH: 122
<212> TYPE: PRT
<213> ORGANISM: Homo sapiens

<400> SEQUENCE: 55

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Ser Tyr Tyr Asp Pro Tyr Tyr Gly Met Asp Val Trp
            100                 105                 110

Gly Gln Gly Thr Thr Val Thr Val Ser Ser
        115                 120

<210> SEQ ID NO 56
<211> LENGTH: 110
<212> TYPE: PRT
<213> ORGANISM: Homo sapiens

<400> SEQUENCE: 56

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Val Val Phe Gly Gly Gly Thr Lys Leu Thr Val Leu
            100                 105                 110

<210> SEQ ID NO 57
<211> LENGTH: 118
<212> TYPE: PRT
<213> ORGANISM: Homo sapiens

<400> SEQUENCE: 57

Val Gln Leu Val Gln Ser Gly Ala Glu Val Lys Asn Pro Gly Ala Ser
1               5                   10                  15

Val Lys Val Ser Cys Lys Ala Ser Gly Phe Thr Phe Thr Ser Tyr Asp
            20                  25                  30
```

```
Leu Asn Trp Val Arg Gln Ala Pro Gly Gln Gly Leu Glu Trp Met Gly
            35                  40                  45

Trp Met Asn Pro Ile Asn Gly Asn Thr Gly Tyr Ala Gln Lys Phe Gln
 50                  55                  60

Gly Arg Val Ser Met Thr Arg Asp Thr Ser Thr Ser Thr Val Tyr Met
 65                  70                  75                  80

Glu Leu Ser Ser Leu Arg Ser Glu Asp Thr Ala Val Tyr Tyr Cys Ala
                85                  90                  95

Arg Ala Asp Leu Trp Phe Gly Glu Leu Asp Tyr Trp Gly Gln Gly Thr
                100                 105                 110

Leu Val Thr Val Ser Ser
            115
```

<210> SEQ ID NO 58
<211> LENGTH: 107
<212> TYPE: PRT
<213> ORGANISM: Homo sapiens

<400> SEQUENCE: 58

```
Asp Ile Gln Leu Thr Gln Ser Pro Ser Ser Leu Ser Ala Ser Val Gly
 1               5                  10                  15

Asp Arg Val Thr Ile Ala Cys Arg Ala Ser Gln Ser Ile Ser Ser Tyr
                20                  25                  30

Leu Asn Trp Tyr Gln Lys Lys Val Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Val
                85                  90                  95

Thr Phe Gly Gln Gly Thr Lys Val Glu Ile Lys
                100                 105
```

<210> SEQ ID NO 59
<211> LENGTH: 128
<212> TYPE: PRT
<213> ORGANISM: Homo sapiens

<400> SEQUENCE: 59

```
Glu Val Gln Leu Val Gln Ser Gly Ala Glu Val Lys Lys Pro Gly Ala
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Leu Gly Thr Ala Asp Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Glu Ile Pro Leu Glu Tyr Cys Thr Ser Thr Ser Cys Tyr
                100                 105                 110

His Ala Phe Asp Ile Trp Gly Gln Gly Thr Met Val Thr Val Ser Ser
            115                 120                 125
```

<210> SEQ ID NO 60
<211> LENGTH: 107
<212> TYPE: PRT
<213> ORGANISM: Homo sapiens

<400> SEQUENCE: 60

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Thr Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Tyr Ala Asn Leu Pro Leu
                85                  90                  95

Thr Phe Gly Pro Gly Thr Lys Val Asp Ile Lys
            100                 105

<210> SEQ ID NO 61
<211> LENGTH: 127
<212> TYPE: PRT
<213> ORGANISM: Homo sapiens

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Trp Ser Trp Val Arg Gln Ala Pro Gly Gln Gly Leu Glu Trp Met
        35                  40                  45

Gly Trp Ile Ser Ala Tyr Asn Gly Tyr Thr His Tyr Ala Ser Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Ala Glu Asp Trp Ser Leu His Tyr Tyr
            100                 105                 110

Tyr Met Asp Val Trp Gly Gln Gly Thr Leu Val Thr Val Ser Ser
        115                 120                 125

<210> SEQ ID NO 62
<211> LENGTH: 110
<212> TYPE: PRT
<213> ORGANISM: Homo sapiens

<400> SEQUENCE: 62

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

```
Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Ser Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 63
<211> LENGTH: 128
<212> TYPE: PRT
<213> ORGANISM: Homo sapiens

<400> SEQUENCE: 63

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Asn His
                20                  25                  30

Ala Trp Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Ser Lys Leu
    50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Val Ser Ala Ser Tyr Asn Glu Asp Trp Ser Leu His Tyr Tyr
                100                 105                 110

Tyr Gly Met Asp Val Trp Gly Gln Gly Thr Leu Val Thr Val Ser Ser
            115                 120                 125

<210> SEQ ID NO 64
<211> LENGTH: 110
<212> TYPE: PRT
<213> ORGANISM: Homo sapiens

<400> SEQUENCE: 64

Gln Ser Val Leu Thr Gln Pro Pro Ser Val Ser Ala Ala Pro Gly Gln
 1               5                  10                  15

Glu Val Thr Ile Ser Cys Ser Gly Ser Asn Ser Asn Ile Glu Pro Asn
                20                  25                  30

Tyr Val Ser Trp Tyr Gln Gln Leu Pro Gly Thr Ala Pro Lys Leu Leu
            35                  40                  45

Ile Tyr Ser Thr Ala Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Ser Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 65
<211> LENGTH: 128
<212> TYPE: PRT
<213> ORGANISM: Homo sapiens
```

```
<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr Thr Tyr Ala Ser Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Ser Tyr Asn Ser Asp Trp Ser Leu His Tyr Tyr
            100                 105                 110

Tyr Gly Met Asp Val Trp Gly Gln Gly Thr Leu Val Thr Val Ser Ser
        115                 120                 125

<210> SEQ ID NO 66
<211> LENGTH: 110
<212> TYPE: PRT
<213> ORGANISM: Homo sapiens

<400> SEQUENCE: 66

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Ser Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Phe Asp Ser Ser Leu
                85                  90                  95

Ser Ala Val Val Phe Gly Gly Gly Thr Lys Leu Thr Val Leu
            100                 105                 110

<210> SEQ ID NO 67
<211> LENGTH: 128
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr His Tyr Ala Ser Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                    85                  90                  95

Ala Arg Val Ser Ala Ser Tyr Ala Ser Asp Trp Ser Leu His Tyr Tyr
                100                 105                 110

Tyr Gly Met Asp Val Trp Gly Gln Gly Thr Leu Val Thr Val Ser Ser
                115                 120                 125

<210> SEQ ID NO 68
<211> LENGTH: 110
<212> TYPE: PRT
<213> ORGANISM: Homo sapiens

<400> SEQUENCE: 68

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Thr Ala Glu Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Val Leu Phe Gly Gly Gly Thr Lys Leu Thr Val Leu
                100                 105                 110

<210> SEQ ID NO 69
<211> LENGTH: 128
<212> TYPE: PRT
<213> ORGANISM: Homo sapiens

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
                20                  25                  30

Ala Tyr Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Ser Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Asn Ser Asp Trp Ser Leu His Tyr Tyr
                100                 105                 110

Tyr Gly Met Asp Val Trp Gly Gln Gly Thr Leu Val Thr Val Ser Ser
                115                 120                 125

<210> SEQ ID NO 70
<211> LENGTH: 110
<212> TYPE: PRT
<213> ORGANISM: Homo sapiens

<400> SEQUENCE: 70

Gln Ser Val Leu Thr Gln Pro Pro Ser Val Ser Ala Ala Pro Gly Gln
1               5                   10                  15
```

-continued

Glu Val Thr Ile Ser Cys Ser Gly Ser Asn Ser Asn Ile Pro Asn Asn
            20                  25                  30

Tyr Val Ser Trp Tyr Gln Gln Leu Pro Gly Thr Ala Pro Lys Leu Leu
        35                  40                  45

Ile Tyr Ser Asn Tyr Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Val Val Phe Gly Gly Gly Thr Lys Leu Thr Val Leu
            100                 105                 110

<210> SEQ ID NO 71
<211> LENGTH: 128
<212> TYPE: PRT
<213> ORGANISM: Homo sapiens

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr His Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Asn Ser Asp Trp Ser Val His Tyr Tyr
            100                 105                 110

Tyr Gly Met Asp Val Trp Gly Gln Gly Thr Leu Val Thr Val Ser Ser
        115                 120                 125

<210> SEQ ID NO 72
<211> LENGTH: 110
<212> TYPE: PRT
<213> ORGANISM: Homo sapiens

<400> SEQUENCE: 72

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Pro Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Phe Asp Ser Ser Leu
                85                  90                  95

Ser Ala Ala Val Phe Gly Gly Gly Thr Lys Leu Thr Val Leu
            100                 105                 110

<210> SEQ ID NO 73
<211> LENGTH: 128
<212> TYPE: PRT
<213> ORGANISM: Homo sapiens

<400> SEQUENCE: 73

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr Thr Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Ala Glu Asp Trp Ser Leu His Tyr Tyr
            100                 105                 110

Tyr Gly Met Asp Val Trp Gly Gln Gly Thr Leu Val Thr Val Ser Ser
        115                 120                 125
```

<210> SEQ ID NO 74
<211> LENGTH: 110
<212> TYPE: PRT
<213> ORGANISM: Homo sapiens

<400> SEQUENCE: 74

```
Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Pro Asn Asn
            20                  25                  30

Tyr Val Ser Trp Tyr Gln Gln Leu Pro Gly Thr Ala Pro Lys Leu Leu
        35                  40                  45

Ile Tyr Ser Asn Ser Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Ala Leu Phe Gly Gly Gly Thr Lys Leu Thr Val Leu
            100                 105                 110
```

<210> SEQ ID NO 75
<211> LENGTH: 120
<212> TYPE: PRT
<213> ORGANISM: Homo sapiens

<400> SEQUENCE: 75

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45
```

```
Ala His Ile Ser Ser Asp Gly Ser Ser Lys Phe Tyr Ala Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Thr Glu Val Leu Tyr Tyr Gly Ala Asp Leu Trp Gly Gln
             100                 105                 110

Gly Thr Leu Val Thr Val Ser Ser
             115                 120
```

<210> SEQ ID NO 76
<211> LENGTH: 110
<212> TYPE: PRT
<213> ORGANISM: Homo sapiens

<400> SEQUENCE: 76

```
Gln Ser Val Leu Thr Gln Pro Pro Ser Val Ser Glu Ala Pro Arg Gln
 1               5                  10                  15

Arg Val Ser Ile Ser Cys Ser Gly Ser Ser Ser Asn Ile Gly Asn Asn
             20                  25                  30

Ala Val Asn Trp Tyr Gln Gln Leu Pro Gly Lys Ala Pro Lys Leu Leu
         35                  40                  45

Ile Tyr Phe Asp Asp Leu Leu Pro Leu Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Lys Gly Tyr Val Phe Gly Thr Gly Thr Lys Val Thr Val Leu
             100                 105                 110
```

<210> SEQ ID NO 77
<211> LENGTH: 120
<212> TYPE: PRT
<213> ORGANISM: Homo sapiens

<400> SEQUENCE: 77

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Ile Phe His His Tyr
             20                  25                  30

Ala Met His Trp Val Arg Gln Ala Pro Gly Lys Gly Leu Glu Trp Val
         35                  40                  45

Ala His Ile Ser Pro Asp Gly Ser Ser Lys Phe Tyr Ala Asp Ser Val
 50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Thr Glu Val Leu Tyr Tyr Gly Ala Asp Ile Trp Gly Gln
             100                 105                 110

Gly Thr Leu Val Thr Val Ser Ser
             115                 120
```

<210> SEQ ID NO 78
<211> LENGTH: 110

```
<212> TYPE: PRT
<213> ORGANISM: Homo sapiens

<400> SEQUENCE: 78

Gln Ser Val Leu Thr Gln Pro Pro Ser Val Ser Glu Ala Pro Arg Gln
1               5                   10                  15

Arg Val Ser Ile Ser Cys Ser Gly Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Phe Asp Asp Leu Leu Pro Ser Gly Val Ser Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
                100                 105                 110

<210> SEQ ID NO 79
<211> LENGTH: 120
<212> TYPE: PRT
<213> ORGANISM: Homo sapiens

<400> SEQUENCE: 79

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
                20                  25                  30

Ala Met His Trp Val Arg Gln Ala Pro Gly Lys Gly Leu Glu Trp Val
            35                  40                  45

Ala His Ile Ser Ser Asp Gly Ser Ser Lys Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Leu Trp Gly Gln
                100                 105                 110

Gly Thr Leu Val Thr Val Ser Ser
            115                 120

<210> SEQ ID NO 80
<211> LENGTH: 110
<212> TYPE: PRT
<213> ORGANISM: Homo sapiens

<400> SEQUENCE: 80

Gln Ser Val Leu Thr Gln Pro Pro Ser Val Ser Glu Ala Pro Arg Gln
1               5                   10                  15

Arg Val Ser Ile Ser Cys Ser Gly Ser Ser Asn Ile Gly Asp Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu His Pro Ser Gly Val Ser Asp Arg Phe Ser
        50                  55                  60

Gly Ser Lys Ser Gly Thr Ser Ala Ser Leu Ala Ile Ser Gly Leu Gln
```

```
                65                  70                  75                  80
Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110
```

<210> SEQ ID NO 81
<211> LENGTH: 120
<212> TYPE: PRT
<213> ORGANISM: Homo sapiens

<400> SEQUENCE: 81

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
                20                  25                  30

Ala Met His Trp Val Arg Gln Ala Pro Gly Lys Gly Leu Glu Trp Val
            35                  40                  45

Ala His Ile Ser Ile Asp Gly Ser Ser Lys Phe Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Leu Trp Gly Gln
            100                 105                 110

Gly Thr Leu Val Thr Val Ser Ser
        115                 120
```

<210> SEQ ID NO 82
<211> LENGTH: 110
<212> TYPE: PRT
<213> ORGANISM: Homo sapiens

<400> SEQUENCE: 82

```
Gln Ser Val Leu Thr Gln Pro Pro Ser Val Ser Glu Ala Pro Arg Gln
1               5                   10                  15

Arg Val Ser Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110
```

<210> SEQ ID NO 83
<211> LENGTH: 128
<212> TYPE: PRT
<213> ORGANISM: Homo sapiens

<400> SEQUENCE: 83

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Arg Asn His
             20                  25                  30

Ala Tyr Ser Trp Val Arg Gln Ala Pro Gly Gln Gly Leu Glu Trp Met
         35                  40                  45

Gly Trp Ile Ser Ala Tyr Asn Gly Tyr Thr Thr Tyr Ala Glu Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                 85                  90                  95

Ala Arg Val Ser Ala Glu Tyr Asn Ser Asp Trp Ser Val His Tyr Tyr
            100                 105                 110

Tyr Gly Met Asp Val Trp Gly Gln Gly Thr Leu Val Thr Val Ser Ser
        115                 120                 125
```

<210> SEQ ID NO 84
<211> LENGTH: 110
<212> TYPE: PRT
<213> ORGANISM: Homo sapiens

<400> SEQUENCE: 84

```
Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Ser Thr Asn Glu Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                 85                  90                  95

Ser Ala Gly Val Phe Gly Gly Gly Thr Lys Leu Thr Val Leu
            100                 105                 110
```

<210> SEQ ID NO 85
<211> LENGTH: 128
<212> TYPE: PRT
<213> ORGANISM: Homo sapiens

<400> SEQUENCE: 85

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
             20                  25                  30

Ala Trp Ser Trp Val Arg Gln Ala Pro Gly Gln Gly Leu Glu Trp Met
         35                  40                  45

Gly Trp Ile Ser Ala Tyr Asn Gly Tyr Thr Thr Tyr Ala Ser Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                 85                  90                  95

Ala Arg Val Ser Ala Glu Tyr Ala Ser Asp Trp Ser Leu His Tyr Tyr
            100                 105                 110
```

Tyr Gly Met Asp Val Trp Gly Gln Gly Thr Leu Val Thr Val Ser Ser
        115                 120                 125

<210> SEQ ID NO 86
<211> LENGTH: 110
<212> TYPE: PRT
<213> ORGANISM: Homo sapiens

<400> SEQUENCE: 86

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Arg Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 87
<211> LENGTH: 128
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr Thr Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Asn Ser Asp Trp Ser Val His Tyr Tyr
            100                 105                 110

Tyr Gly Met Asp Val Trp Gly Gln Gly Thr Leu Val Thr Val Ser Ser
        115                 120                 125

<210> SEQ ID NO 88
<211> LENGTH: 110
<212> TYPE: PRT
<213> ORGANISM: Homo sapiens

<400> SEQUENCE: 88

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Glu Pro Asn
            20                  25                  30

```
Tyr Val Ser Trp Tyr Gln Gln Leu Pro Gly Thr Ala Pro Lys Leu Leu
            35                  40                  45

Ile Tyr Ser Thr Tyr Glu Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Phe Asp Ser Ser Leu
                 85                  90                  95

Ser Ala Ala Val Phe Gly Gly Gly Thr Lys Leu Thr Val Leu
                100                 105                 110

<210> SEQ ID NO 89
<211> LENGTH: 128
<212> TYPE: PRT
<213> ORGANISM: Homo sapiens

<400> SEQUENCE: 89

Gln Val Gln Leu Val Gln Ser Gly Ala Glu Val Lys Lys Pro Gly Ser
 1                5                  10                  15

Ser Val Lys Val Ser Cys Lys Ala Ser Gly Gly Thr Phe Arg Asn His
                 20                  25                  30

Ala Trp Ser Trp Val Arg Gln Ala Pro Gly Gln Gly Leu Glu Trp Met
             35                  40                  45

Gly Trp Ile Ser Ala Tyr Asn Gly Tyr Thr Thr Tyr Ala Glu Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Val Ser Ala Glu Tyr Ala Glu Asp Trp Ser Leu His Tyr Tyr
                100                 105                 110

Tyr Gly Met Asp Val Trp Gly Gln Gly Thr Leu Val Thr Val Ser Ser
            115                 120                 125

<210> SEQ ID NO 90
<211> LENGTH: 110
<212> TYPE: PRT
<213> ORGANISM: Homo sapiens

<400> SEQUENCE: 90

Gln Ser Val Leu Thr Gln Pro Pro Ser Val Ser Ala Ala Pro Gly Gln
 1                5                  10                  15

Glu Val Thr Ile Ser Cys Ser Gly Ser Asn Ser Asn Ile Gly Asn Asn
                 20                  25                  30

Tyr Val Ser Trp Tyr Gln Gln Leu Pro Gly Thr Ala Pro Lys Leu Leu
            35                  40                  45

Ile Tyr Ser Thr Asn Glu Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Ala Leu Phe Gly Gly Gly Thr Lys Leu Thr Val Leu
                100                 105                 110

<210> SEQ ID NO 91
<211> LENGTH: 128
```

```
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Asn His
            20                  25                  30

Ala Trp Ser Trp Val Arg Gln Ala Pro Gly Gln Gly Leu Glu Trp Met
        35                  40                  45

Gly Trp Ile Ser Ala Tyr Asn Gly Tyr Thr Tyr Ala Ser Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Ser Tyr Ala Ser Asp Trp Ser Val His Tyr Tyr
            100                 105                 110

Tyr Gly Met Asp Val Trp Gly Gln Gly Thr Leu Val Thr Val Ser Ser
            115                 120                 125

<210> SEQ ID NO 92
<211> LENGTH: 110
<212> TYPE: PRT
<213> ORGANISM: Homo sapiens

<400> SEQUENCE: 92

Gln Ser Val Leu Thr Gln Pro Pro Ser Val Ser Ala Ala Pro Gly Gln
 1               5                  10                  15

Glu Val Thr Ile Ser Cys Ser Gly Ser Asn Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Ala Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Val Val Phe Gly Gly Gly Thr Lys Leu Thr Val Leu
            100                 105                 110

<210> SEQ ID NO 93
<211> LENGTH: 128
<212> TYPE: PRT
<213> ORGANISM: Homo sapiens

<400> SEQUENCE: 93

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Asn His
            20                  25                  30

Ala Trp Ser Trp Val Arg Gln Ala Pro Gly Gln Gly Leu Glu Trp Met
        35                  40                  45

Gly Trp Ile Ser Ala Tyr Asn Gly Tyr Thr Tyr Ala Ser Lys Leu
    50                  55                  60

Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Val Ser Ala Ser Tyr Asn Ser Asp Trp Ser Val His Tyr Tyr
                100                 105                 110

Tyr Gly Met Asp Val Trp Gly Gln Gly Thr Leu Val Thr Val Ser Ser
            115                 120                 125

<210> SEQ ID NO 94
<211> LENGTH: 110
<212> TYPE: PRT
<213> ORGANISM: Homo sapiens

<400> SEQUENCE: 94

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Ala Glu Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Val Leu Phe Gly Gly Gly Thr Lys Leu Thr Val Leu
                100                 105                 110

<210> SEQ ID NO 95
<211> LENGTH: 128
<212> TYPE: PRT
<213> ORGANISM: Homo sapiens

<400> SEQUENCE: 95

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
                20                  25                  30

Ala Trp Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Glu Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Ser Tyr Ala Ser Asp Trp Ser Leu His Tyr Tyr
                100                 105                 110

Tyr Gly Met Asp Val Trp Gly Gln Gly Thr Leu Val Thr Val Ser Ser
            115                 120                 125

<210> SEQ ID NO 96
<211> LENGTH: 110
<212> TYPE: PRT
<213> ORGANISM: Homo sapiens

<400> SEQUENCE: 96
```

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Glu Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Phe Asp Ser Ser Leu
                85                  90                  95

Ser Ala Ala Leu Phe Gly Gly Gly Thr Lys Leu Thr Val Leu
                100                 105                 110

<210> SEQ ID NO 97
<211> LENGTH: 128
<212> TYPE: PRT
<213> ORGANISM: Homo sapiens

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
                20                  25                  30

Ala Trp Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Glu Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Ala Glu Asp Trp Ser Leu His Tyr Tyr
                100                 105                 110

Tyr Gly Met Asp Val Trp Gly Gln Gly Thr Leu Val Thr Val Ser Ser
            115                 120                 125

<210> SEQ ID NO 98
<211> LENGTH: 110
<212> TYPE: PRT
<213> ORGANISM: Homo sapiens

<400> SEQUENCE: 98

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Pro Asn Asn
                20                  25                  30

Tyr Val Ser Trp Tyr Gln Gln Leu Pro Gly Thr Ala Pro Lys Leu Leu
            35                  40                  45

Ile Tyr Ser Thr Ser Glu Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

```
Ser Ala Val Val Phe Gly Gly Gly Thr Lys Leu Thr Val Leu
            100                 105                 110

<210> SEQ ID NO 99
<211> LENGTH: 128
<212> TYPE: PRT
<213> ORGANISM: Homo sapiens

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr Thr Tyr Ala Ser Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Ser Tyr Asn Glu Asp Trp Ser Leu His Tyr Tyr
            100                 105                 110

Tyr Gly Met Asp Val Trp Gly Gln Gly Thr Leu Val Thr Val Ser Ser
        115                 120                 125

<210> SEQ ID NO 100
<211> LENGTH: 110
<212> TYPE: PRT
<213> ORGANISM: Homo sapiens

<400> SEQUENCE: 100

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Ser Asn Arg Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Phe Asp Ser Ser Leu
                85                  90                  95

Ser Ala Val Val Phe Gly Gly Gly Thr Lys Leu Thr Val Leu
            100                 105                 110

<210> SEQ ID NO 101
<211> LENGTH: 128
<212> TYPE: PRT
<213> ORGANISM: Homo sapiens

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30
```

Ala Tyr Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Ser Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Ser Tyr Asn Ser Asp Trp Ser Val His Tyr Tyr
            100                 105                 110

Tyr Gly Met Asp Val Trp Gly Gln Gly Thr Leu Val Thr Val Ser Ser
            115                 120                 125

<210> SEQ ID NO 102
<211> LENGTH: 110
<212> TYPE: PRT
<213> ORGANISM: Homo sapiens

<400> SEQUENCE: 102

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Thr Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Glu Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Leu Leu Phe Gly Gly Gly Thr Lys Leu Thr Val Leu
            100                 105                 110

<210> SEQ ID NO 103
<211> LENGTH: 128
<212> TYPE: PRT
<213> ORGANISM: Homo sapiens

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
            35                  40                  45

Gly Trp Ile Ser Ala Tyr Asn Gly Tyr Thr Thr Tyr Ala Glu Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Ala Ser Asp Trp Ser Leu His Tyr Tyr
            100                 105                 110

Tyr Gly Met Asp Val Trp Gly Gln Gly Thr Leu Val Thr Val Ser Ser
            115                 120                 125

<210> SEQ ID NO 104
<211> LENGTH: 110
<212> TYPE: PRT
<213> ORGANISM: Homo sapiens

<400> SEQUENCE: 104

```
Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Pro Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Thr Trp Asp Ser Ser Leu
                85                  90                  95

Ser Ala Val Leu Phe Gly Gly Gly Thr Lys Leu Thr Val Leu
            100                 105                 110
```

<210> SEQ ID NO 105
<211> LENGTH: 128
<212> TYPE: PRT
<213> ORGANISM: Homo sapiens

<400> SEQUENCE: 105

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn His
            20                  25                  30

Ala Tyr Ser Trp Val Arg Gln Ala Pro Gly Gln Gly Leu Glu Trp Met
        35                  40                  45

Gly Trp Ile Ser Ala Tyr Asn Gly Tyr Thr Thr Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ala Glu Tyr Ala Ser Asp Trp Ser Leu His Tyr Tyr
            100                 105                 110

Tyr Gly Met Asp Val Trp Gly Gln Gly Thr Leu Val Thr Val Ser Ser
        115                 120                 125
```

<210> SEQ ID NO 106
<211> LENGTH: 110
<212> TYPE: PRT
<213> ORGANISM: Homo sapiens

<400> SEQUENCE: 106

```
Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Pro Asn
            20                  25                  30

Tyr Val Ser Trp Tyr Gln Gln Leu Pro Gly Thr Ala Pro Lys Leu Leu
        35                  40                  45

Ile Tyr Asp Asn Arg Glu Arg Pro Ser Gly Ile Pro Asp Arg Phe Ser
```

```
            50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Ser Thr Trp Asp Ser Ser Leu
                 85                  90                  95

Ser Ala Gly Val Phe Gly Gly Gly Thr Lys Leu Thr Val Leu
            100                 105                 110

<210> SEQ ID NO 107
<211> LENGTH: 120
<212> TYPE: PRT
<213> ORGANISM: Homo sapiens

<400> SEQUENCE: 107

Glu Val Gln Leu Val Glu Ser Gly Gly Val Val Gln Pro Gly Arg
  1               5                  10                  15

Ser Leu Arg Leu Ser Cys Ala Ala Ser Gly Phe Ile Phe His His Tyr
                 20                  25                  30

Ala Met His Trp Val Arg Gln Ala Pro Gly Lys Gly Leu Glu Trp Val
             35                  40                  45

Ala His Ile Ser Pro Asp Gly Ser Ser Lys Phe Tyr Ala Asp Ser Val
         50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Thr Glu Val Leu Tyr Tyr Gly Ala Asp Ile Trp Gly Gln
            100                 105                 110

Gly Thr Leu Val Thr Val Ser Ser
            115                 120

<210> SEQ ID NO 108
<211> LENGTH: 110
<212> TYPE: PRT
<213> ORGANISM: Homo sapiens

<400> SEQUENCE: 108

Gln Ser Val Leu Thr Gln Pro Pro Ser Val Ser Glu Ala Pro Arg Gln
  1               5                  10                  15

Arg Val Ser Ile Ser Cys Ser Gly Ser Ser Ser Asn Ile Gly Asn Asn
                 20                  25                  30

Ala Val Asn Trp Tyr Gln Gln Leu Pro Gly Lys Ala Pro Lys Leu Leu
             35                  40                  45

Ile Tyr Phe Asp Asp Leu Leu Pro Gln Gly Val Ser Asp Arg Phe Ser
         50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Lys Gly Tyr Val Phe Gly Thr Gly Thr Lys Val Thr Val Leu
            100                 105                 110

<210> SEQ ID NO 109
<211> LENGTH: 120
<212> TYPE: PRT
<213> ORGANISM: Homo sapiens

<400> SEQUENCE: 109
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Leu Asp Gly Ser Tyr Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Thr Glu Val Leu Tyr Tyr Gly Ala Asp Ile Trp Gly Gln
            100                 105                 110

Gly Thr Leu Val Thr Val Ser Ser
        115                 120

<210> SEQ ID NO 110
<211> LENGTH: 110
<212> TYPE: PRT
<213> ORGANISM: Homo sapiens

<400> SEQUENCE: 110

Gln Ser Val Leu Thr Gln Pro Pro Ser Val Ser Glu Ala Pro Arg Gln
1               5                   10                  15

Arg Val Ser Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu His Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asp Ser Leu
            85                  90                  95

Lys Gly Tyr Val Phe Gly Thr Gly Thr Lys Val Thr Val Leu
            100                 105                 110

<210> SEQ ID NO 111
<211> LENGTH: 120
<212> TYPE: PRT
<213> ORGANISM: Homo sapiens

<400> SEQUENCE: 111

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Leu Asp Gly Ser Tyr Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Arg Phe Thr Glu Val Leu Tyr Tyr Gly Ala Asp Ile Trp Gly Gln
            100                 105                 110

Gly Thr Leu Val Thr Val Ser Ser
        115                 120

<210> SEQ ID NO 112
<211> LENGTH: 110
<212> TYPE: PRT
<213> ORGANISM: Homo sapiens

<400> SEQUENCE: 112

Gln Ser Val Leu Thr Gln Pro Pro Ser Val Ser Glu Ala Pro Arg Gln
1               5                   10                  15

Arg Val Ser Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu His Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110

<210> SEQ ID NO 113
<211> LENGTH: 120
<212> TYPE: PRT
<213> ORGANISM: Homo sapiens

<400> SEQUENCE: 113

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Pro Asp Gly Ser Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Tyr Trp Gly Gln
            100                 105                 110

Gly Thr Leu Val Thr Val Ser Ser
        115                 120

<210> SEQ ID NO 114
<211> LENGTH: 110
<212> TYPE: PRT
<213> ORGANISM: Homo sapiens

<400> SEQUENCE: 114

Gln Ser Val Leu Thr Gln Pro Pro Ser Val Ser Glu Ala Pro Arg Gln
1               5                   10                  15
```

```
Arg Val Ser Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110

<210> SEQ ID NO 115
<211> LENGTH: 120
<212> TYPE: PRT
<213> ORGANISM: Homo sapiens

<400> SEQUENCE: 115

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Pro Asp Gly Ser Tyr Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Leu Trp Gly Gln
            100                 105                 110

Gly Thr Leu Val Thr Val Ser Ser
        115                 120

<210> SEQ ID NO 116
<211> LENGTH: 110
<212> TYPE: PRT
<213> ORGANISM: Homo sapiens

<400> SEQUENCE: 116

Gln Ser Val Leu Thr Gln Pro Pro Ser Val Ser Glu Ala Pro Arg Gln
1               5                   10                  15

Arg Val Ser Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110
```

<210> SEQ ID NO 117
<211> LENGTH: 120
<212> TYPE: PRT
<213> ORGANISM: Homo sapiens

<400> SEQUENCE: 117

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Ser Asp Gly Ser Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Leu Trp Gly Gln
            100                 105                 110

Gly Thr Leu Val Thr Val Ser Ser
            115                 120

<210> SEQ ID NO 118
<211> LENGTH: 110
<212> TYPE: PRT
<213> ORGANISM: Homo sapiens

<400> SEQUENCE: 118

Gln Ser Val Leu Thr Gln Pro Pro Ser Val Ser Glu Ala Pro Arg Gln
1               5                   10                  15

Arg Val Ser Ile Ser Cys Ser Gly Ser Ser Asn Val Gly Asn Asn
            20                  25                  30

Ala Val Asn Trp Tyr Gln Gln Leu Pro Gly Lys Ala Pro Lys Leu Leu
        35                  40                  45

Ile Tyr Phe Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110

<210> SEQ ID NO 119
<211> LENGTH: 120
<212> TYPE: PRT
<213> ORGANISM: Homo sapiens

<400> SEQUENCE: 119

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ala Met His Trp Val Arg Gln Ala Pro Gly Lys Gly Leu Glu Trp Val
        35                  40                  45

Ala His Ile Ser Ser Asp Gly Ser Tyr Lys Phe Tyr Ala Asp Ser Val

```
                50                  55                  60
Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Phe Thr Glu Val Leu Tyr Tyr Gly Ala Asp Leu Trp Gly Gln
                100                 105                 110

Gly Thr Leu Val Thr Val Ser Ser
            115                 120

<210> SEQ ID NO 120
<211> LENGTH: 110
<212> TYPE: PRT
<213> ORGANISM: Homo sapiens

<400> SEQUENCE: 120

Gln Ser Val Leu Thr Gln Pro Pro Ser Val Glu Ala Pro Arg Gln
 1               5                  10                  15

Arg Val Ser Ile Ser Cys Ser Gly Ser Ser Asn Ile Gly Asn Asn
                 20                  25                  30

Ala Val Asn Trp Tyr Gln Gln Leu Pro Gly Lys Ala Pro Lys Leu Leu
                 35                  40                  45

Ile Tyr Phe Asp Asp Leu His Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Ser Leu
                 85                  90                  95

Lys Gly Tyr Val Phe Gly Thr Gly Thr Lys Val Thr Val Leu
                100                 105                 110

<210> SEQ ID NO 121
<211> LENGTH: 120
<212> TYPE: PRT
<213> ORGANISM: Homo sapiens

<400> SEQUENCE: 121

Glu Val Gln Leu Val Glu Ser Gly Gly Val Val Gln Pro Gly Arg
 1               5                  10                  15

Ser Leu Arg Leu Ser Cys Ala Ala Ser Gly Phe Ile Phe His His Tyr
                 20                  25                  30

Ala Met His Trp Val Arg Gln Ala Pro Gly Lys Gly Leu Glu Trp Val
                 35                  40                  45

Ala His Ile Ser Pro Asp Gly Ser Tyr Lys Tyr Ala Asp Ser Val
 50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Thr Glu Val Leu Tyr Tyr Gly Ala Asp Ile Trp Gly Gln
                100                 105                 110

Gly Thr Leu Val Thr Val Ser Ser
            115                 120

<210> SEQ ID NO 122
<211> LENGTH: 110
<212> TYPE: PRT
```

<213> ORGANISM: Homo sapiens

<400> SEQUENCE: 122

Gln Ser Val Leu Thr Gln Pro Pro Ser Val Ser Glu Ala Pro Arg Gln
1               5                   10                  15
Arg Val Ser Ile Ser Cys Ser Gly Ser Ser Asn Ile Gly Asn Asn
            20                  25                  30
Ala Val Asn Trp Tyr Gln Gln Leu Pro Gly Lys Ala Pro Lys Leu Leu
        35                  40                  45
Ile Tyr Tyr Asp Asp Leu Leu Pro Ser Gly Val Ser Asn Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Lys Gly Tyr Val Phe Gly Thr Gly Thr Lys Val Thr Val Leu
            100                 105                 110

<210> SEQ ID NO 123
<211> LENGTH: 120
<212> TYPE: PRT
<213> ORGANISM: Homo sapiens

<400> SEQUENCE: 123

Glu Val Gln Leu Val Glu Ser Gly Gly Gly Val Val Gln Pro Gly Arg
1               5                   10                  15
Ser Leu Arg Leu Ser Cys Ala Ala Ser Gly Phe Ile Phe His His Tyr
            20                  25                  30
Ala Met His Trp Val Arg Gln Ala Pro Gly Lys Gly Leu Glu Trp Val
        35                  40                  45
Ala His Ile Ser Pro Asp Gly Ser Lys Phe Tyr Ala Asp Ser Val
    50                  55                  60
Lys Gly Arg Phe Thr Val Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Phe Thr Glu Val Leu Tyr Tyr Gly Ala Asp Leu Trp Gly Gln
            100                 105                 110
Gly Thr Leu Val Thr Val Ser Ser
            115                 120

<210> SEQ ID NO 124
<211> LENGTH: 110
<212> TYPE: PRT
<213> ORGANISM: Homo sapiens

<400> SEQUENCE: 124

Gln Ser Val Leu Thr Gln Pro Pro Ser Val Ser Glu Ala Pro Arg Gln
1               5                   10                  15
Arg Val Ser Ile Ser Cys Ser Gly Ser Ser Asn Ile Gly Asn Asn
            20                  25                  30
Ala Val Asn Trp Tyr Gln Gln Leu Pro Gly Lys Ala Pro Lys Leu Leu
        35                  40                  45
Ile Tyr Tyr Asp Asp Leu Leu Pro Ser Gly Val Ser Asp Arg Phe Ser
    50                  55                  60
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val Leu
            100                 105                 110

<210> SEQ ID NO 125
<211> LENGTH: 120
<212> TYPE: PRT
<213> ORGANISM: Homo sapiens

<400> SEQUENCE: 125

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe His His Tyr
            20                  25                  30

Ser Met His Trp Val Arg Gln Ala Pro Gly Lys Gly Leu Glu Trp Val
        35                  40                  45

Ala His Ile Ser Ser Asp Gly Ser Ser Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Glu Val Leu Tyr Tyr Gly Ala Asp Leu Trp Gly Gln
            100                 105                 110

Gly Thr Leu Val Thr Val Ser Ser
        115                 120

<210> SEQ ID NO 126
<211> LENGTH: 109
<212> TYPE: PRT
<213> ORGANISM: Homo sapiens

<400> SEQUENCE: 126

Gln Ser Val Leu Thr Gln Pro Pro Ser Val Ser Glu Ala Pro Arg Gln
1               5                   10                  15

Arg Val Ser Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Thr Gly Thr Lys Val Thr Val
            100                 105

<210> SEQ ID NO 127
<211> LENGTH: 120
<212> TYPE: PRT
<213> ORGANISM: Homo sapiens

<400> SEQUENCE: 127

Glu Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser His Tyr
            20                  25                  30

Ala Met His Trp Val Arg Gln Ala Pro Gly Lys Gly Leu Glu Trp Val
            35                  40                  45

Ala His Ile Ser Leu Asp Gly Ser Ser Lys Phe Tyr Ala Asp Ser Val
            50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Phe Thr Glu Val Leu Tyr Tyr Gly Ala Asp Leu Trp Gly Gln
            100                 105                 110

Gly Thr Leu Val Thr Val Ser Ser
            115                 120

<210> SEQ ID NO 128
<211> LENGTH: 110
<212> TYPE: PRT
<213> ORGANISM: Homo sapiens

<400> SEQUENCE: 128

Gln Ser Val Leu Thr Gln Pro Pro Ser Val Ser Glu Ala Pro Arg Gln
 1               5                  10                  15

Arg Val Ser Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
            85                  90                  95

Lys Gly Tyr Val Phe Gly Thr Gly Thr Lys Val Thr Val Leu
            100                 105                 110
```